United States Patent
Kohler et al.

(10) Patent No.: US 9,561,270 B2
(45) Date of Patent: Feb. 7, 2017

(54) METHODS OF REDUCING VIRUCIDAL ACTIVITY IN PCV-2 COMPOSITIONS AND PCV-2 COMPOSITIONS WITH AN IMPROVED IMMUNOGENICITY

(75) Inventors: Caroline Ann Kohler, St. Joseph, MO (US); Guosong Zhao, St. Joseph, MO (US); Ali Khazraeinazmpour, St. Joseph, MO (US); Bernd Colin Eichenmueller, St. Joseph, MO (US); Marc Allan Eichmeyer, Bondurant, IA (US); Gregory Haiwick, Ankeny, IA (US); Merrill Lynn Schaeffer, St. Joseph, MO (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 527 days.

(21) Appl. No.: 12/874,994

(22) Filed: Sep. 2, 2010

(65) Prior Publication Data
US 2011/0059126 A1 Mar. 10, 2011

Related U.S. Application Data

(60) Provisional application No. 61/239,192, filed on Sep. 2, 2009, provisional application No. 61/309,408, filed on Mar. 1, 2010.

(51) Int. Cl.
  *C12N 7/02* (2006.01)
  *A61K 39/12* (2006.01)
  *A61K 39/00* (2006.01)

(52) U.S. Cl.
  CPC ....... *A61K 39/12* (2013.01); *A61K 2039/5252* (2013.01); *A61K 2039/5258* (2013.01);
  (Continued)

(58) Field of Classification Search
  None
  See application file for complete search history.

(56) References Cited

U.S. PATENT DOCUMENTS

| 3,080,291 A | 3/1963 | Sinha et al. |
| 3,137,631 A | 6/1964 | Soloway |

(Continued)

FOREIGN PATENT DOCUMENTS

| CA | 2103460 A1 | 12/1992 |
| CA | 2305623 A1 | 4/1999 |

(Continued)

OTHER PUBLICATIONS

Kim et al., "Efficacy of different disinfectants in vitro against porcine circovirus type 2," The Veterinary Record, 164, pp. 599-600 (2009).*

(Continued)

*Primary Examiner* — Janet L Andres
*Assistant Examiner* — M. Franco Salvoza
(74) *Attorney, Agent, or Firm* — Michael P. Morris; Wendy M. Gombert

(57) ABSTRACT

The present invention provides methods of reducing the virucidal activity of a composition comprising a PCV-2 antigen as well as antigenic preparations and immunogenic compositions comprising a PCV-2 antigen, wherein the virucidal activity has been reduced. In addition, the present invention also relates to a method of increasing the immunogenicity of an immunogenic composition comprising a PCV-2 antigen as well as immunogenic composition with an increased immunogenicity.

21 Claims, 1 Drawing Sheet

(52) U.S. Cl.
CPC .............. *A61K 2039/552* (2013.01); *A61K 2039/55511* (2013.01); *A61K 2039/55555* (2013.01); *C12N 2750/10034* (2013.01)

(56) References Cited

U.S. PATENT DOCUMENTS

| | | | |
|---|---|---|---|
| 3,959,457 A | 5/1976 | Speaker et al. | |
| 4,015,100 A | 3/1977 | Gnanamuthu et al. | |
| 4,122,167 A | 10/1978 | Buynak et al. | |
| 4,205,060 A | 5/1980 | Monsimer et al. | |
| 4,224,412 A | 9/1980 | Dorofeev et al. | |
| 4,452,747 A | 6/1984 | Gersonde et al. | |
| 4,468,346 A | 8/1984 | Paul et al. | |
| 4,554,159 A | 11/1985 | Roizman et al. | |
| 4,606,940 A | 8/1986 | Frank et al. | |
| 4,636,485 A | 1/1987 | van der Smissen | |
| 4,744,933 A | 5/1988 | Rha et al. | |
| 4,753,884 A | 6/1988 | Kit et al. | |
| 4,810,493 A | 3/1989 | Patrick et al. | |
| 4,921,706 A | 5/1990 | Roberts et al. | |
| 4,927,637 A | 5/1990 | Morano et al. | |
| 4,944,948 A | 7/1990 | Uster et al. | |
| 5,008,050 A | 4/1991 | Cullis et al. | |
| 5,009,956 A | 4/1991 | Baumann | |
| 5,132,117 A | 7/1992 | Speaker et al. | |
| 5,202,430 A | 4/1993 | Brian et al. | |
| 5,206,163 A | 4/1993 | Renard et al. | |
| 5,213,759 A | 5/1993 | Castberg et al. | |
| 5,322,774 A | 6/1994 | Peakman et al. | |
| 5,419,907 A | 5/1995 | Paul et al. | |
| 5,436,001 A | 7/1995 | Kramer | |
| 5,476,778 A | 12/1995 | Chladek et al. | |
| 5,510,258 A | 4/1996 | Sanderson et al. | |
| 5,565,205 A | 10/1996 | Petersen et al. | |
| 5,580,557 A | 12/1996 | Kramer | |
| 5,587,164 A | 12/1996 | Sanderson et al. | |
| 5,597,721 A | 1/1997 | Brun et al. | |
| 5,620,691 A | 4/1997 | Wensvoort et al. | |
| 5,674,500 A | 10/1997 | Peeters et al. | |
| 5,677,429 A | 10/1997 | Benfield | |
| 5,683,865 A | 11/1997 | Collins et al. | |
| 5,690,940 A | 11/1997 | Joo | |
| 5,695,766 A | 12/1997 | Paul et al. | |
| 5,698,203 A | 12/1997 | Visser et al. | |
| 5,733,555 A | 3/1998 | Chu | |
| 5,789,388 A | 8/1998 | Visser et al. | |
| 5,840,563 A | 11/1998 | Chladek et al. | |
| 5,846,805 A | 12/1998 | Collins et al. | |
| 5,858,729 A | 1/1999 | Van Woensel et al. | |
| 5,866,401 A | 2/1999 | Hesse | |
| 5,885,823 A | 3/1999 | Knittel et al. | |
| 5,888,513 A | 3/1999 | Plana Duran et al. | |
| 5,910,310 A | 6/1999 | Heinen et al. | |
| 5,925,359 A | 7/1999 | Van Woensel et al. | |
| 5,968,525 A | 10/1999 | Fitzgerald et al. | |
| 5,976,537 A | 11/1999 | Mengeling et al. | |
| 5,989,563 A | 11/1999 | Chladek et al. | |
| 5,998,601 A | 12/1999 | Murtaugh et al. | |
| 6,001,370 A | 12/1999 | Burch et al. | |
| 6,015,663 A | 1/2000 | Wesley et al. | |
| 6,042,830 A | 3/2000 | Chladek et al. | |
| 6,080,570 A | 6/2000 | Chladek et al. | |
| 6,110,467 A | 8/2000 | Paul et al. | |
| 6,110,468 A | 8/2000 | Collins et al. | |
| 6,149,917 A | 11/2000 | Fanget et al. | |
| 6,194,210 B1 | 2/2001 | Leu et al. | |
| 6,197,310 B1 | 3/2001 | Wensvoort et al. | |
| 6,217,883 B1 | 4/2001 | Allan et al. | |
| 6,241,990 B1 | 6/2001 | Collins et al. | |
| 6,251,397 B1 | 6/2001 | Paul et al. | |
| 6,251,404 B1 | 6/2001 | Paul et al. | |
| 6,268,199 B1 | 7/2001 | Meulenberg et al. | |
| 6,287,856 B1 | 9/2001 | Poet et al. | |
| 6,294,176 B1 | 9/2001 | Cochran et al. | |
| 6,368,601 B1 | 4/2002 | Allan et al. | |
| 6,380,376 B1 | 4/2002 | Paul et al. | |
| 6,391,314 B1 | 5/2002 | Allan et al. | |
| 6,455,245 B1 | 9/2002 | Wensvoort et al. | |
| 6,495,138 B1 | 12/2002 | van Nieuwstadt et al. | |
| 6,497,883 B1 | 12/2002 | Bublot et al. | |
| 6,498,008 B2 | 12/2002 | Collins et al. | |
| 6,500,662 B1 | 12/2002 | Calvert et al. | |
| 6,517,843 B1 * | 2/2003 | Ellis et al. | 424/204.1 |
| 6,592,873 B1 | 7/2003 | Paul et al. | |
| 6,641,819 B2 | 11/2003 | Mengeling et al. | |
| 6,660,272 B2 | 12/2003 | Allan et al. | |
| 6,660,513 B2 | 12/2003 | Mengeling et al. | |
| 6,703,023 B1 | 3/2004 | Jestin et al. | |
| 6,773,908 B1 | 8/2004 | Paul et al. | |
| 6,794,163 B2 | 9/2004 | Liu et al. | |
| 6,806,086 B2 | 10/2004 | Wensvoort et al. | |
| 6,808,900 B2 | 10/2004 | Simonsen | |
| 6,841,364 B2 | 1/2005 | Yuan et al. | |
| 6,846,477 B2 | 1/2005 | Keich et al. | |
| 6,855,315 B2 | 2/2005 | Collins et al. | |
| 6,943,152 B1 | 9/2005 | Audonnet et al. | |
| 6,953,581 B2 | 10/2005 | Allan et al. | |
| 6,982,160 B2 | 1/2006 | Collins et al. | |
| 7,018,638 B2 | 3/2006 | Chu et al. | |
| 7,081,342 B2 | 7/2006 | Mengeling et al. | |
| 7,109,025 B1 | 9/2006 | Eloit et al. | |
| 7,122,192 B2 | 10/2006 | Allan et al. | |
| 7,122,347 B2 | 10/2006 | Verheije et al. | |
| 7,132,106 B2 | 11/2006 | Calvert et al. | |
| 7,144,698 B2 | 12/2006 | Wang et al. | |
| 7,148,015 B2 | 12/2006 | Jestin et al. | |
| 7,169,394 B2 | 1/2007 | Chu et al. | |
| 7,172,899 B2 | 2/2007 | Liu et al. | |
| 7,179,472 B2 | 2/2007 | Jestin et al. | |
| 7,192,594 B2 | 3/2007 | Haines et al. | |
| 7,211,379 B2 | 5/2007 | Ellis et al. | |
| 7,223,407 B2 | 5/2007 | Jestin et al. | |
| 7,223,594 B2 | 5/2007 | Jestin et al. | |
| 7,232,680 B2 | 6/2007 | Calvert et al. | |
| 7,244,433 B2 | 7/2007 | Jestin et al. | |
| 7,258,865 B2 | 8/2007 | Jestin et al. | |
| 7,261,898 B2 | 8/2007 | Jestin et al. | |
| 7,264,804 B2 | 9/2007 | Collins et al. | |
| 7,273,617 B2 | 9/2007 | Yuan et al. | |
| 7,276,353 B2 | 10/2007 | Meng et al. | |
| 7,279,166 B2 | 10/2007 | Meng et al. | |
| 7,297,537 B2 | 11/2007 | Jestin et al. | |
| 7,300,785 B2 | 11/2007 | Meerts et al. | |
| 7,312,030 B2 | 12/2007 | van Rijn et al. | |
| 7,312,065 B2 | 12/2007 | Roof et al. | |
| 7,314,628 B2 | 1/2008 | Jestin et al. | |
| 7,323,330 B2 | 1/2008 | Jestin et al. | |
| 7,335,361 B2 | 2/2008 | Liao et al. | |
| 7,335,473 B2 | 2/2008 | Wensvoort et al. | |
| 7,358,075 B2 | 4/2008 | Allibert et al. | |
| 7,368,117 B2 | 5/2008 | Fetzer et al. | |
| 7,371,395 B2 | 5/2008 | Parisot et al. | |
| 7,390,494 B2 | 6/2008 | Jestin et al. | |
| 7,405,075 B2 | 7/2008 | Jestin et al. | |
| 7,407,803 B2 | 8/2008 | Jestin et al. | |
| 7,425,444 B2 | 9/2008 | Jestin et al. | |
| 7,618,797 B2 | 11/2009 | Calvert et al. | |
| 7,632,636 B2 | 12/2009 | Roof et al. | |
| 7,691,389 B2 | 4/2010 | Calvert et al. | |
| 7,700,285 B1 * | 4/2010 | Eichmeyer et al. | 435/6.14 |
| 7,722,878 B2 | 5/2010 | Vaughn et al. | |
| 7,758,865 B2 | 7/2010 | Jestin et al. | |
| 7,829,101 B2 | 11/2010 | Eichmeyer et al. | |
| 7,829,273 B2 | 11/2010 | Roof et al. | |
| 7,829,274 B2 | 11/2010 | Fachinger et al. | |
| 7,833,707 B2 | 11/2010 | Eichmeyer et al. | |
| 7,838,213 B2 | 11/2010 | Roof et al. | |
| 7,838,214 B2 | 11/2010 | Roof et al. | |
| 7,897,343 B2 | 3/2011 | Wensvoort et al. | |
| 7,910,306 B2 | 3/2011 | Eichmeyer et al. | |
| 7,914,992 B2 | 3/2011 | Fachinger et al. | |
| 7,943,298 B2 | 5/2011 | Fachinger et al. | |
| 7,951,907 B2 | 5/2011 | Jestin et al. | |
| 7,968,285 B2 | 6/2011 | Roof et al. | |

(56) References Cited

U.S. PATENT DOCUMENTS

| | | |
|---|---|---|
| 8,025,888 B2 | 9/2011 | Eichmeyer et al. |
| 8,110,390 B2 | 2/2012 | Faaberg et al. |
| 8,496,940 B2 | 7/2013 | Fachinger et al. |
| 8,865,183 B2 | 10/2014 | Fachinger et al. |
| 9,011,868 B2 | 4/2015 | Roof et al. |
| 9,011,872 B2 | 4/2015 | Eichmeyer et al. |
| 2002/0012670 A1 | 1/2002 | Elbers et al. |
| 2002/0098573 A1 | 7/2002 | Meulenberg et al. |
| 2002/0146431 A1 | 10/2002 | Allan et al. |
| 2002/0172690 A1 | 11/2002 | Calvert et al. |
| 2003/0049274 A1 | 3/2003 | Meulenberg et al. |
| 2003/0096377 A1 | 5/2003 | Meng et al. |
| 2003/0118608 A1 | 6/2003 | Wensvoort et al. |
| 2003/0157689 A1 | 8/2003 | Calvert et al. |
| 2003/0170270 A1 | 9/2003 | Meng et al. |
| 2003/0199581 A1 | 10/2003 | Seligson et al. |
| 2003/0215455 A1 | 11/2003 | Reynolds et al. |
| 2003/0219732 A1 | 11/2003 | van Rijn et al. |
| 2004/0009190 A1 | 1/2004 | Elbers et al. |
| 2004/0062775 A1 | 4/2004 | Jestin et al. |
| 2004/0076635 A1 | 4/2004 | Jestin et al. |
| 2004/0091502 A1 | 5/2004 | Jestin et al. |
| 2004/0132014 A1 | 7/2004 | Wensvoort et al. |
| 2004/0132178 A1 | 7/2004 | Haines et al. |
| 2004/0161410 A1 | 8/2004 | Jestin et al. |
| 2004/0197872 A1 | 10/2004 | Meulenberg et al. |
| 2004/0208901 A1 | 10/2004 | Ellsworth et al. |
| 2004/0213805 A1 | 10/2004 | Verheije |
| 2004/0224327 A1 | 11/2004 | Meulenberg et al. |
| 2004/0253270 A1 | 12/2004 | Meng et al. |
| 2004/0258715 A1 | 12/2004 | Allan et al. |
| 2004/0265848 A1 | 12/2004 | Jestin et al. |
| 2005/0008651 A1 | 1/2005 | Jestin et al. |
| 2005/0013823 A1 | 1/2005 | Keich et al. |
| 2005/0031647 A1 | 2/2005 | Roof et al. |
| 2005/0058653 A1 | 3/2005 | Ellis et al. |
| 2005/0079185 A1 | 4/2005 | Parisot et al. |
| 2005/0084497 A1 | 4/2005 | Jestin et al. |
| 2005/0147966 A1 | 7/2005 | Meng et al. |
| 2005/0238662 A1 | 10/2005 | Jestin et al. |
| 2006/0002952 A1 | 1/2006 | Haines et al. |
| 2006/0029617 A1 | 2/2006 | Charreyre et al. |
| 2006/0063151 A1 | 3/2006 | Roof et al. |
| 2006/0083756 A1 | 4/2006 | Jestin et al. |
| 2006/0115489 A1 | 6/2006 | Birkett et al. |
| 2006/0204522 A1 | 9/2006 | Kroll et al. |
| 2006/0205033 A1 | 9/2006 | Meulenberg et al. |
| 2006/0222659 A1 | 10/2006 | Jestin et al. |
| 2006/0228373 A1 | 10/2006 | Chu et al. |
| 2006/0233831 A1 | 10/2006 | Parisot et al. |
| 2006/0240041 A1 | 10/2006 | Meulenberg et al. |
| 2006/0246425 A1 | 11/2006 | Allibert et al. |
| 2006/0286123 A1 | 12/2006 | Fetzer et al. |
| 2007/0003570 A1 | 1/2007 | Murtaugh et al. |
| 2007/0042000 A1 | 2/2007 | Mengeling et al. |
| 2007/0196879 A1 | 8/2007 | Chabriere et al. |
| 2008/0181910 A1 | 7/2008 | Roof et al. |
| 2008/0226669 A1 | 9/2008 | Roof et al. |
| 2008/0233147 A1 | 9/2008 | Jestin et al. |
| 2008/0261887 A1 | 10/2008 | Roof et al. |
| 2008/0267995 A1 | 10/2008 | Roof et al. |
| 2008/0279875 A1 | 11/2008 | Roof et al. |
| 2008/0279876 A1 | 11/2008 | Roof et al. |
| 2008/0279889 A1 | 11/2008 | Roof et al. |
| 2009/0016992 A1 | 1/2009 | Eichmeyer et al. |
| 2009/0017064 A1 | 1/2009 | Wu et al. |
| 2009/0022751 A1 | 1/2009 | Eichmeyer et al. |
| 2009/0042245 A1 | 2/2009 | Eichmeyer et al. |
| 2009/0148474 A1 | 6/2009 | Roof et al. |
| 2010/0003278 A1 | 1/2010 | Roof et al. |
| 2010/0028860 A1 | 2/2010 | Roof et al. |
| 2010/0129398 A1 | 5/2010 | Klinge et al. |
| 2010/0136060 A1 | 6/2010 | Kolb |
| 2010/0184016 A1* | 7/2010 | Lefebvre et al. ............... 435/5 |
| 2010/0189743 A1 | 7/2010 | Jestin et al. |
| 2011/0033495 A1 | 2/2011 | Roof et al. |
| 2011/0059126 A1 | 3/2011 | Kohler et al. |
| 2011/0091499 A1 | 4/2011 | Fachinger et al. |
| 2011/0104201 A1 | 5/2011 | Mengeling et al. |
| 2011/0117129 A1 | 5/2011 | Roof et al. |
| 2011/0195088 A1 | 8/2011 | Roof et al. |
| 2011/0217327 A1 | 9/2011 | Roof et al. |
| 2011/0274710 A1 | 11/2011 | Eichmeyer et al. |
| 2012/0189655 A1 | 7/2012 | Wu et al. |
| 2013/0183329 A1 | 7/2013 | Zhang et al. |
| 2013/0230558 A1 | 9/2013 | Ohnesorge et al. |
| 2013/0273099 A1 | 10/2013 | Fachinger et al. |
| 2013/0302370 A1 | 11/2013 | Fachinger et al. |
| 2014/0377298 A1 | 12/2014 | Fachinger et al. |
| 2015/0174233 A1 | 6/2015 | Roof et al. |

FOREIGN PATENT DOCUMENTS

| | | |
|---|---|---|
| CN | 1579553 A | 7/1920 |
| CN | 1458167 A | 11/2003 |
| DE | 145705 A1 | 1/1981 |
| EP | 208672 A1 | 1/1987 |
| EP | 0440219 A1 | 8/1991 |
| EP | 0529584 A2 | 3/1993 |
| EP | 587780 A1 | 3/1994 |
| EP | 0595436 A2 | 5/1994 |
| EP | 0610250 A1 | 8/1994 |
| EP | 676467 A2 | 10/1995 |
| EP | 732340 A2 | 9/1996 |
| EP | 0835929 A1 | 4/1998 |
| EP | 0835930 A1 | 4/1998 |
| EP | 0839912 A1 | 5/1998 |
| EP | 1018557 A2 | 7/2000 |
| EP | 1050584 A1 | 11/2000 |
| EP | 1281760 A1 | 2/2003 |
| EP | 1386617 A1 | 2/2004 |
| FR | 2602791 A1 | 2/1988 |
| GB | 2282811 A | 4/1995 |
| GB | 2289279 A | 11/1995 |
| JP | 62/198626 A | 9/1987 |
| JP | 2002247979 A | 9/2002 |
| JP | 2005511075 A | 4/2005 |
| WO | 8803410 A1 | 5/1988 |
| WO | 8906972 A1 | 8/1989 |
| WO | 8908701 A1 | 9/1989 |
| WO | 9007935 A1 | 7/1990 |
| WO | 9118627 A1 | 12/1991 |
| WO | 9203157 A1 | 3/1992 |
| WO | 9221375 A1 | 12/1992 |
| WO | 9303760 A1 | 3/1993 |
| WO | 9306211 A1 | 4/1993 |
| WO | 9307898 A1 | 4/1993 |
| WO | 9314196 A1 | 7/1993 |
| WO | 9316726 A2 | 9/1993 |
| WO | 9418311 A1 | 8/1994 |
| WO | 9528227 A1 | 10/1995 |
| WO | 9530437 A1 | 11/1995 |
| WO | 9531550 A1 | 11/1995 |
| WO | 9604010 A1 | 2/1996 |
| WO | 9606619 A1 | 3/1996 |
| WO | 9636356 A1 | 11/1996 |
| WO | 9640932 A1 | 12/1996 |
| WO | 9700696 A1 | 1/1997 |
| WO | 9731651 A1 | 9/1997 |
| WO | 9731652 A1 | 9/1997 |
| WO | 9818933 A1 | 5/1998 |
| WO | 9835023 A1 | 8/1998 |
| WO | 9850426 A1 | 11/1998 |
| WO | 9855625 A1 | 12/1998 |
| WO | 9855626 A2 | 12/1998 |
| WO | 9918214 A1 | 4/1999 |
| WO | 9929717 A3 | 6/1999 |
| WO | 9929871 A3 | 6/1999 |
| WO | 0001409 A2 | 1/2000 |
| WO | 0047756 A1 | 8/2000 |
| WO | 0053787 A1 | 9/2000 |
| WO | 0065032 A1 | 11/2000 |
| WO | 0077188 A2 | 12/2000 |
| WO | 0077216 A2 | 12/2000 |

(56) References Cited

FOREIGN PATENT DOCUMENTS

| | | | | |
|---|---|---|---|---|
| WO | 0116330 | A2 | 3/2001 | |
| WO | 0117550 | A2 | 3/2001 | |
| WO | 0117551 | A2 | 3/2001 | |
| WO | 0117556 | A1 | 3/2001 | |
| WO | 0134191 | A1 | 5/2001 | |
| WO | 0145735 | A2 | 6/2001 | |
| WO | 0159077 | A1 | 8/2001 | |
| WO | 0190363 | A1 | 11/2001 | |
| WO | 0196377 | A2 | 12/2001 | |
| WO | 0249666 | A2 | 6/2002 | |
| WO | 02060921 | A2 | 8/2002 | |
| WO | WO 02077210 | A2 * | 10/2002 | ........... C07K 14/005 |
| WO | 02095040 | A1 | 11/2002 | |
| WO | 03003941 | A2 | 1/2003 | |
| WO | 03049703 | A2 | 6/2003 | |
| WO | 03062407 | A1 | 7/2003 | |
| WO | 2004026336 | A1 | 4/2004 | |
| WO | 2004058142 | A2 | 7/2004 | |
| WO | 2004069184 | A2 | 8/2004 | |
| WO | 2005009462 | A2 | 2/2005 | |
| WO | 2005092069 | A2 | 10/2005 | |
| WO | 2005112995 | A1 | 12/2005 | |
| WO | 2006002193 | A2 | 1/2006 | |
| WO | 2006034319 | A2 | 3/2006 | |
| WO | 2006068663 | A2 | 6/2006 | |
| WO | 2006072065 | A2 | 7/2006 | |
| WO | 2006074986 | A2 | 7/2006 | |
| WO | 2006113372 | A2 | 10/2006 | |
| WO | 2006113373 | A2 | 10/2006 | |
| WO | 2007002321 | A2 | 1/2007 | |
| WO | 2007028823 | A1 | 3/2007 | |
| WO | 2007064742 | A2 | 6/2007 | |
| WO | 2007076520 | A2 | 7/2007 | |
| WO | 2007094893 | A2 | 8/2007 | |
| WO | 2008073464 | A2 | 6/2008 | |
| WO | 2008073490 | A1 | 6/2008 | |
| WO | 2008076915 | A2 | 6/2008 | |
| WO | 2008081015 | A1 | 7/2008 | |
| WO | 2008098909 | A1 | 8/2008 | |
| WO | 2008109237 | A2 | 9/2008 | |
| WO | 2008121958 | A1 | 10/2008 | |
| WO | 2009030684 | A2 | 3/2009 | |
| WO | 2009085912 | A1 | 7/2009 | |
| WO | 2009103037 | A1 | 8/2009 | |
| WO | 2009127684 | A1 | 10/2009 | |
| WO | 2009128878 | A1 | 10/2009 | |
| WO | 2010025109 | A1 | 3/2010 | |
| WO | 20110128415 | A1 | 10/2011 | |

OTHER PUBLICATIONS

Royer et al., "Susceptibility of porcine circovirus type 2 to commercial and laboratory disinfectants," Journal of Swine Health and Production, vol. 9, No. 6, pp. 281-284 (2001).*
Morenwiser, "Downstream processing of viral vectors and vaccines," Gene Therapy 12: S103-S110 (2005).*
Roush et al., "Advances in Primary Recovery: Centrifugation and Membrane Technology," Biotechnol. Prog: 24: 488-495 (2008).*
Saxena et al., "Membrane-based techniques for the separation and purification of protein: An overview," Advances in Colloid and Interface Science 145: 1-22 (2009).*
Martin et al., "Virucidal efficacy of nine commercial disinfectants against porcine circovirus type 2," Veterinary Journal 177: 388-393 (2008).*
"Carbomer". PharmEuropa, vol. 8, No. 2, Jun. 1996, pp. 221-223.
"Dutch Team Isolates Mystery Pig Disease Agent", Animal Pharm, vol. 230, Abstract No. 00278268, Jun. 21, 1991, p. 21.
"For purification of viral RNA from Plasma, Serum, Cell-free body fluids, Cell-Culture supernatants". QIAamp® Viral RNA Mini Kit Handbook, QIAGEN, Jan. 1999, Cat #52906, pp. 1-35.
"Frontiers closing to mystery disease pigs". Animal Pharm., No. 228, May 24, 1991, p. 2.

"Revision of the taxonomy of the Coronavirus, Torovirus, and Arterivirus genera". Archives of Virology, vol. 135, 1994, pp. 227-239.
Abstract in English of CN1458167, dated Nov. 26, 2003.
Abstracts of Papers Presented at the 71st Annual Meeting of the Conference of Research Workers in Animal Disease, Nos. 1-6, Nov. 5-6, 1990, 2 pages.
Albina et al., "An Experimental Model for Post-weaning Multisystenic Wasting Syndrome (PMWS) in Growing Piglets". 2001, Journal of Comparative Pathology, vol. 123, pp. 292-303.
Albina et al., "Immune responses in pigs infected with porcine reproductive and respiratory syndrome virus (PRRSV)". Veterinary Immunology and Immunopathology, vol. 61, 1998, pp. 49-66.
Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.
Allan et al., "Letters, Immunostiulations, PCV-2 and PMWS", The Vet. Records, Aug. 5, 2000, pp. 170-171.
Allan et al., "Passive Transfer of Maternal Antibodies to PCV2 Protects Against Development of Post-weaning Multisystemic Wasting Syndrome (PMWS): Experiemental Infections and a Field Study". 2002, The Pig Journal, vol. 50, pp. 59-67.
Allan et al., "PMWS/PCVD: Diagnosis, Disease, and Control: What do we know?" 2006, Proceedings of the 19th IPVS Congress, Copenhagen, Denmark, vol. 1, pp. 1-9.
Allan et al., "Porcine Circoviruses; A Review", J. Vet., Diagn. Invest. 2000, 12, pp. 3-14.
Allan et al., "Reproduction of postweaning multisystemic wasting syndrome in pigs experimentally inoculated with a Swedish porcine circovirus 2 isolate". 2003, Journal of Veterinary Diagnostic Investigation, vol. 15, pp. 553-560.
Allan et al., Guest Editorial, "PCV-2 Infection in Swine; More Than Just Postweaning Multisystemic Wasting Syndrome", The Vet Journ., 2003, 166, pp. 222-223.
Allende et al., "Mutations in the genome of porcine reproductive and respiratory syndrome virus responsible for the attenuated phenotype". Archives of Virology, vol. 145, No. 6, Jun. 2000, pp. 1149-1161.
Allende et al., "North American and European porcine reproductive and respiratory syndrome viruses differ in non-structural protein coding regions". Journal of General Virology, vol. 80, 1999, pp. 307-315.
Allende et al., "Porcine Reproductive and Respiratory Syndrome Virus: Description of Persistence in Individual Pigs upon Experimental Infection†". Journal of Virology, vol. 74, No. 22, Nov. 2000, pp. 10834-10837.
Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.
Ansari et al., "Influence of N-Linked Glycosylation of Porcine Reproductive and Respiratory Syndrome Virus GP5 on Virus Infectivity, Antigenicity, and Ability to Induce Neutralizing Antibodies." Journal of Virology, vol. 80, No. 8, Apr. 2006, pp. 3994-4004.
Backstrom et al., "Respiratory Diseases of Swine". Veterinary Clinics of North America: Large Animal Practice, vol. 4, No. 2, Nov. 1982, pp. 259-276.
Barfoed et al., "DNA vaccination of pigs with open reading frame 1-7 of PRRS virus". Vaccine, vol. 22, 2004, pp. 3628-3641.
Bautista et al., "Comparison of Porcine Alveolar Macrophages and CL 2621 for the Detection of Porcine Reproductive and Respiratory Syndrome (PRRS) Virus and Anti-PRRS Antibody". Journal of Veterinary Diagnostic Investigation, vol. 5, No. 2, Apr. 1993, pp. 163-165.
Bautista et al., "Serologic Survey for Lelystad and VF-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.
Benfield et al., "Characterization of swine infertility and respiratory syndrome (SIRS) virus (isolate ATCC VR-2332)". Journal of Veterinary Diagnostic Investigation, vol. 4, 1992, pp. 127-133.

(56) References Cited

OTHER PUBLICATIONS

Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.
Benfield et al., "Properties of Sirs Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-21.
Beura et al., "Porcine Reproductive and Respiratory Syndrome Virus Nonstructural Protein 1β Modulates Host Innate Immune Response by Antagonizing IRF3 Activation". Journal of Virology, Volo. 84, No. 3, Feb. 2010, pp. 1574-1584.
Bilodeau et al., "Porcine Reproductive and Respiratory Syndrome in Quebec". The Veterinary Record, Aug. 3, 1991, p. 102.
Blanchard et al., "Protection of swine against post-weaning multisystemic wasting syndrome (PMWS) by porcine circovirus type 2 (PCV2) proteins". Vaccine, vol. 21, 2003, pp. 4565-4575.
Boehringer Ingelheim Vetmedica, Inc., "Data from studies consistent with maintaining safety and efficacy of Ingelvac CircoFLEXâ and Ingelvac MycoFLEXâ vaccines when mixed together and administered concurrently to pigs". Feb. 2008, Technical Bulletion, www.bi-vetmedica.com/swine-research/MycoFLEX-Mycoplasma-immunity_TB2.pdf; 14 pages.
Boehringer Ingelheim Vetmedica, Inc., Ingelvacâ Circoflexâ Material Safety Data Sheet, Online Oct. 2006, pp. 1-10, URL:http://bi-vetmedica.com/sites/default/files/ingelvac-circoflex-msds.pdf.
Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.
Boisseson et al., "Molecular characterization of Porcine circovirus type 2 isolates from post-weaning multisystemic wasting syndrome-affected and non-affected pigs". 2004, Journal of General Virology, vol. 85, pp. 293-304.
Bolin et al., "Postweaning multisystemic wasting syndrome induced after experimental inoculation of cesarean-derived, colostrum-deprived piglets with type 2 porcine circovirus". 2001, Journal of Veterinary Diagnostice Investigation, vol. 13, pp. 185-194.
Bramel-Verheije et al., "Expression of a Foreign Epitope by Porcine Reproductive and Respiratory Syndrome Virus". Virology, vol. 278, 2000, pp. 380-389.
Buddaert et al., "In Vivo and In Vitro Interferon (IFN) Studies with the Porcine Reproductive and Respiratory Syndrome Virus (PRRSV)". Coronaviruses and Arteriviruses: Advances in Experimental Medicine and Biology, vol. 440, Plenum Press, New York, 1998, pp. 461-467.
Cano et al., "Impact of a modified-live porcine reproductive and respiratory syndrome virus vaccine intervention on a population of pigs infected with a heterologous isolate". Vaccine, vol. 25, 2007, pp. 4382-4391.
Caprioli et al., "PCR detection of porcine circovirus type 2 (PCV2) DNA in blood, tonsillar and faecal swabs from experimentally infected pigs". Research in Veterinary Sciences, vol. 81, No. 2, Oct. 2006, pp. 287-292.
Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.
Chae, C. "A review of porcine circovirus 2-associated syndromes and diseases". The Veterinary Journal, vol. 169, No. 3, 2005, pp. 326-336.
Chae, C., "Postweaning multisystemic wasting syndrome: a review of aetiology, diagnosis and pathology". 2004, The Veterinary Journal, vol. 168, pp. 41-49.
Chang et al., "Evolution of Porcine Reproductive and Respiratory Syndrome Virus during Sequential Passages in Pigs". Journal of Virology, vol. 76, No. 10, May 2002, pp. 4750-4763.
Charbonneau, G., "Canadian Experiences with Porcine Circovirus Associated Disease". 2007, Iowa Pork Congress; 30 pages.

Chen et al., "Determination of the 5' end of the lactate dehydrogenase-elevating virus genome by two independent approaches". Journal of General Virology, vol. 75, 1994, pp. 925-930.
Cheung et al., "Kinetics of Porcine Circovirus Type 2 Replication". Archives of Virology, vol. 147, 2002, pp. 43-58.
Chiou, et al., "The Effect of Porcine Circovirus Infection on the Immune Response of Pigs After Vaccination Against Classical Swine Fever and Pseudorabies". 2006, Proceedings of the 19th IPVS Congress, Copenhagen, Denmark, p. 79.
Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.
Christianson et al., "Experimental reproduction of swine infertility and respiratory syndrome in pregnant sows". American Journal of Veterinary Research, vol. 53, No. 4, Apr. 1992, pp. 485-488.
Christianson et al., "Porcine reproductive and respiratory syndrome: A review"., Journal of Swine Health and Production, vol. 2, No. 2, Mar. and Apr. 1994, pp. 10-28.
Christianson et al., "Swine Infertility and Respiratory Syndrome". Pig Veterinary Journal, vol. 27, No. 9, Apr. 1991, pp. 9-12.
Collins et al., "Isolation of swine infertility and respiratory syndrome virus (isolate ATCC VR-2332) in North America and experimental reproduction of the disease in gnotobiotic pigs". Journal of Veterinary Diagnostic Investigation, vol. 4, 1992, pp. 117-126.
Collins et al., "Respiratory Disease in a Swine Herd Experiencing a Reproductive Failure Syndrome". Minnesota Swine Conference for Veterinarians, Sep. 16-18, 1990, pp. 206-207.
Collins et al., "Swine Diagnostic Pathology". Allen D. Leman Swine Conference, College of Veterinary Medicine, University of Minnesota, Sep. 18-22, 1998, pp. 1-4.
Collins et al., "Swine Infertility and Respiratory Syndrome (Mystery Swine Disease)". Minnesota Swine Conference for Veterinarians, St. Paul, MN, Sep. 15-17, 1991, pp. 200-205.
Collins, J.E., "Newly Recognized Respiratory Syndromes in North American Swine Herds". American Association of Swine Practitioners Newsletter, vol. 3, No. 7, Sep.-Oct. 1991, pp. 7, 10-11.
Conzelmann et al., "Molecular Characterization of Porcine Reproductive and Respiratory Syndrome Virus, a Member of the Arterivirus Group". Virology, vol. 193, 1993, pp. 329-339.
Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.
Czermak et al., "Membrane Filtration in Animal Cell Cutlure". 2007, Methods in Biotechnology, vol. 24, pp. 397-420, Humana Press, New Jersey, USA.
Darwich et al., "Cytokine profiles of peripheral blood mononuclear cells from pigs with postweaning multisystemic wasting syndrome in response to mitogen, superantigen or recall viral antigens". 2003, Journal of General Virology, vol. 84, pp. 3453-3457.
Darwich et al., "Genetic and immunobiological diversities of porcine reproductive and respiratory syndrome genotype I strains". Veterinary Microbiology, vol. 150, 2011, pp. 49-62.
Dawson et al., "Studies of the field efficacy and safety of a single-dose Mycoplasma hyopneumoniae vaccine for pigs". Veterinary Record, vol. 151, 2002, pp. 535-538.
Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.
Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.
Drew et al., "Production, characterization and reactivity of monoclonal antibodies to porcine reproductive and respiratory syndrome virus". Journal of General Virology, vol. 76, 1995, pp. 1361-1369.
Drew, T., "Porcine Reproductive and Respiratory Syndrome Virus: A Review". Apr. 1996, 3 pages.

(56) References Cited

OTHER PUBLICATIONS

Duran et al. "Recombinant Baculovirus Vaccines Against Porcine Reproductive and Respiratory Syndrome (PRRS)". Abstracts PRRS, Aug. 9th to 10th, 1995, Copenhagen, Denmark, 2 pages.
Ellis et al., "Porcine circovirus-2 and concurrent infections in the field". Veterinary Microbiology, vol. 98, No. 2, Feb. 2004, pp. 159-163.
Ellis, R.W., "New Technologies for Making Vaccines". Vaccines, Chapter 29, Plotkin et al Eds., WB Saunders Company, Philadelphia, PA, 1988, pp. 568-575.
Fachinger et al., "The effect of vaccination against porcine circovirus type 2 in pigs suffering from porcine respiratory disease complex". 2008, Vaccine, vol. 26, pp. 1488-1499.
Fan et al., "Immunogenicity of Empty Capsids of Porcine Circovirus Type 2 Produced in Insect Cells". 2007, Veterinary Research Communications, vol. 31, pp. 487-496.
Fenaux et al., "A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Imunity Against PCV2 Infection in Pigs", J. Virol, Jun. 2004, vol. 78, No. 12, pp. 6297-6303.
Gagrcin et al., "Complex of Swine Respiratory Diseases-Strategy of control in light of latest knowledge". Veterinarski Glasnik, vol. 58, No. 7-8, 2004, pp. 409-418.
Gao et al., "Genomic characterization of two Chinese isolates of Porcine respiratory and reproductive syndrome virus*'". Archives of Virology, vol. 149, 2004, pp. 1341-1351.
Genbank Accession No. AAC61738, Version AAC61738.1 GI:3661517, Sep. 29, 1998.
Genbank Accession# AAF87231, PCV2 ORF2 Protein, 2000.
Groner, et al., The Biology of Baculoviruses, vol. 1, Biological Properties and Molecular Biology, 1986, Chapter 9, Specificity and Safety of Baculoviruses, pp. 177-202.
Hofmann et al., "Propagation of the virus of porcine epidemic diarrhea in cell culture". Journal of Clinical Microbiology, vol. 26, No. 11, Nov. 1988, pp. 2235-2239.
Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.
International Search Report and Written Opinion for PCT/US2010/047654 mailed May 6, 2011.
Kamstrup, et al., "Immunisation against PCV2 structural protein by DNA vaccination of mice". 2004, Vaccine, vol. 22, pp. 1358-1361.
Kim et al., "Association of Porcine Circovirus 2 with Porcine Respiratory Disese Complex", The Vet. Jour., 2003, 166, pp. 251-256.
Kim et al., "Characterization of the Recombinant Proteins of Porcine Circovirus Type2 Field Isolate Expressed in the Baculovirus System". 2002, Journal of Veterinary Science, vol. 3, No. 1, pp. 19-23.
Kimman et al., "Challenges for porcine reproductive and respiratory syndrome virus (PRRSV) vaccinology". Vaccine, vol. 27, No. 28, Jun. 2009, pp. 3704-3718.
Klinge et al, "Age-dependent resistance to Porcine reproductive and respiratory syndrome virus replication in swine". Virology Journal, vol. 6, No. 177, Oct. 2009.
Klinge et al., "PRRSV replication and subsequent immune responses in swine of various ages". Abstract of Poster No. 56, International Porcine Reproductive and Respiratory Syndrome (PRRS) Symposium, PRRS and PRRSV-Related Diseases: Prevention and Control Strategies, Chicago, IL, Nov. 30-Dec. 1, 2007.
Kost, et al., "Recombinant baculoviruses as mammalian cell gene-delivery vectors". Apr. 2002, Trends in Biotechnology, vol. 20, No. 4, pp. 173-180.
Leitner et al., "DNA and RNA-based vaccines: principles, progress and prospects". Vaccine, vol. 18, 2000, pp. 765-777.

Lv et al., "An infectious cDNA clone of a highly pathogenic porcine reproductive and respiratory syndrome virus variant associated with porcine high fever syndrome". Journal of General Virology, vol. 89, 2008, pp. 2075-2079.
Maes et al., "Effect of vaccination against Mycoplasma hyopneumoniae in pig herds with an all-in/all-out production system". Vaccine, vol. 17, 1999, pp. 1024-1034.
Maranga et al., "Virus-Like Particle Production at Low Multiplicities of Infection With the Baculovirus Insect Cell System". Aug. 2003, Biotechnology and Bioengineering, vol. 84, No. 2, pp. 246-253.
Meng, X.J., "Heterogeneity of porcine reproductive and respiratory syndrome virus: implications for current vaccine efficacy and future vaccine development". Veterinary Microbiology, vol. 74, 2000, pp. 309-329.
Montagnon, B.J., "Polio and rabies vaccines produced in continuous cell lines: a reality for Vero cell line". Dev Biol Stand., vol. 70, 1989, pp. 27-47.
Morris et al., "Promoter Influence on Baculovirus-Mediated Gene jExpression in Permissive and Nonpermissive Insect Cell Lines", J. Virol., Dec. 1992, vol. 66, No. 12, pp. 7397-7405.
Nielsen et al., "Generation of an Infectious Clone of VR-2332, a Highly Virulent North American-Type Isolate of Porcine Reproductive and Respiratory Syndrome Virus". Journal of Virology, vol. 77, No. 6, Mar. 2003, pp. 3702-3711.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Derivation of porcine circovirus type 2-negative pigs from positive breeding herds". Journal of Swine Health and Production, vol. 12, No. 4, Jul. and Aug. 2004, pp. 186-191.
Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.
Rueda et al., "Effect of Different Baculovirus Inactivation Procedures on the Integrity and Immunogenicity of Porcine Parvovirus-Like Particles", Vaccine, 2001, 19, pp. 726-734.
Riggs et al., "Protective Monoclonal Antibody Defines a Circumsporozoite-Like Glycoprotein Exoantigen of Cryptosporidium parvum Sporozoites and Merozoites". The Journal of Immunology, vol. 158, 1997, pp. 1787-1795.
Todd et al., "Development of an adjuvant-active nonionic block copolymer for use in oil-free subunit vaccines formulations". Vaccine, vol. 15, No. 5, 1997, pp. 564-570.
Ulmer et al., "Enhancement of DNA vaccine potency using conventional aluminum adjuvants". Vaccine, vol. 18, 2000, pp. 18-28.
Welch et al., "Construction and evaluation of genetically engineered replication-defective porcine reproductive and respiratory syndrome virus vaccine candidates". Veterinary Immunology and Immunopathology, vol. 102, 2004, pp. 277-290.
Chen et al., "Synthetic B- and T-cell epitope peptides of porcine reproductive and respiratory syndrome virus with Gp96 as adjuvant induced humoral and cell-mediated immunity". Vaccine, vol. 31, 2013, pp. 1838-1847.
Fenaux et al., "Immunogenicity and Pathogenicity of Chimeric Infectious DNA Clones of Pathogenic Porcine Circovirus Type 2 (PCV2) and Nonpathogenic PCV1 in Weanling Pigs". Journal of Virology, vol. 77, No. 20, Oct. 2003, pp. 11232-11243.
Fox et al., "Maximizing Interferon-g Production by Chinese Hamster Ovary Cells Through Temperature Shift Optimization: Experimental and Modeling". Biotechnology and Bioengineering, vol. 85, No. 2, Jan. 20, 2004, pp. 177-184.
Greiner et al., "Quantitative Effect of Porcine Reproductive Respiratory Syndrome Virus on Pig Growth and Immune Response". ,1999, Swine Research Report, Paper 5, 1998, 4 pages.
Lauck et al., "Novel, Divergent Simian Hemorrhagic Fever Viruses in a Wild Ugandan Red Colobus Monkey Discovered Using Direct Pyrosequencing". PLoS ONE, vol. 6, No. 4, e19056, Apr. 2011, pp. 1-6.

(56) References Cited

OTHER PUBLICATIONS

Li et al., "Emergency vaccination alleviates highly pathogenic porcine reproductive and respiratory syndrome virus infection after contact exposure". BMC Veterinary Research, vol. 9, No. 26, 2013, pp. 1-6.
Liesner et al., "Efficacy of Ingelvac® PRRS MLV against highly pathogenic PRRSV: a summary of three challenge trials". Virology & Viral Diseases-PRRS, 22nd International Pig Veterinary Society Congress, Korea, 2012, p. 958.
Mardassi et al., "Structural Gene Analysis of a Quebec Reference Strain of Porcine Reproductive and Respiratory Syndrome Virus (PRRSV)". Corona- and Related Viruses, Edited by P.J. Talbot and G.A. Levy, Plenum Press, New York, 1995, pp. 277-281.
Meuwly et al., "Use of glucose consumption rate (GCR) as a tool to monitor and control animal cell production processes in packed-bed bioreactors". Journal of Biotechnology, vol. 122, 2006, pp. 122-129.
Namdev et al., "Assessing a Disposable Bioreactor for Attachment-Dependent Cell Cultures". Wave Biotech, 2000, 4 pages.
Poljak et al., "Spread of porcine circovirus associated disease (PCVAD) in Ontario (Canada) swine herds: Part I. Exploratory spatial analysis". BMC Veterinary Research, vol. 6, No. 59, 2010, pp. 1-15.
Poppe et al., "Salmonella typhimurium DT104: A virulent and drug-resistant pathogen". Canadian Veterinary Journal, vol. 39, 1998, pp. 559-565.
Rourou et al., "A microcarrier cell culture process for propagating rabies virus in Vero cells grown in a stirred bioreactor under fully animal component free conditions". Vaccine, vol. 25, 2007, pp. 3879-3889.
Slivac et al., "Aujeszky's disease virus production in disposable bioreactor". Journal of Biosciences, vol. 31, No. 3, Sep. 2006, pp. 363-368.
Smith et al., "Observations on Experimental Oral Infection with *Salmonella dublin* in Calves and *Salmonella choleraesuis* in Pigs". Journal of Pathology and Bacteriology, vol. 93, No. 1, 1967, pp. 141-156.
Srcek et al., "BHK 21 C13 cells for Aujeszky's disease virus production using the multiple harvest process". Cytotechnology, vol. 45, 2004, pp. 101-106.
Tian et al., "An attenuated live vaccine based on highly pathogenic porcine reproductive and respiratory syndrome virus (HP-PRRSV) protects piglets against HP-PRRS". Veterinary Microbiology, vol. 138, 2009. pp. 34-40.
Tiscornia et al., "Production and purification of lentiviral vectors". Nature Protocols, vol. 1, No. 1, 2006, pp. 241-245.
Tree et al., "Comparison of large-scale mammalian cell culture systems with egg culture for the production of influenza virus a vaccine strains". Vaccine, vol. 19, 2001, pp. 3444-3450.
Wang et al., "Immune responses in piglets infected with highly pathogenic porcine reproductive and respiratory syndrome virus". Veterinary Immunology and Immunopathology, vol. 142, 2011, pp. 170-178.
Yu et al., "Genomic Sequencing Reveals Mutations Potentially Related to the Overattenuation of a Highly Pathogenic Porcine Reproductive and Respiratory Syndrome Virus". Clinical and Vaccine Immunology, vol. 20, No. 4, Apr. 2013, pp. 613-619.
Zhou et al., "The 30-Amino-Acid Deletion in the Nsp2 of highly Pathogenic Porcine Reproductive and Respiratory Syndrome Virus Emerging in China is Not Related to Its Virulence". Journal of Virology, vol. 83, No. 10, May 2009, pp. 5156-5167.
Brockmeier et al., "Genomic sequence and virulence comparison of four Type 2 porcine reproductive and respiratory syndrome virus strains". Virus Research, vol. 169, No. 1, 2012, pp. 212-221.
Charerntantanakul et al., "Porcine reproductive and respiratory syndrome virus vaccines: Immunogenicity, efficacy and safety aspects". World Journal of Virology, vol. 1, No. 1, Feb. 2012, pp. 23-30.

Collins et al., "Laboratory diagnosis of porcine reproductive and respiratory syndrome (PRRS) virus infection". Swine Health and Production, vol. 4, No. 1, Feb. 1996, pp. 33-35.
Database EMBL Accession No. EF488739, "Porcine respiratory and reproductive syndrome virus isolate MN184C, complete genome". Apr. 19, 2007, pp. 1-4.
Database EMBL Accession No. EU759247, "Porcine respiratory and reproductive syndrome virus isolate PRRSV2000000079 envelope glycoprotein gene, complete cds". Aug. 10, 2008, 1 page.
Leng et al., "Evaluation of the Efficacy of an Attenuated Live Vaccine against Highly Pathogenic Porcine Reproductive and Respiratory Syndrome Virus in Young Pigs". Clinical and Vaccine Immunology, vol. 19, No. 8, Aug. 2012, pp. 1199-1206.
UniProt: Accession No. B4ZUF3. "SubName: Full=Envelope glycoprotein". Sep. 23, 2008, 1 page.
UniProt: Accession No. J9QHKO. "SubName: Full=Nucleocapsid protein". Nov. 28, 2012, 1 page.
UniProt: Accession No. J9QI11. "SubName: Full=Unglycosylated membrane protein". Nov. 28, 2012, 1 page.
UniProt: Accession No. J9QIW4. "SubName: Full=Polyprotein lab". Nov. 28, 2012, pp. 1-3.
Fang et al., "A Full-Length cDNA Infectious Clone of North American Type 1 Porcine Reproductive and Respiratory Syndrome Virus: Expression of Green Fluorescent Protein in the Nsp2 Region". Journal of Virology, vol. 80, No. 23, Dec. 2006, pp. 11447-11455.
Huang et al., "Novel strategies and approaches to develop the next generation of vaccines against porcine reproductive and respiratory syndrome virus (PRRSV)". Virus Research, vol. 154, 2010, pp. 141-149.
Thanawongnuwech et al., "Taming PRRSV: Revisiting the control strategies and vaccine design". Virus Research, vol. 154, No. 1-2, 2010, pp. 133-140.
Nam et al. "Complete genomic characterization of a European type 1 porcine reproductive and respiratory syndrome virus isolate in Korea". Archives of Virology, vol. 154, No. 4, 2009, pp. 629-638.
Gagrcin et al., "Complex of Swine Respiratory Diseases-Strategy of control in light of latest knowledge". Veterinarski Glasnik, vol. 58, No. 7-8, 2004, pp. 409-418. [English Abstract at p. 417.].
"Calendar, Mar. 2007". 3rd Annual Pig Veterinary Society Congress, vol. 37, No. 2, 2007, p. 33. [Accessed at http://www.pigintemational-digital.com/pigintemational/2007013//Print . . . on Aug. 3, 2012].
"General Methods 6xHis and GST Purification Direct Cloning". Baculovirus Expression Vector System Manual, 6th Edition, May 1999, pp. 1-108.
"H-V11-Postweaning multisystemic wasting syndrome-Lymph node-Pig". Read-Only Case Details Reviews: Mar. 2009, pp. 1-4. [Accessed at http://www.askjpc.org/vspo/show_page.php?id=800 on Dec. 14, 2013].
Allan et al., "PCV2; ticking time bomb?" Pig Progress, vol. 18, No. 5, 2002, pp. 14-12.
Bahnemann, Hans G., "Inactivation of Viruses in Serum with Binary Ethyleneimine". Journal of Clinical Microbiology, vol. 3, No. 2, Feb. 1976, pp. 209-210.
Banholzer, E "A Follow-Up: PCV2, PRRS, Mycoplasma hyopneumoniae, Improvac". IPVS Congress, Jul. 16-19, ' 2006, pp. 1-20.
Begue et al., "Future Combined Vaccines". Journal of Infectious Diseases, vol. 173, Supp 3, 1996, pp. S295-S297.
Belikov, V.G., "Connection between the molecular structure of substances and their action on organisms". Pharmaceutical Chemistry, vol. 1, Section 2.2, 1993, p. 43.
Beseme et al., "Vaccination strategies for the control of circoviral diseases in pigs: PMWS and PCV2-associated PRDC". Proceedings of the Japanese Pig Veterinary Society, vol. 49, 2006, pp. 15-38.
Blanchard et al., "An ORF2 protein-based ELISA for porcine circovirus type 2 antibodies in post-weaning multisystemic wasting syndrome". Veterinary Microbiology, vol. 94, 2003, pp. 183-194.
Chung et al., "Real-time PCR for quantitation of porcine reproductive and respiratory syndrome virus and porcine circovirus type 2 in naturally-infected and challenged pigs". Journal of Virological Methods , vol. 124, 2005, pp. 11-19.

(56) References Cited

OTHER PUBLICATIONS

Eichmeyer et al., "Efficacy evaluation of a Mycoplasma hyopneumoniae bacterin in a mixture with a porcine aircovirus type 2 vaccine". Allen D. Leman Swine Conference-Recent Research Reports, 2008, pp. 28.
Ellis, John A., "Porcine circovirus: An old virus in a new guise causes an emerging disease thorugh a novel pathogenesis". Large Animal Veterinary Rounds, vol. 3, No. 4, Apr. 2003, pp. 1-6.
Fan et al., "Preclinical study of influenza virus A M2 peptide conjugate vaccines in mice, ferrets, and rhesus monkeys". Vaccine, vol. 22, 2004, pp. 2993-3003.
Fan et al., "The Expression of Porcine Circovirus Type 2 ORF2 Gene in Insect Cells and its Character". Chinese Journal of Biotechnology, vol. 21, No. 6, Nov. 2005, pp. 975-978.
Fenaux et al., "Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay to Detect and Differentiate between Infections with PCV-1 and PCV-2". Journal of Clinical Microbiology, vol. 38, No. 7, Jul. 2000, pp. 2494-2503.
Fort et al., "Porcine circovirus type 2 (PCV2) vaccination of conventional pigs prevents viremia against PCV2 solates of different genotypes and geographic origins". Vaccine, vol. 26, No. 8, 2008, pp. 1063-1071.
Gabrielian et al., Practical Chemistry, Akademia, Ed. 2, 2013, p. 10, Paragraph 2, p. 283.
GenBank Accession No. AF201311, Direct Submission, submitted Feb. 23, 2000 in Mankertz et al., "Characterization of PCV-2 isolates from Spain, Germany and France", Virus Research, vol. 66, No. 1, 2000, pp. 65-77, 2 pages.
Gizurarson, Sveinbjörn, "Clinically Relevant Vaccine-Vaccine Interactions". BioDrugs, vol. 9, No. 6, Jun. 1998, pp. 443-453.
Gualandi et al., "The Ability by Different Preparations of Porcine Parvovirus to Enhance Humoral Immunity in Swine and Guinea Pigs". Microbiologica, vol. 11, No. 4, 1988, pp. 363-369.
Gualandi et al., "The Response of Pregnant Gilts Previously Given an Inactivated Preparation of Porcine Parvovirus (PPV) to Challenge Infection with a Fully Virulent Ppv". Microbiologica, vol. 15, 1992, pp. 391-396.
Gupta et al., "Adjuvants for human vaccines-current status, problems and future prospects". Vaccine, vol. 13, No. 14, 1995, pp. 1263-1276.
Haake et al., "Influence of age on the effectiveness of PCV2 vaccination in piglets with high levels of maternally derived antibodies". Veterinary Microbiology, vol. 168, 2014, pp. 272-280.
Hamel et al., "Nucleotide Sequence of Porcine Circovirus Associated with Postweaning Multisystemic Wasting Syndrome in Pigs". Journal of Virology, vol. 72, No. 6, Jun. 1998, pp. 5262-5267.
Harding et al., "Recognizing and diagnosing postweaning multisystemic wasting syndrome (PMWS)". Swine Health and Production, vol. 5, No. 5, 1997, pp. 201-203.
Haruna et al., "The role of immunostimulation in the development of postweaning multisystemic wasting syndrome in pigs under field conditions". Canadian Journal of Veterinary Research, vol. 70, Oct. 2006, pp. 269-276.
Hilgers et al., "Alkyl-esters of polyacrylic acid as vaccine adjuvants". Vaccine, vol. 16, No. 16, 1998, pp. 1575-1581.
Hirai et al., "Dual infection with PCV-2 and porcine epidemic diarrhoea virus in neonatal piglets". The Veterinary Record, vol. 148, 2001, pp. 482-484.
Hoogland et al., "Effects of adjuvants on porcine circovirus type 2-associated lesions". Journal of Swine Health and Production, vol. 14, No. 3, 2006, pp. 133-139.
Hüser et al., "Baculovirus Vectors: Novel Mammalian Cell Gene-Delivery Vehicles and Their Applications". American Journal of Pharmacogenomics, vol. 3, No. 1, 2003, pp. 53-63.
Invitrogen Life Technologies, "Growth and Maintenance of Insect Cell Lines". Insect Cell Lines Manual, Version K, Jul. 12, 2002, pp. 1-34. [Accessed at http://www.med.unc.edu/pharm/sondeklab/Lab% 20Resources/manuals/insect_cell_manual.pdf on Nov. 25, 2013].
Jiang et al., "Expression, Self-Assembly, and Antigenicity of the Norwalk Virus Capsid Protein". Journal of Virology, vol. 66, No. 11, Nov. 1992, pp. 6527-6532.
Jiang et al., "Synthesis of rotavirus-Like Particles in Insect Cells: Comparative and Quantitative Analysis". 3iotechnology and Bio-engineering, vol. 60, No. 3, 1998, pp. 369-374.
Kennedy et al., "Repdocution of Lesions of Postweaning Multisystemic Wasting Syndrome by Infection of Conventional Pigs with Porcine Circovirus Type 2 Alone or in a Combination with Porcine Parvovirus". Journal of Comparative Pathology, vol. 122, 2000, pp. 9-24.
Kiupel, M. "Postweaning Multisystemic Wasting Syndrome (PMWS) in pigs". Production diseases in Farm Animals, 12th International Conference, Section D, Wageningen Academic Publishers, The Netherlands, 2006, pp. 74-89.
Kovacs et al., "The live attenuated bovine viral diarrhea virus components of a multi-valent vaccine confer protection against fetal infection". Veterinary Microbiology, vol. 96, 2003, pp. 117-131.
Kyriazakis et al., "The Maintenance of Health". Whittemore's Science and Practice of Pig Production, Third Edition, Chapter 7, Blackwell Publishing Ltd., Oxford, UK, 2006, pp. 263-316.
Lekcharoensuk et al., "Epitope Mapping of the Major Capsid Protein of Type 2 Porcine Circovirus (PCV2) by Using Chimeric PCV1 and PCV2". Journal of Virology, vol. 78, No. 15, Aug. 2004, pp. 8135-8145.
Li et al., "Expression and Self-Assembly of Empty Virus-Like Particle of Hepatitis E Virus". Journal of Virology, vol. 71, No. 10, Oct. 1997, pp. 7207-7213.
Liu et al., "Development of an ELISA Based on the Baculovirus-Expressed Capsid Protein of Porcine Circovirus Type 2 as Antigen". Journal of Veterinary Medical Science, vol. 66, No. 3, 2004, pp. 237-242.
Mashkovski, M.D., "Interaction of Drugs". Medicaments, A Doctor's Manual, 14th Edition, vol. 1, Section 9, Moscow, 2001, p. 11.
McKeown et al., "Effects of Porcine Circovirus Type 2 (PCV2) Maternal Antibodies on Experimental Infection of Piglets with PCV2". Clinical and Diagnostic Laboratory Immunology, vol. 12, No. 11, Nov. 2005, pp. 1347-1351.
Meehan et al., "Characterization of novel circovirus DNAs associated with wasting syndromes in pigs". Journal of General Virology, vol. 79, 1998, pp. 2171-2179.
Mortola et al., "Efficient assembly and release of SARS coronavirus-like particles by a heterologous expression system". FEBS Letters, vol. 576, 2004, pp. 174-178.
Muirhead, Mike, "Sources of information on PMWS/PDNS". The Veterinary Record, vol. 150, No. 14, Apr. 6, 2002, p. 456.
Murakami et al., "Occurrence of Swine Salmonellosis in Postweaning Multisystemic Wasting Syndrome (PMWS) Affected Pigs Concurrently Infected with Porcine Reproduction and Respiratory Syndrome Virus (PRRSV)". Journal of Veterinary Medical Science, vol. 68, 2006, pp. 387-391.
Neutra et al., "Optimization of protein-production by the baculovirus expression vector system in shake flasks". Applied Microbiology and Biotechnology Journal, vol. 37, No. 1, 1992, pp. 74-78.
Noad et al., "Virus-like particles as immunogens" Trends in Microbiology, vol. 11, No. 9, Sep. 2003, pp. 438-444.
Oh et al., "Evaluation of Two Different Vaccine Program Against M. Hyopneumniae on an 1100 Sow Farm in Korea". Asian Pig Veterinary Society Congress, Sep. 2013, 1 page.
Ohnesorge et al., "Efficacy Studies—Efficacy evaluation of a mixed Mycoplasma hyopneumoniae bacterin and a porcine circovirus type 2 vaccine". 2007, 1 page. [Accessed at http://www.ingelvacflex.co.uk/mycoflex/research/efficacy.php on Jul. 31, 2012].
Opriessnig et al., "Differences in virulence among porcine circovirus type 2 isolates are unrelated to cluster type 2a or 2b and prior infection provides heterologous protection". Journal of General Virology, vol. 89, No. 10, 2008, pp. 2482-2491.

(56) References Cited

OTHER PUBLICATIONS

Opriessnig et al., "Effect of porcine circovirus type 2 (PCV2) vaccination on porcine reproductive and respiratory syndrome virus (PRRSV) and PCV2 coinfection". Veterinary Microbiology, vol. 131, 2008, pp. 103-114.

Dpriessnig et aL, "Effect of porcine parvovirus vaccination on the development of PMWS in segregated early weaned pigs coinfected with type 2 porcine circovirus and porcine parvovirus". Veterinary Microbiology, vol. 98, 2004, pp. 209-220.

Opriessnig et al., "Effects of the timing of the administration of Mycoplasma hyopneumoniae bacterin on the development of lesions associated with porcine circovirus type 2". Veterinary Record, vol. 158, No. 5, Feb. 2006, pp. 149-154.

Opriessnig et al., "Experimental Co-Infection with Porcine Circovirus Type 2 and *Salmonella typhimurium* or Lawsonia Intracellularis". Pig Progress, Jun. 2008, 1 page. [Accessed at: http://www.pigprogress.net/public/file/IPVS-oral%20presentations/Viral%20diseases/Experimental%20co-infection%20with%20PCV2%20and%20salmonella%20Typhimurium%20or%20lawsonia%20intracellularis.pdf on Mar. 17, 2010].

Paterson, J.E., "Health and antimicrobial resistance". Manipulating Pig Production X, Chapter 2, Proceedings of the Tenth Biennial Conference of the Australasian Pig Science Association (Inc.) (APSA) held in Christchurch, New Zealand on Nov. 27 to 30, 2005, Werribee, Victoria, Australia: Australasian Pig Association (Inc.), pp. 21-74.

Patterson et al., "Baculovirus and Insect Cell Gene Expression: Review of Baculovirus Biotechnology". Environmental Health Perspectives, vol. 103, Nos. 7-8, Jul.-Aug. 1995, pp. 756-759.

Pokrovsky, V.I., Antigens. Small Encyclopaedia of Medicine, vol. 1, Moscow, Sovetskaja Enciklopedia, 1998, pp. 138, right column, paragraph 6.

Ragona et al., "The Transcriptional Factor Egr-1 Is Synthesized by Baculovirus-Infected Insect Cells in an Active, DNA-Binding Form". DNA and Cell Biology, vol. 10, No. 1, 1991, pp. 61-66.

Riggs et al., "Efficacy of Monoclonal Antibodies against Defined Antigens for Passive Immunotherapy of Chronic Gastrointestinal Cryptosporidiosis". Antimicrobial Agents and Chemotherapy, vol. 46, No. 2, Feb. 2002, pp. 275-282.

Rodríguez-Arrioja et al., "Dynamics of procine circovirus type 2 infection in a herd of pigs with postweaning multisystemic wasting syndrome". American Journal of Veterinary Research, vol. 63, No. 3, Mar. 2002, pp. 354-357.

Roesler et al., "Oral vaccination of pigs with an invasive gyrA-cpxA-rpoB *Salmonella typhimurium* mutant". Vaccine, vol. 23, No. 5, Dec. 2004, pp. 595-603.

Rotto, Hans "Diagnosis, Vaccination and Field Experiences with PCV-AD". Iowa Pork Progress, 2007, pp. 1-10.

Schaefer et al., "Characterization and Formulation of Multiple Epitope-Specific Neutralizing Monoclonal Antibodies for Passive Immunization against Cryptosporidiosis", Infection and Immunity, vol. 68, No. 5, May 2000, pp. 2608-2616.

Schwartz, Larry, "Diafiltration: A Fast, Efficient Method for Desalting, or Buffer Exchange of Biological Samples". Scientific and Technical Report, PALL Life Sciences, 2003, pp. 1-6. [Retrieved at http://www.pall.com/pdfs/Laboratory/02.0629_Buffer_Exchange_STR.pdf on Sep. 23, 2014].

Sedlik et al., "Recombinanat parvovirus-like particles as an antigen carrier: A novel nonreplicative exogenous antigen to elicit protective antiviral cytotoxic T cells". Proceedings of the National Academy of Sciences, vol. 94, Jul. 1997, pp. 7503-7508.

Segales et al., "Pathological findings associated with naturally acquired porcine circovirus type 2 associated lisease". Veterinary Microbiology, vol. 98, 2004, pp. 137-149.

Segalés et al., "Immunosuppression in postweaning multisystemic wasting syndrome affected pigs". Veterinary Microbiology, vol. 98, 2004, pp. 151-158.

Segalés et al., "Porcine Circovirus Diseases". Diseases of Swine, 9th Edition, Chapter 14, Blackwell Publishing, Ames, Iowa, 2006, pp. 299-307.

Spier, R.E., "Multivalent Vaccines: Prospects and Challenges". Folia Microbiologica, vol. 42, No. 2, 1997, pp. 105-112.

Suradhat et al., "The influence of maternal immunity on the efficacy of a classical swine fever vaccine against alassical swine fever virus, genogroup 2.2, infection". Veterinary Microbiology, vol. 92, 2003, pp. 187-194.

Thacker et al., "Effect of vaccination on the potentiation of porcine reproductive and respiratory syndrom virus (PRRSV)-induced pneumonia by Mycoplama hyopneumoniae". Vaccine, vol. 18, 2000, pp. 1244-1252.

Thacker, Eileen L., "Diagnosis of Mycoplama hyopneumoniae". Journal of Swine Health Production, vol. 12, No. 5, 2004, pp. 252-254.

Truong et al., "Identification of an immunorelevant ORF2 epitope from porcine circovirus type 2 as a serological marker for experimental and natural infection". Archives of Virology, vol. 146, 2001, pp. 1197-1211.

UniProt Database Accession No. O91862 submitted Nov. 1, 1998 by Meehan et al., Characterization of novel circovirus DNAs associated iwth wasting sydromes in pigs. Journal of General Virology, 1998; 79: 2171-2179, 1 page.

UniProt Database Accession No. Q9YTB6, Direct Submission, Wang et al., May 1, 1999 , 1 page.

Wan et al., "Comprehensive Prevention and Control Techniques for Porcine Circovirus Type 2 Infection" Chinese Swine Industry, No. 3, 2006, pp. 42-45.

Wang et al., "Construction and immunogenicity of recombinant adenovirus expressing the capsid protein of porcine aircovirus 2 (PCV2) in mice". Vaccine, vol. 24, 2006, pp. 3374-3380.

Weibel, Helen, "A field efficacy study with Enterisol® Ileitis and Ingelvac CircoFLEX® in Switzerland". Universitat Zürich, 2009, 1 page. [Accessed at: http://www.vet.uzh.ch/dissertationen/diss_anzeige.php?ID=724&sprache=e on Jun. 7, 2013].

Williams et al., "Combined vaccines and simultaneous administration: Current issues and perspectives". Annals of the New York Academy of Sciences, vol. 754, 1995, pp. xi-xv, 35-47.

Wu et al., "Replication, Integration, and Packaging of Plasmid DNA following Cotransfection with Baculovirus Viral DNA". Journal of Virology, vol. 73, No. 7, Jul. 1999, pp. 5473-5480.

Xia et al., "Preparation of and Immunity Tests with Canine Coronavirus BEI Inactivated Vaccine". Chinese Journal of Veterinary Medicine, vol. 37, No. 3, 2001, pp. 37-38.

Yamada et al., "Evaluation of the Efficacy of Inactivated Vaccine against *Salmonella enteritidis* Infection in Chicken". Journal of the Japanese Society on Poultry Diseases, vol. 35, No. 1, 1999, pp. 13-21. (English Summary at p. 21).

Yuan et al., "Immunology of the porcine respiratory disease complex". Animal Science Abroad in Pigs and Poultry, No. 5, 2002, pp. 36-38.

Kartashov et al., "Immunohistochemistry of Lymph Nodes in Porcine Circoviral Disease". Veterinarnay Patologiya, No. 4, Fundamental Researches in Veterinary, 2008, pp. 26-31.

Boehringer Ingelheim Vetmedica, Inc., Ingelvacâ CircoFLEX—MycoFLEXä Material Safety Data Sheet, Online Jun. 2008, pp. 1-10. [Accessed at: http://www.bi-vetmedica.com/content/dam/internet/ah/vetmedica/com_EN/MSDS/Ingelvac%20CircoFlex-Mycoglex_msds.pdf on Feb. 12, 2016].

\* cited by examiner

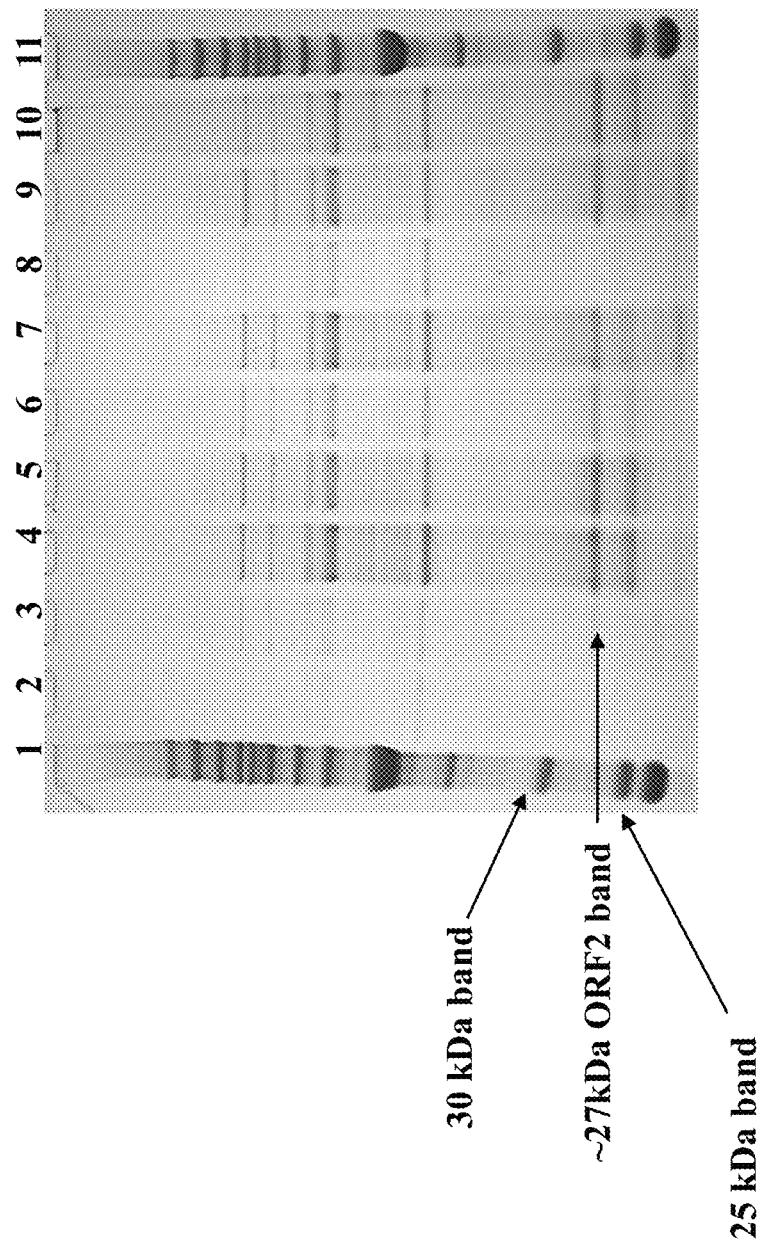

METHODS OF REDUCING VIRUCIDAL ACTIVITY IN PCV-2 COMPOSITIONS AND PCV-2 COMPOSITIONS WITH AN IMPROVED IMMUNOGENICITY

This application relates to and claims priority to U.S. Provisional Patent Application No. 61/309,408, which was filed Mar. 1, 2010, and U.S. Provisional Patent Application No. 61/239,192, which was filed Sep. 2, 2009. All of which are incorporated herein by reference in their entirety. All applications are commonly owned.

SEQUENCE LISTING

The present application includes a sequence listing in accordance with 37 C.F.R. 1.821-1.825. The sequence listing accompanying this application is hereby incorporated by reference in its entirety.

BACKGROUND

Field of Invention

The present invention relates to methods and compositions, for reducing the virucidal activity of compositions that would normally exhibit some degree of virucidal activity. By using the methods of the present invention, the virucidal activity of such compositions can be reduced in comparison to the virucidal activity of a composition that does not include the steps of the present invention. More specifically, the present invention relates to methods for producing antigenic Porcine Circovirus Type II (PCV-2) compositions such that they show relatively little or no virucidal activity as compared to the compositions known in the art using current detection methods, and in particular, as compared to compositions not produced by a method according the present invention. The present invention further relates to a novel immunogenic composition, preferably a PCV-2 containing composition produced according to the method provided by the present patent application, preferably characterized by reduced or no virucidal activity relative to comparable compositions described in the art. According to a further aspect, the present invention also provides immunogenic compositions comprising purified PCV-2 antigen, preferably purified PCV-2 antigen with an improved immunogenicity.

Description of the Prior Art

Porcine circovirus type 2 (PCV-2) is a small (17-22 nm in diameter), icosahedral, non-enveloped DNA virus, which contains a single-stranded circular genome. PCV-2 shares approximately 80% sequence identity with porcine circovirus type 1 (PCV-1). However, in contrast with PCV-1, which is generally non-virulent, swine infected with PCV-2 exhibit a syndrome commonly referred to as Post-weaning Multi-systemic Wasting Syndrome (PMWS). PMWS is clinically characterized by wasting, paleness of the skin, unthriftiness, respiratory distress, diarrhea, icterus, and jaundice. In some affected swine, a combination of all symptoms will be apparent while other swine will only have one or two of these symptoms. During necropsy, microscopic and macroscopic lesions also appear on multiple tissues and organs, with lymphoid organs being the most common site for lesions. A strong correlation has been observed between the amount of PCV-2 nucleic acid or antigen and the severity of microscopic lymphoid lesions. Mortality rates for swine infected with PCV-2 can approach 80%. In addition to PMWS, PCV-2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia.

Several vaccine are available to reduced the impact of PCV-2 infections in pigs. U.S. Pat. No. 6,703,023 provides a DNA based vaccine for the prophylaxis of pigs against PMWS. In WO 03/049703 production of a live chimeric vaccine is described, comprising the non-pathogenic PCV1 virus in which, however, the ORF2 protein is replaced by the ORF2 protein of the pathogenic PCV-2. WO 99/18214 and WO 99/29717 have provided several PCV-2 strains and procedures for the preparation of a killed PVC2 vaccine. Preparation of subunit vaccines have also been described in WO 99/18214 and WO 99/29717. An effective ORF2 based subunit vaccine has been reported in WO 06/072065. A further ORF-2 based subunit vaccine is described also in WO 07/28823. However, none of the vaccine described in the prior art includes a non-virucidal and/or purified PCV-2 antigen, preferably a highly purified PCV-2 ORF2 antigen.

Immunogenic compositions against PCV-2 and various immunogenic compositions against other pathogens often have a virucidal effect on other antigens. Current regulatory standards (9 CFR 113.35) permit some virucidal activity in multivalent compositions, but this virucidal activity cannot result in a loss of more than 0.7 logs/ml of a live virus or less than 0.7 logs/ml CFU of live bacteria when combined with the other components of the immunogenic composition. Compositions that have more virucidal activity than permitted cannot be combined with other antigens to create a multivalent vaccine.

Open reading frame 2 (ORF2) protein of PCV-2, having an approximate molecular weight of 30 kDa when run on SDS-PAGE gel, has been utilized in the past as an antigenic component in vaccines and immunogenic compositions for PCV-2. Typical methods of obtaining ORF2 for use in such vaccines and compositions generally consist of amplifying the PCV-2 DNA coding for ORF2, expressing the ORF2 protein within a host cell, and extracting the ORF2 protein from the host cell via cell lysis. The recovered ORF2 cell lysate is then used as the antigenic portion of an immunogenic composition or vaccine. In some cases the ORF2 containing cell lysate is separated from the cell debris.

What is needed is a method for reducing the virucidal activity of PCV-2-containing immunogenic compositions and antigens therein such that regulatory requirements can be met and efficacious multivalent compositions can be administered. What is further needed are methods for decreasing or reducing the virucidal activity and effect of PCV-2-containing compositions on Porcine Reproductive and Respiratory Syndrome Virus (PRRSV). What is still further needed are immunogenic compositions that have undergone the methods of the present invention such that their virucidal activity has been reduced to acceptable standards and can be combined with other antigens to form multivalent immunogenic compositions.

SUMMARY OF THE INVENTION

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984);

Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like The present invention solves the problems inherent in the prior art and provides a distinct advance in the state of the art. Generally, the present invention provides a method of producing a PCV-2 antigenic composition comprising the steps of i) obtaining a first liquid containing a PCV-2 antigen, and ii) removing at least a portion of the first liquid from the PCV-2 antigen. Preferably the PCV-2 antigen is used as or in the PCV-2 antigenic composition.

For purposes of the present invention, a "first liquid" refers to liquid, aqueous, or fluid media typically used in combination with cells, antigens, immunogenic compositions, vaccines, and the like. Preferably, the first liquid comprises media from an antigenic composition, more preferably, the first liquid comprises or preferably consists of cell culture media used for the production of recombinant proteins in cultivated host cells. The cultivated host cells can be bacteria, yeasts, insect cells, animal cells, and mammalian cells, with insect and mammalian cells being particularly preferred. Thus the first fluid may comprise or consist of media for the cultivation of bacteria, yeast, insect cells, animal cells, or mammalian cells. Preferably, the cell media is serum free cell media, and most preferably the culture media is EX-CELL® 420 serum free media, when insect cells are used. EX-CELL® 420 is a complete medium that is protein-free and contains L-glutamine, and was developed and optimized for the serum-free growth of Sf9 and Sf21 insect cell lines.

A "second liquid", for purposes of the present invention, refers to any liquid normally used in combination with cells, antigen, immunogenic compositions, vaccines, and the like, which is different from the first liquid. Preferably, the second liquid is an aqueous solution, even more preferably a pharmaceutically acceptable solution, and even more preferably a buffer, such as a saline or phosphate buffer and the like. Most preferably, the second fluid is characterized by not being virucidal to any live virus or any live bacteria (herein, unless explicitly stated or apparent from the context the term "virucidal" is inclusive of bactericidal activity), when the live virus or live bacteria is cultivated in or stored in such a fluid.

"Portion", for purposes of the present invention, refers to any amount which does not encompass the entire amount. For example, a portion of liquid would be anything less than 100% of the volume of the liquid, such as 90% of the liquid, 80% of the liquid, 70% of the liquid, and all amounts between more than 0% and less than 100%.

A "PCV-2 antigen" refers to any composition of matter that comprises at least one antigen that can induce, stimulate or enhance the immune response against PCV-2 infection, when administered to an animal, preferably to a pig. Preferably, the PCV-2 antigen is the whole PCV-2 virus, preferably in an inactivated form, a live modified or attenuated PCV-2 virus, a chimeric virus that comprises at least an immunogenic amino acid sequence of PCV-2, or any other polypeptide or component that comprises at least an immunogenic amino acid sequence of PCV-2, preferably ORF2. The terms "immunogenic protein", "immunogenic polypeptide" or "immunogenic amino acid sequence" as used herein refer to any amino acid sequence of PCV-2, which elicits an immune response in a host against PCV-2. Preferably, such immunogenic protein, immunogenic polypeptide or immunogenic amino acid of PCV-2 is any one of those disclosed or provided in the international patent application WO2006/072065 (the contents and teachings of which are hereby incorporated by reference), or is any other PCV-2 polypeptide known in the art. For instance, a representative sequence of PCV-2 ORF2 DNA comprises the nucleotide sequence Genbank Accession No. AF086834 (SEQ ID NO: 3) and SEQ ID NO: 4.

However, it is understood by those of skilled in the art that this sequence could vary by as much as 1-10% in sequence homology and still retain the antigenic characteristics that render it useful in immunogenic compositions. The antigenic characteristics of an immunological composition can be, for example, estimated by the challenge experiment as provided by Example 4 of WO06/072065. Moreover, the antigenic characteristic of a modified antigen is still retained, when the modified antigen confers at least 70%, preferably 80%, more preferably 90% or more of the protective immunity as compared to the PCV-2 ORF2 protein, encoded by the polynucleotide sequence of SEQ ID NO:3 or SEQ ID NO:4 as provided in WO06/072065. Further preferred PCV-2 ORF2 antigens are as follows:

i) a polypeptide comprising the sequence of SEQ ID NO: 5, SEQ ID NO: 6, SEQ ID NO: 9, SEQ ID NO: 10 or SEQ ID NO: 11 of WO06/072065;

ii) any polypeptide that is at least 80% homologous and/or identical to the polypeptide of i), iii) any immunogenic portion of the polypeptides of i) and/or ii)

iv) the immunogenic portion of iii), comprising at least 5, preferably 8, more preferably 10 contiguous amino acids of any of the sequences of SEQ ID NO: 5, SEQ ID NO: 6, SEQ ID NO: 9, SEQ ID NO: 10 or SEQ ID NO: 11 of WO06/072065, v) a polypeptide that is encoded by a DNA comprising the sequence of SEQ ID NO: 3 or SEQ ID NO: 4 of WO06/072065.

vi) any polypeptide that is encoded by a polynucleotide that is at least 80% homologous and/or identical to the polynucleotide of v), vii) any immunogenic portion of the polypeptides encoded by the polynucleotide of v) and/or vi), viii) the immunogenic portion of vii), wherein the polynucleotide coding for the immunogenic portion comprises at least 30 contiguous nucleotides included in the sequences of SEQ ID NO: 3 or SEQ ID NO: 4 of WO06/072065.

The sequence listing of WO06/072065 is identical with the sequence listing attached to this application.

Preferably any of the immunogenic portions described above having the antigenic characteristics of PCV-2 ORF2 antigen that is encoded by the sequence of SEQ ID NO: 3 or SEQ ID NO: 4 of WO06/072065.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions that are not identical differ by conservative amino acid substitutions. However, conservative substitutions are not included as a match when determining sequence identity.

"Live" virus or bacterium, for purposes of the present invention, refers to a virus or bacterium that is capable of replicating in a host. A preferred live virus and a preferred live bacterium of the present invention are the PRRS virus and the *Mycoplasma hyopneumonia* bacterium, respectively. However, the term live virus or live bacterium is not limited to PRRS virus and *Mycoplasma hypneumoniae*, respectively.

The portion of the first liquid can be removed from the PCV-2 antigen by an exchange of the portion of the first liquid against a second liquid, wherein the second liquid is different from the first liquid (see definition of second fluid). Thus according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, wherein the portion of the first liquid is removed from the PCV-2 antigen by an exchange of the portion of the first liquid against a second liquid, and wherein the second liquid is different from the first liquid. Preferably the exchange of the portion of the first liquid with the second liquid comprises the steps of a) adding the second liquid to the first liquid which contains the PCV-2 antigen and b) concentrating the PCV-2 antigen by removing a portion of the first and second liquids from the PCV-2 antigen. Thus according to a further aspect, the present application provides a method of producing a PCV-2 antigenic composition comprising the steps of i) obtaining a first liquid containing a PCV-2 antigen, ii) removing at least a portion of the first liquid from the PCV-2 antigen by an exchange of at least a portion of the first liquid against a second liquid comprising the steps a) adding the second liquid to the first liquid which contains the PCV-2 antigen and b) concentrating the PCV-2 antigen by removing a portion of the first and second liquids from the PCV-2 antigen.

The portion of the first liquid can be removed from the PCV-2 antigen by a filtration step utilizing a filter. However, any other method known to a person skilled in the art can be used to remove the portion of any fluids, including the first and, whenever applicable, a portion of the second fluid from the PCV-2 antigen. Such method, for instance includes but is not limited to centrifugation and/or chromatography. However, filtration is most preferred. A preferred filtration method to remove the portion of the first fluid, or any other fluid, whenever applicable, comprises ultra- and/or dia-filtration. Ultra- and dia-filtration are standard methods known to a person skilled in the art, described for example in detail in *Protein Purification Methods—A Practical Approach*—editors: E. L. V. Harris and S. Angel, Oxford University Press 1995 (the contents and teachings of which are hereby incorporated by reference). In particular, in Chapter 3 of that textbook, several methods and types of equipment are described, all of which can be used by an ordinary person skilled in the art in an exemplary manner for the purpose of the present invention. Thus according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, wherein the portion of the first liquid is removed from the PCV-2 antigen by filtration, preferably by dia- or ultra-filtration. Preferably, the portion of the first liquid is removed from the PCV-2 antigen by an exchange of at least a portion of the first liquid against a second liquid comprising the steps a) adding the second liquid to the first liquid which contains the PCV-2 antigen and b) concentrating the PCV-2 antigen by removing a portion of the first and second liquids from the PCV-2 antigen.

As defined above, a preferred second liquid to be used in any of the methods described is a buffer, preferably a physiologically acceptable buffer with saline being particularly preferred. Thus according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, by an exchange against a buffer, preferably a physiologically acceptable buffer such as saline or phosphate buffer or the like. Preferably the portion of the first liquid is removed from the PCV-2 antigen by filtration, preferably by dia- and/or ultra-filtration. More preferably, the portion the exchange of at least a portion of the first liquid against the buffer, preferably the physiologically acceptable buffer, such as saline or phosphate buffer or the like, comprising the steps a) adding the buffer, preferably the physiologically acceptable buffer, such as saline or phosphate buffer or the like, to the first liquid which contains the PCV-2 antigen and b) concentrating the PCV-2 antigen by removing a portion of the first and the fluid which is a buffer, preferably a physiologically acceptable buffer, such as saline or phosphate buffer or the like, from the PCV-2 antigen, preferably by filtration, even more preferably by dia- and/or ultra-filtration.

The concentrating step and the liquid addition step of the method as described herein can be performed substantially simultaneously or alternatively, the concentrating step and the liquid addition step are performed sequentially. Thus according to a further aspect, the present application provides a method of producing a PCV-2 antigenic composition comprising the steps of i) obtaining a first liquid containing a PCV-2 antigen, ii) removing at least a portion of the first liquid from the PCV-2 antigen by an exchange of a portion of the first liquid against a second liquid comprising the steps of a) adding the second liquid to the first liquid which contains the PCV-2 antigen and b) concentrating the PCV-2 antigen by removing a portion of the first and second liquids from the PCV-2 antigen, wherein the liquid addition step is performed simultaneously or sequentially. Preferably the portion of the first liquid and in the case of the addition of the second liquid, the mixture of the first and the second fluid is removed from the PCV-2 antigen by filtration, preferably by dia- and/or ultra-filtration.

When the concentrating step and liquid addition step are performed sequentially, the order of the steps does not matter. For example, in a further aspect, the liquid addition step occurs prior to the concentrating step and in an alternative aspect, the concentrating step occurs prior to the liquid addition step. The liquid addition step and the concentrating step, regardless of the order in which they are performed, can be performed multiple times. For example, each of these respective steps can be performed at least two, at least three, at least four, at least five, at least 10, up to as many times as desired. In one aspect, the concentrating step and the liquid addition step are each performed at least two times. In another aspect, the concentrating step and the liquid addition step are each performed at least three times. Thus, according to a further aspect of the present application, a method of producing a PCV-2 antigenic composition is provided wherein the method generally comprises the steps of i) obtaining a first liquid containing a PCV-2 antigen, ii) removing at least a portion of the first liquid from the PCV-2 antigen by an exchange of the portion of the first liquid against a second liquid, wherein the exchange is performed multiple times. Preferably the exchange of the portion of the first fluid against a portion of the second fluid comprises the steps of a) adding the second liquid to the first liquid which contains the PCV-2 antigen and b) concentrating the PCV-2 antigen by removing a portion of the first and second liquids from the PCV-2 antigen, wherein the liquid addition step and concentration step are performed multiple times, for instance, two times, three times, 5 times, 10 times, etc. Preferably, the liquid addition step and concentration step are performed two times, most preferably three times. As described above, filtration is the preferred method to remove a portion of the first liquid, or in case of multiple removing steps as described above, to remove a portion of the mixture of the first and the second fluid, from the PCV-2 antigen.

The filter can be any conventional filter in the art. Preferably, the filter includes a semi-permeable membrane. In a further preferred form, the semi-permeable membrane has an average pore size that is smaller than the PCV-2 antigen to thereby prevent passage of at least 90% of the PCV-2 antigen through the semi-permeable membrane pores and withhold the PCV-2 antigen by the filter. In a further aspect, the filter has an average pore size which prevents passage of at least 90% of proteins of 50 kDa to 500 kDa in size, more preferably, the filter has an average pore size which prevents passage of at least 90% of proteins of 75 kDa to 400 kDa in size, and most preferably, the filter has an average pore size which prevents passage of at least 90% of proteins of 100 kDa to 300 kDa in size. This pore size is preferred, when the PCV-2 antigen is produced as whole virus or as virus like particles. In a still further aspect, the semi-permeable membrane includes a material selected from the group consisting of polysulfone, polyethersulfone, and regenerated cellulose. However, any other material that allows removing of a portion of the first fluid, and in case of a multiple process step, removing of a mixture of the first and the second fluid from the PCV-2 antigen can be used. The filter can be selected from the group consisting of a hollow fiber membrane ultra filtration cartridge, flat sheets, or a cassette, with a hollow fiber membrane ultra filtration cartridge being particularly preferred. Thus, according to a further aspect of the present application, a method of producing a PCV-2 antigenic composition is provided as described above. The method generally comprises the steps of i) obtaining a first liquid containing a PCV-2 antigen, ii) removing at least a portion of the first liquid from the PCV-2 antigen by a filtration step, wherein the filter preferably is or comprises a semi-permeable membrane. Preferably, the semi-permeable membrane has an average pore size that is smaller than the PCV-2 antigen and prevent passage of at least 90% of the PCV-2 antigen through the semi-permeable membrane pores. Preferably the average pore size of the semi-permeable membrane prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. As described above, the removing step in general includes the exchange of the portion of the first fluid against a portion of the second fluid comprising the steps of a) adding the second liquid to the first liquid which contains the PCV-2 antigen and b) concentrating the PCV-2 antigen by removing a portion of the first and second liquids from the PCV-2 antigen, wherein the liquid addition step and concentration step are performed multiple times, for instance, two times, three times, 5 times, 10 times, etc. Preferably, the liquid addition step and the concentration step are performed two times, most preferably three times.

The concentration step of the method provided herein is performed such that the PCV-2 antigen is concentrated from 3× to 50× in comparison to the volume of the first liquid. More preferably, the concentrating step is done such that the PCV-2 antigen is concentrated 4× to 20× in comparison to the volume of the first liquid. Most preferably, concentration step is done such that the PCV-2 antigen is concentrated from 7× to 10× in comparison to the volume of the first liquid. Thus according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, wherein the portion of the first liquid is removed from the PCV-2 antigen, and wherein the PCV-2 antigen is concentrated from 3× to 50×, preferably from 4× to 20×, and even more preferably from 7× to 10× in comparison to the volume of the first liquid. Preferably, the portion of the first fluid is removed from the PCV-2 antigen by an exchange of the portion of the first liquid against a second liquid comprising the steps of a) adding the second liquid to the first liquid which contains the PCV-2 antigen and b) concentrating the PCV-2 antigen from 3× to 50×, preferably from 4× to 20×, and even more preferably from 7× to 10× in comparison to the volume of the first liquid by removing a portion of the first and second liquids from the PCV-2 antigen. Preferably, the liquid addition step and concentration step are performed multiple times, preferably two times, even more preferably three times. In such case, not only the first liquid is removed, but also a mixture of the first and second liquid. Preferably each liquid addition step is performed substantially simultaneously or sequentially. When the concentrating step and liquid addition step are performed sequentially, the order of the steps does not matter. Moreover, the concentration step is preferably done by filtration—preferably dia- and/or ultra-filtration, utilizing a filter, which preferably contains a semi-permeable membrane. The semi-permeable membrane preferably has an average pore size that is smaller than the PCV-2 antigen and prevent passage of at least 90% of the PCV-2 antigen through the semi-permeable membrane pores. Preferably the average pore size of the semi-permeable membrane is prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

In a further aspect, the virucidal activity of the PCV-2 antigenic composition produced by the methods herein is reduced by at least 10% as compared to the liquid that has not undergone the method. More preferably, the virucidal activity of the PCV-2 antigenic composition is reduced by at least 50% as compared to the first liquid that has not undergone the method. Still more preferably, the virucidal activity of the PCV-2 antigenic composition is reduced by at least 70% as compared to the first liquid that has not undergone the method.

For the purpose of the current invention the term "virucidal activity" means, that a fluid, solution or composition inactivates or kills a live virus or live bacteria to a certain extent, when the fluid, solution or composition is mixed with such live virus or live bacteria. Thus, a reduction of the virucidal activity of a fluid, solution or composition by at least 10% means, that the survival rate of a live virus or live bacteria is 90% higher in a fluid, solution or composition that has undergone any of the methods described herein, as compared to a fluid, solution or composition, that has not undergone any of the method described herein. According to the present invention, the PRRS virus, preferably PRRS virus having the ATCC accession number VR 2332, is the reference virus for the determination of virucidal activity. To determine the virucidal activity with regard to a bacterium, it is proposed to use the *Mycoplasma hyopneumonia* bacterium, preferably the J-strain of *Mycoplasma hyopneumonia*.

Thus according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, wherein the virucidal activity—preferably in respect to PRRS virus—of the PCV-2 antigenic composition obtained after step ii) is reduced by at least 10%, preferably at least 50%, more preferably at least 70%, even more preferably at least 90% as compared to that of the first liquid. Preferably, the portion of the first liquid having virucidal activity is removed from the PCV-2 antigen by an exchange of a portion of the first liquid against a second liquid. The exchange is preferably done in such a manner that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably, the liquid addition step and concentration step are performed multiple times, preferably two times, and even more preferably three times. In such case, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- and/or ultra-filtration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

In a further aspect, the method further comprises the step of harvesting the PCV-2 antigen obtained after at least a portion of the first liquid is removed from the PCV-2 antigen.

As used herein, "harvesting" or "harvest" refers to the collecting or recovering of the PCV-2 antigen. Any conventional method known in the art can be used to recover the PCV-2 antigen either when an antigen is being produced for use with the methods and compositions of the present application, or when the PCV-2 antigen is undergoing the methods described herein. In a particularly preferred manner of harvesting, the portion of the first liquid is removed from the PCV-2 antigen via a filtration step and the PCV-2 antigen is recovered or harvested from the filter retard. In a more preferred form, the PCV-2 antigen is harvested or collected, or recovered from the retard of a semi-permeable membrane having the pore size described herein. Thus, according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, wherein the PCV-2 antigen obtained after the step ii) is harvested. Preferably, the portion of the first liquid is removed from the PCV-2 antigen by an exchange of a portion of the first liquid against a second liquid. The exchange is preferably done such that it comprises the steps of a) adding a second liquid to the first liquid which contains the PCV-2 antigen and b) concentrating the PCV-2 antigen, preferably from 3x to 50x, even more preferably from 4x to 20x, and even more preferably from 7x to 10x in comparison to the volume of the first liquid by removing a portion of the first and second liquids from the PCV-2 antigen. Preferably, the liquid addition step and concentration step are performed multiple times, preferably two times, even more preferably three times. In such cases, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- and/or ultra-filtration, utilizing a filter, which preferably contains a semi-permeable membrane. The semi-permeable membrane preferably has an average pore size that is smaller than the PCV-2 antigen and prevent passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

The PCV-2 antigen remaining after undergoing the methods provided herein, preferably after being harvested from the filter retard, is admixed with a further component selected from the group consisting of pharmaceutically acceptable carriers, adjuvants, diluents, excipients, and combinations thereof. Preferably, the further component is an adjuvant, even more preferably wherein the adjuvant is a polymer of acrylic or methacrylic acid, and still more preferably wherein the adjuvant is Carbomer (the generic name for synthetic high molecular weight polymers of acrylic acid).

As used herein, "a pharmaceutical-acceptable carrier" and a "veterinary acceptable carrier" includes any and all solvents, dispersion media, coatings, stabilizing agents, diluents, preservatives, antibacterial and antifungal agents, isotonic agents, adsorption delaying agents, and the like.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book. Further suitable adjuvants include, but are not limited to, the RIBI adjuvant system (Ribi Inc.), Block copolymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others. Among the copolymers of maleic anhydride and alkenyl derivative, the copolymers EMA (Monsanto), which are copolymers of maleic anhydride and ethylene, are included. The dissolution of these polymers in water leads to an acid solution that will be neutralized, preferably to physiological pH, in order to give the adjuvant solution into which the immunogenic, immunological or vaccine composition itself will be incorporated.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are polymers of acrylic acid cross-linked with polyalkenyl ethers or divinyl glycol or cross-linked with an allyl sucrose or with allyl pentaerythritol. Among them, there may be mentioned CARBOPOL® 974P, 934P and 971P. Most preferred is the use of CARBOPOL® 971P.

Preferably, the adjuvant is added in an amount of about 100 µg to about 10 mg per dose. Even more preferably the adjuvant is added in an amount of about 100 µg to about 10 mg per dose. Still more preferably the adjuvant is added in an amount of about 500 µg to about 5 mg per dose. Still more preferably the adjuvant is added in an amount of about 750 µg to about 2.5 mg per dose. Most preferably the adjuvant is added in an amount of about 1 mg per dose.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

A "preservative" as used herein refers to an anti-microbiological active agent, such as for example Gentamycin, Merthiolate, and the like. In particular adding of a preservative is most preferred for the preparation of a multi-dose composition. Those anti-microbiological active agents are added in concentrations effective to prevent the composition of interest for any microbiological contamination or for inhibition of any microbiological growth within the composition of interest.

Thus, according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, further comprising the step of admixing the PCV-2 antigen remaining after step ii) with a further component selected from the group consisting of pharmaceutically acceptable carriers, adjuvants, diluents, excipients, and combinations thereof. Preferably wherein the further component is an adjuvant, even more preferably wherein the adjuvant is a polymer of acrylic or methacrylic acid, and still more preferably wherein the adjuvant is Carbomer. Preferably, the portion of the first liquid is removed from the PCV-2 antigen by an exchange of a portion of the first liquid against a second liquid. The exchange is preferably done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably, the liquid addition step and the concentration step are performed multiple times, preferably two times, and even more preferably three times. In such cases, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- and/or ultrafiltration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

The PCV-2 antigen used in the methods described above can be any PCV-2 antigen as defined herein. Preferably the PCV-2 antigen comprises the ORF-2 protein of PCV-2, more preferably recombinant ORF-2 protein of PCV-2, and still more preferably virus like particles of ORF-2 protein, and even more preferably the antigen included in INGELVAC CIRCOFLEX®. Thus, according to a further aspect of the present application, the present application provides a method of producing a PCV-2 antigenic composition comprising the steps of i) obtaining a first liquid containing a PCV-2 antigen, ii) removing at least a portion of the first liquid from the PCV-2 antigen, wherein the PCV-2 antigen comprises the ORF-2 protein of PCV-2, more preferably recombinant ORF-2 protein of PCV-2, and still more preferably virus like particles of ORF-2 protein. Preferably, the portion of the first liquid is removed from the PCV-2 antigen by an exchange of a portion of the first liquid against a second liquid. The exchange is preferably done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen.

Preferably, the liquid addition step and concentration step are performed multiple times, preferably two times, and even more preferably three times. In such cases, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- and/or ultrafiltration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

The first liquid containing the PCV-2 antigen used can be obtained by any method known in the art. Preferably, the first liquid containing the PCV-2 antigen as well as PCV-2 antigen can be obtained by any of the methods described in the international patent application WO2006/072065 (the contents and teachings of which are hereby incorporated by reference). In particular, the PCV-2 antigen, when expressed recombinantly in vitro in host cells, can be obtained via a viral vector, preferably a recombinant baculovirus viral vector, containing and expressing the PCV-2 antigen, preferably, PCV-2 ORF-2.

Vectors and methods for making and/or using vectors (or recombinants) for expression of the PCV-2 antigen, preferably the PCV-2 ORF2 antigen can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018, Paoletti, "Applications of pox virus vectors to vaccination: An update," PNAS USA 93: 11349-11353, October 1996, Moss, "Genetically engineered poxviruses for recombinant gene expression, vaccination, and safety,"

PNAS USA 93: 11341-11348, October 1996, Smith et al., U.S. Pat. No. 4,745,051, (recombinant baculovirus), Richardson, C. D. (Editor), Methods in Molecular Biology 39, "Baculovirus Expression Protocols" (1995 Humana Press Inc.), Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 399-406; EPA0 370 573, U.S. application No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307-11312, October 1996, Andreansky et al., "The application of genetically engineered herpes simplex viruses to the treatment of experimental brain tumors," PNAS USA 93: 11313-11318, October 1996, Robertson et al. "Epstein-Barr virus vectors for gene delivery to B lymphocytes", PNAS USA 93: 11334-11340, October 1996, Frolov et al., "Alphavirus-based expression vectors: Strategies and applications," PNAS USA 93: 11371-11377, October 1996, Kitson et al., J. Virol. 65, 3068-3075, 1991; U.S. Pat. Nos. 5,591,439, 5,552,143, WO 98/00166, allowed U.S. application Ser. Nos. 08/675, 556, and 08/675,566 both filed Jul. 3, 1996 (recombinant adenovirus), Grunhaus et al., 1992, "Adenovirus as cloning vectors," Seminars in Virology (Vol. 3) p. 237-52, 1993, B allay et al. EMBO Journal, vol. 4, p. 3861-65, Graham, Tibtech 8, 85-87, April, 1990, Prevec et al., J. Gen Virol. 70, 42434, PCT WO 91/11525, Felgner et al. (1994), J. Biol. Chem. 269, 2550-2561, Science, 259: 1745-49, 1993 and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996, and U.S. Pat. Nos. 5,591,639, 5,589, 466, and 5,580,859, as well as WO 90/11092, WO93/19183, WO94/21797, WO95/11307, WO95/20660, Tang et al., Nature and Furth et al. Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel), WO 90/01543; Robinson et al., seminars in Immunology vol. 9, pp. 271-283 (1997), (DNA vector systems); Szoka et al., U.S. Pat. No. (method of inserting DNA into living cells); McCormick et al., U.S. Pat. No. 5,677,178 (use of cytopathic viruses); and U.S. Pat. No. 5,928,913 (vectors for gene delivery), as well as other documents cited herein. The expression of PCV-2 ORF2 antigen in insect cells is described, for instance, in WO 06/072065. The purified PCV-2 ORF2 antigen according to the invention can be obtained by several methods known in the art. Preferred methods are those described herein. The PCV-2 ORF2 antigen can be produced recombinantly in vitro by the method comprising the steps i) permitting infection of susceptible cells in culture with a recombinant viral vector containing PCV-2 ORF2 coding sequence, wherein the PCV-2 ORF2 protein is expressed by the recombinant viral vector, and ii) thereafter recovering the PCV-2 ORF2 antigen from cell culture. The PCV-2 ORF2 antigen is recovered by harvesting the whole (i.e. intact) SF+ cells expressing the PCV-2 ORF2 antigen.

Thus, according to a further aspect of the present application, the present application provides a method of producing a PCV-2 antigenic composition comprising the steps of i) obtaining a first liquid containing a PCV-2 antigen, ii) removing at least a portion of the first liquid from the PCV-2 antigen, wherein the PCV-2 antigen is obtained via a viral vector, preferably a recombinant baculovirus viral vector, containing and expressing the PCV-2 antigen, preferably, PCV-2 ORF-2, and wherein the PCV-2 antigen comprises the ORF-2 protein of PCV-2, more preferably recombinant ORF-2 protein of PCV-2, and still more preferably virus like particles of ORF-2 protein. When a viral vector, in particular a recombinant baculovirus containing and expressing the PCV-2 antigen is used to produce/obtain the PCV-2 antigen, the method described above further comprises the step of inactivating the viral vector, preferably the recombinant baculovirus viral vector with a DNA inactivating agent, preferably in the presence of about 1 to about 20 mM of binary ethylenimine. Preferably, the inactivating step is performed after at least a portion of the first liquid is removed from the PCV-2 antigen, more preferably after the PCV-2 antigen is harvested. Even more preferably, the inactivating step is performed after the portion of the first liquid is removed from the PCV-2 antigen by an exchange of a portion of the first liquid against a second liquid. When the exchange of a portion of the first liquid against a second liquid is done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen, the inactivating step is done after the concentration step. When the liquid addition step and concentration step are performed multiple times, preferably two times, even more preferably three times, the inactivation step is performed after the last liquid addition step and concentration step. When the concentration step is done by filtration—preferably by dia- and/or ultra-filtration, utilizing a filter, preferably containing a semi-permeable membrane, the inactivation step is performed after the filtration step described above, preferably utilizing a semi-permeable membrane. The semi-permeable membrane preferably has an average pore size that is smaller than the PCV-2 antigen and prevent passage of at least 90% of the PCV-2 antigen through the semi-permeable membrane pores and withhold the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

"DNA inactivating agent", for purposes of the present invention, refers to any chemical agent which deactivates the DNA, preferably, DNA of a pathogen, such that the pathogen cannot cause active infection or be infective or replicate, but is still capable of inducing an immune response in a subject. Preferably, the DNA inactivating agent is formalin.

Thus, according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, wherein the PCV-2 antigen is obtained via a viral vector, preferably a recombinant baculovirus viral vector, containing and expressing the PCV-2 antigen, preferably, PCV-2 ORF-2, wherein the method further comprises the step of inactivating the viral vector, preferably the recombinant baculovirus viral vector with a DNA inactivating agent, preferably in the presence of about 1 to about 20 mM of binary ethylenimine, and wherein the PCV-2 antigen comprises the ORF-2 protein of PCV-2, more preferably recombinant ORF-2 protein of PCV-2, and still more preferably virus like particles of ORF-2 protein. Preferably, the inactivating step is performed after at least a portion of the first liquid is removed from the PCV-2 antigen, more preferably after the PCV-2 antigen is harvested. Even more preferably, the inactivating step is performed after the portion of the first liquid is removed from the PCV-2 antigen by an exchange of a portion of the first liquid against a second liquid. When the exchange of a portion of the first liquid against a second liquid is done such that it comprises the steps of a) adding the second liquid to the first liquid which contains the PCV-2 antigen and b) concentrating the PCV-2 antigen, preferably from 3× to 50×, even more preferably from 4× to 20×, even more preferably from 7× to 10× in comparison to the volume of the first liquid by removing a portion of the first and second liquids from the PCV-2 antigen, the inactivating step is done after the concentration step. When the liquid addition step and concentration step are performed multiple times, preferably two times, even more preferably three times, such inactivation step is performed after the last liquid addition step and concentration step. When the concentration step is done by filtration—preferably by dia- and/or ultra-filtration, utilizing a filter, preferably containing a semi-permeable membrane, the inactivation step is performed after the filtration step described above, preferably utilizing a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

In the case that a DNA inactivating agent is used in the method according to the invention the method further comprises the step of adding an amount of an agent that neutralizes the DNA inactivating agent, the amount being equivalent to the amount of the DNA inactivating agent wherein the agent that neutralizes the DNA inactivating agent comprises a sodium thiosulfate solution concentrated to a final concentration of about 1 to about 20 mM and wherein the DNA inactivating agent is BEI. Preferably, the inactivating step is performed after at least a portion of the first liquid is removed from the PCV-2 antigen.

"Agent that neutralizes the inactivating agent" or "neutralizing agent", as used herein, refers to any agent capable of neutralizing the inactivating agents listed above such that the inactivating agent is no longer capable of inactivating DNA. The agent that neutralizes the inactivating agent is preferably sodium thiosulfate.

Thus, according to a further aspect, the present application provides a method of producing a PCV-2 antigenic composition comprising the steps of i) obtaining a PCV-2 antigen in a first liquid wherein the PCV-2 antigen is obtained via a viral vector, preferably a recombinant baculovirus viral vector, containing and expressing the PCV-2 antigen, preferably, PCV-2 ORF-2, and wherein the PCV-2 antigen comprises the ORF-2 protein of PCV-2, more preferably recombinant ORF-2 protein of PCV-2, and still more preferably virus like particles of ORF-2 protein; ii) removing at least a portion of the first liquid from the PCV-2 antigen; iii) inactivating the recombinant baculovirus viral vector with a DNA inactivating agent, preferably in the presence of about 1 to about 20 mM of binary ethylenimine; iv) adding an amount of a neutralizing agent that neutralizes the inactivating agent, the amount of neutralizing agent being equivalent to the amount of the inactivating agent, wherein the neutralizing agent preferably comprises a sodium thiosulfate solution preferably concentrated to a final concentration of about 1 to about 20 mM and wherein the inactivating agent preferably comprises BEI. Preferably, the inactivating and neutralization step is performed after at least a portion of the first liquid is removed from the PCV-2 antigen, more preferably after the PCV-2 antigen is harvested. Even more preferably, the inactivating and neutralization step is performed after the portion of the first liquid is removed from the PCV-2 antigen by an exchange of a portion of the first liquid against a second liquid. When the exchange of a portion of the first liquid against a second liquid is done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen, the inactivating and neutralization step is done after the concentration step. When the liquid addition step and concentration step are performed multiple times, preferably two times, even more preferably three times, the inactivation and neutralization step is performed after the last liquid addition step and concentration step. When the concentration step is done by filtration—preferably by dia- and/or ultrafiltration, utilizing a filter, preferably containing a semi-permeable membrane, the inactivation and neutralization step is performed after the filtration step described above, preferably utilizing a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

In a further aspect of the present application, the method described above further comprises the steps admixing the PCV-2 antigen obtained after the inactivating and neutralizing steps with a further component selected from the group consisting of pharmaceutically acceptable carriers, adjuvants, diluents, excipients, and combinations thereof. Thus, according to a further aspect, the present application provides a method of producing a PCV-2 antigenic composition comprising the steps of i) obtaining a PCV-2 antigen in a first liquid, wherein the PCV-2 antigen is obtained via a viral vector, preferably a recombinant baculovirus viral vector, containing and expressing the PCV-2 antigen, preferably, PCV-2 ORF-2, and wherein the PCV-2 antigen comprises the ORF-2 protein of PCV-2, more preferably recombinant ORF-2 protein of PCV-2, and still more preferably virus like particles of ORF-2 protein; ii) removing at least a portion of the first liquid from the PCV-2 antigen; iii) inactivating the recombinant baculovirus viral vector with a DNA inactivating agent, preferably in the presence of about 1 to about 20 mM of binary ethylenimine; iv) adding an amount of a neutralizing agent that neutralizes the inactivating agent, the amount of neutralizing agent preferably being equivalent to the amount of the inactivating agent, wherein the neutralizing agent preferably comprises a sodium thiosulfate solution preferably concentrated to a final concentration of about 1 to about 20 mM and wherein the inactivating agent preferably comprises BEI; and v) admixing the PCV-2 antigen obtained in step iv) with a further component selected from the group consisting of pharmaceutically acceptable carriers, adjuvants, diluents, excipients, and combinations thereof. Preferably, the PCV-2 antigen comprises the ORF-2 protein of PCV-2, more preferably recombinant ORF-2 protein of PCV-2, and still more preferably virus like particles of ORF-2 protein. Preferably, in step ii), the portion of the first liquid is removed from the PCV-2 antigen by an exchange of a portion of the first liquid against a second liquid. The exchange is preferably done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably, the liquid addition step and concentration step are performed multiple times, preferably two times, even more preferably three times. In such case, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- and/or ultrafiltration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

According to a further aspect, any of the method described above to obtain a PCV-2 antigen with reduced virucidal activity can include further purification steps to obtain a purified PCV-2 antigen. It was surprisingly found that an antigenic or immunogenic composition comprising a purified PCV-2 antigen, preferably in combination with an adjuvant, not only shows a reduced virucidal activity as described herein, but also shows an increased immunogenicity as compared to an immunogenic composition, which does not comprise a purified PCV-2 antigen, means which comprises a non-purified or crude PCV-2 antigen.

The term "purified PCV-2 antigen" means, that the PCV-2 antigen is purified in a preparation to an extent of more than 50% (w/w), preferably of more than 60% (w/w), preferably of more than 70% (w/w), preferably of more than 80% (w/w), preferably of more than 85% (w/w), more preferably of more than 90% (w/w), even more preferable of more than 95% (w/w) with reference to the total amount of protein included in the immunogenic composition. In other words, if a preparation comprises a PCV-2 antigen with purity grade of 80% (w/w), such preparation comprise not more than 20% (w/w) of non PCV-2 proteins with reference to the total amount of protein included in the immunogenic composition. Preferably, the grade of purity is measured in the preparation, i.e. in the immunogenic composition before admixing with adjuvant or any other excipients or inactivating agent. However, if the adjuvant used in the final immunogenic composition is a non-protein based adjuvant, the addition of the adjuvant does not have any effect of the purity value. The purity grade of the PCV-2 antigen can be estimated by standard methods known to a person skilled in the art, for instance by Imperial Protein Stain (Pierce) after SDS-PAGE separation, gas chromatography, HPLC analyses, etc. The preferred method according to this invention to estimate the purity or purity grade of a PCV-2 antigen in a preparation i.e. an immunogenic composition is the Imperial Protein Stain (Pierce) staining, which is done as follows: The preparation comprising the PCV-2 antigen are separated via NuPAGE 10% Bis-Tris gels (Invitrogen) using the NuPAGE MOPS buffer system (Invitrogen). Gels were run under denaturing (all buffers have SDS in them) and reducing conditions (the loading buffer has 2-mercaptoethanol). After loading the gels with samples, the gels were run for 55 min at 200 Volts constant. Once the run was completed, the gels were stained using Imperial Protein Stain (Pierce) and destained according the manufacturer's instructions.

In contrast, the term "non-purified" or "crude" PCV-2 antigen refers to a crude preparation comprising PCV-2 antigen. PCV-2 antigen is normally produced in vitro in cell culture. Thus, a crude PCV-2 antigen refers to a mixture of PCV-2 antigen and the cell culture or cell culture material used for the production of the PCV-2 antigen. Moreover, a non-purified PCV-2 antigen also means a partial purified PCV-2 antigen, preferably having a purity grade of less than 50% (w/w), more preferred of less than 40% (w/w), even more preferred of less than 30% (w/w), even more preferred of less than 20% (w/w) with reference to the total amount of protein included in the immunogenic composition.

In addition, the terms "increased immunogenicity or improved immunogenicity" as used herein, mean that the immune response caused by an immunogenic composition comprising an antigen of interest is increased as compared to a reference immunogenic composition comprising a different antigen or different purity grade of the antigen, whether this immune response is a cellular mediated and/or antibody mediated immune response. According to a preferred embodiment, the term increased immunogenicity or improved immunogenicity means, that the antibody mediated immune response elicited by an immunogenic composition comprising the antigen of interest is increased as compared to a reference immunogenic composition comprising a different antigen or a different purity grade of the antigen. In this regard antibody mediated immune response means, that the production of antibodies, which are specific to the antigen of interest is increased as compared to the antibody production elicited by a reference immunogenic composition comprising a different antigen or a different purity grade of the antigen.

The term "increased" means, that the cellular and/or antibody mediated immune response is increased by at least 10%, preferably by at least 20%, more preferably by at least 30%, even more preferably by at least 40%, even more preferably by at least 50%, even more preferably by at least 75%, most preferably by at least 100% as compared to the cellular and/or antibody mediated immune response elicited by a reference immunogenic composition comprising a different antigen or a different purity grade of the antigen.

It is in the general knowledge of a person skilled in the art how to measure the cellular and/or antibody mediated immune response. In particular, it is clear to such person skilled in the art either to compare the cellular mediated immune response of the immunogenic composition of interest with cellular mediated immune response of the reference, or the antibody mediated immune response of the immunogenic composition of interest with that of the reference composition, but neither the cellular mediated immune response of a immunogenic composition of interest with the antibody mediated immune response of the reference or vice versa. Moreover, the cellular mediated immune response can be measured, for instance, by measuring the activation of cytotoxic T-cells by an immunogenic composition/antigen of interest. The antibody mediated immune response can be measured, for instance, by measuring the amount of antigen specific antibodies, generated in cause of the administration of the immunogenic composition comprising such antigen to an animal. The cellular and/or antibody mediated immune response can be measured, for instance, by using a mouse model. According to the current invention, the mouse model is used as the reference method.

The term "immunogenic composition" means, but is not limited to, a composition of matter that comprises at least one antigen which elicits a cellular and/or antibody-mediated immune response in a host against the antigen of interest. Usually, an "immune response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immune response such that resistance to new infection will be enhanced and/or the clinical severity of the disease reduced. In such a case the immunogenic composition is a "vaccine". Such protection will be demonstrated by either a reduction or lack of symptoms normally displayed by an infected host, a quicker recovery time and/or a lowered viral titer in the infected host.

Further purification of the PCV-2 antigen can be achieved with chromatography procedures, preferably a two-step chromatography procedure. If the PCV-2 antigen is assembled to virus like particles (VLP), one step, preferably the first step, is preferably a size exclusion (gel filtration) chromatography, which can be done, for instance, by using a Sephacryl S300 matrix. In lab scale use of HiPrep 26/60 Sephacryl S300HR columns are most preferred. However, any other size exclusion chromatography matrices known to a person skilled in the art can be used, which allow the separation of the PCV-2 ORF2 VLPs from the culture filtrate or supernatant. Suitable matrices are described, for instance, in E. L. V. Harris and S. Angel (eds.), Protein purification methods—a practical approach, IRL Press Oxford 1995). The gel filtration chromatography can be conducted, for instance, by loading the column with the crude preparation comprising the PCV-2 antigen with a flow-rate of 1.0 ml/min and eluting the column with 1.5 column volume of a buffer comprising 20 mM Tris, pH 6.5, 5 mM DTT. However, the PCV-2 ORF2 antigen can also be purified by using affinity chromatography, for instance, via selective binding to an immobilized PCV-2 ORF2 specific antibody, or any other method known to a person skilled in the art.

Thus according to a preferred embodiment the present invention provides a method of producing a PCV-2 antigenic composition comprising the steps of i) obtaining a first liquid containing a PCV-2 antigen, ii) removing at least a portion of the first liquid from the PCV-2 antigen and iii) purifying the harvest of step ii) comprising the PCV-2 antigen, preferably the PCV-2 ORF2 antigen by chromatographic procedure. Preferably size exclusion chromatography is performed as described herein, preferably as described in Example 3. Preferably, the size exclusion results in an immunogenic composition having purity grade of more than 80% (w/w), preferably more than 90% (w/w) with reference to the total amount of protein included in the immunogenic composition prior to the mixture with the adjuvant. The purity grade can be estimated by Imperial Protein Stain (Pierce) staining after SDS PAGE via NuPAGE 10% Bis-Tris gels (Invitrogen) using the NuPAGE MOPS buffer system (Invitrogen).

Thus according to a preferred embodiment the present invention provides a method of producing a PCV-2 antigenic composition comprising the steps of i) obtaining a first liquid containing a PCV-2 antigen, ii) removing at least a portion of the first liquid from the PCV-2 antigen and iii) purifying the harvest of step ii) comprising the PCV-2 antigen by size exclusion chromatography (gel filtration).

In order to obtain a higher purity grade a second chromatography step can be done, which however is different from the first one. For instance if the first purification step/chromatography step is size exclusion (gel filtration) the second should different from that e.g. an affinity chromatography, ion exchange chromatography, etc. Preferably, if the first step to purify PCV-2 antigen, preferably to purify PCV-2 ORF2 antigen is a size exclusion (gel filtration) chromatography, the second step can be ion-exchange chromatography, preferably anion-exchange chromatography (AIEX) A preferred anion-exchange chromatography matrix for the purification of PCV-2 antigen, preferably the PCV-2 ORF2 antigen is Q Sepharose. In a small scale of about 50 ml, use of 5 ml HiTrap Q Sepharose HP columns are most preferred. The anion exchange chromatography can be conducted, for instance, as described in Example 3. Briefly, about 50 ml of the void volume fraction pool from the size exclusion chromatography step can be loaded onto the AIEX column at a flow rate of 3.0 ml/min. Following a washing step using, for instance, 20 mM Tris, pH 6.5, 5 mM DTT to remove unbound material, protein can be eluted with a single step of 8 column volumes of the following buffer (20 mM Tris, pH 6.5, 5 mM DTT, 1.0 M NaCl) The flow-through from the AIEX run can be loaded back onto the Q Sepharose column and eluted as described above to increase the yield. This two step technique (size exclusion followed by anion-exchange chromatography) effectively separates PCV-2 ORF2 antigen from most of the other protein components of the culture harvest.

Thus according to a preferred embodiment the present invention provides a method of producing a PCV-2 antigenic composition comprising the steps of i) obtaining a first liquid containing a PCV-2 antigen, ii) removing at least a portion of the first liquid from the PCV-2 antigen and iii) purifying the harvest of step ii) comprising the PCV-2 antigen, by a two-step chromatography. Preferably the first chromatography step is different from the second step. If the first step is a size exclusion (gel filtration) chromatography, the second step can be ion-exchange chromatography, preferably anion-exchange chromatography (AIEX). Preferably, in any of the methods described above, which include one or more further purification steps to obtain a purified PCV-2 antigen, preferably a PCV-2 ORF-2 protein, the portion of the first liquid is removed from the PCV-2 antigen by an exchange of a portion of the first liquid against a second liquid. The exchange is preferably done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably, the liquid addition step and concentration step are performed multiple times, preferably two times, and even more preferably three times. In such cases, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- or ultra-filtration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. In preferred forms, the method of producing a PCV-2 antigenic composition described above further comprises the steps of i) obtaining a PCV-2 antigen in a first liquid wherein the PCV-2 antigen is obtained via a viral vector, preferably a recombinant baculovirus viral vector, containing and expressing the PCV-2 antigen, preferably, PCV-2 ORF-2, and wherein the PCV-2 antigen comprises the ORF-2 protein of PCV-2, more preferably recombinant ORF-2 protein of PCV-2, and still more preferably virus like particles of ORF-2 protein; ii) removing at least a portion of the first liquid from the PCV-2 antigen; iii) inactivating the recombinant baculovirus viral vector with a DNA inactivating agent, preferably in the presence of about 1 to about 20 mM of binary ethylenimine; iv) adding an amount of a neutralizing agent that neutralizes the inactivating agent, the amount of neutralizing agent being equivalent to the amount of the inactivating agent, wherein the neutralizing agent preferably comprises a sodium thiosulfate solution preferably concentrated to a final concentration of about 1 to about 20 mM and wherein the inactivating agent preferably comprises BEI; and v) admixing the PCV-2 antigen obtained in step iv) with a further component selected from the group consisting of pharmaceutically acceptable carriers, adjuvants, diluents, excipients, and combinations thereof. The further purification, preferably, the two step purification strategy including the pre-filtration step results in an immunogenic composition having purity grade of more than 80% (w/w), preferably of more than 85% (w/w), even more preferred of more than 90% (w/w), most preferred of more than 95% (w/w) with reference to the total amount of protein included in the immunogenic composition prior to the mixture with any adjuvant.

The PCV-2 antigenic composition produced by the method described herein causes a loss of less than 1 log $TCID_{50}$ of a live virus or less than 1 log CFU per ml of a live bacterium, when the live virus or live bacterium is mixed with the PCV-2 antigenic composition and incubated for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. More preferably, the PCV-2 antigenic composition produced by the method described herein causes a loss of less than 0.9 log $TCID_{50}$ per ml of a live virus or less than 0.9 log CFU per ml of a live bacterium, when the live virus or live bacterium is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. Even more preferably, the PCV-2 antigenic composition produced by the method described herein causes a loss of less than 0.7 log $TCID_{50}$ per ml of a live virus or less than 0.7 log CFU per ml of a live bacterium, when the live virus or live bacterium is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. Still more preferably, the PCV-2 antigenic composition produced by steps by the method described herein causes a loss of less than 0.5 log $TCID_{50}$ per ml of a live virus or less than 0.5 log CFU per ml of a live bacterium, when the live virus or live bacterium is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. Even more preferably, the PCV-2 antigenic composition produced by the method described herein causes a loss of less than 0.3 log $TCID_{50}$ per ml of a live virus or less than 0.3 log CFU per ml of a live bacterium, when the live virus or live bacterium is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. The live virus can be any live virus, but preferably the live virus is the PRRS virus, preferably the PRRS virus having the ATCC accession number VR 2332. The live bacterium can be any bacterium, but is preferably the *Mycoplasma hyopneumonia* bacterium, preferably the J-strain of *Mycoplasma hyopneumonia*. The $TCID_{50}$ per ml can be estimated by a standard in vitro titration assay which allow the estimation of the amount of a live virus. The CFU per ml can be determined also by a standard in vitro titration assay which allows the estimation of the amount of a live bacterium. The term "per ml" preferably refers to 1 ml of a fluid. Such purified PCV-2 antigen, does not only show reduced virucidal activity, as defined herein, it also shows an increased immunogenicity as compared to a non-purified PCV-2 antigen as defined herein, preferably such purified PCV-2 antigen increases the cellular and/or antibody mediated immune response by at least 10%, preferably by at least 20%, more preferably by at least 30%, even more preferably by at least 40%, even more preferably by at least 50%, even more preferably by at least 75%, most preferably by at least 100% as compared to the cellular and/or antibody mediated immune response elicited by a reference immunogenic composition comprising a non-purified PCV-2 antigen.

Thus according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, wherein the PCV-2 antigenic composition obtained after step ii) causes a loss of less than 1 log $TCID_{50}$—preferably per ml—, preferably less than 0.9 log $TCID_{50}$,—preferably per ml—, even more preferably less than 0.7 log $TCID_{50}$—preferably per ml—, even more preferably less than 0.5 log $TCID_{50}$—preferably per ml—, most preferably less than 0.3 log $TCID_{50}$—preferably per ml—of a live virus, preferably of a live PRRSV or less than 1 log CFU—preferably per ml—, preferably less than 0.9 log CFU—preferably per ml—, even more preferably less than 0.7 log CFU—preferably per ml—, even more preferably less than 0.5 log CFU—preferably per ml—, most preferably less than 0.3 log CFU—preferably per ml—of a live bacterium, preferably of *Mycoplasma hyopneumoniae*, when the live virus, preferably PRRSV or live bacterium, preferably *Mycoplasma hyopneumoniae* is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. Preferably, the portion of the first liquid is removed from the PCV-2 antigen by an exchange of a portion of the first liquid against a second liquid. The exchange is preferably done in such that it comprises the steps of a) adding the second liquid to the first liquid which contains the PCV-2 antigen and b) concentrating the PCV-2 antigen, preferably from 3× to 50×, even more preferably from 4× to 20×, even more preferably from 7× to 10× in comparison to the volume of the first liquid by removing a portion of the first and second liquids from the PCV-2 antigen. Preferably, the liquid addition step and concentration step are performed multiple times, preferably two times, even more preferably three times. In such case, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- and/or ultra-filtration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. When the PCV-2 antigen is obtained via a viral vector, preferably a recombinant baculovirus viral vector, containing and expressing the PCV-2 antigen, preferably, PCV-2 ORF-2, the process further comprises iii) inactivating the recombinant baculovirus viral vector with a DNA inactivating agent, preferably in the presence of about 1 to about 20 mM of binary ethylenimine; iv) adding an amount of a neutralizing agent that neutralizes the inactivating agent, the amount of neutralizing agent being equivalent to the amount of the inactivating agent, wherein the neutralizing agent preferably comprises a sodium thiosulfate solution preferably concentrated to a final concentration of about 1 to about 20 mM and wherein the inactivating agent preferably comprises BEI. Preferably, the inactivating and neutralization steps are performed after at least a portion of the first liquid is removed from the PCV-2 antigen, more preferably after the PCV-2 antigen is harvested. Even more preferably, the inactivating and neutralization steps are performed after the portion of the first liquid is removed from the PCV-2 antigen by an exchange of a portion of the first liquid against a second liquid. When the exchange of a portion of the first liquid against a second liquid is done such that it comprises the steps of a) adding the second liquid to the first liquid which contains the PCV-2 antigen and b) concentrating the PCV-2 antigen, preferably from 3× to 50×, even more preferably from 4× to 20×, even more preferably from 7× to 10× in comparison to the volume of the first liquid by removing a portion of the first and second liquids from the PCV-2 antigen, the inactivating and neutralization steps are done after the concentration step. When the liquid addition step and concentration step are performed multiple times, preferably two times, and even more preferably three times, such inactivation and neutralization steps are performed after the last liquid addition step and concentration step. When the concentration step is done by filtration—preferably by dia- and/or ultrafiltration, utilizing a filter, preferably containing a semi-permeable membrane, the inactivation and neutralization steps are performed after the filtration step described above, preferably utilizing a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. Preferably, further purification to obtain a purified PCV-2 antigen as defined herein, can be achieved by performing further purification step comprising iii) purifying the harvest of step ii) comprising the PCV-2 antigen, which is obtained after the removal of a portion of the first liquid, by a chromatography a step. In order to obtain a higher purity grade a second chromatography step can be done, which however is different from the first one. For instance if the first purification step/chromatography step is size exclusion (gel filtration) the second should different from that e.g. an affinity chromatography, ion exchange chromatography, etc. Preferably, if the first step to purify PCV-2 antigen, preferably to purify PCV-2 ORF2 antigen is a size exclusion (gel filtration) chromatography, the second step can be ion-exchange chromatography, preferably anion-exchange chromatography (AIEX). A preferred anion-exchange chromatography matrix for the purification of PCV-2 antigen, preferably the PCV-2 ORF2 antigen is Q Sepharose. In a small scale of about 50 ml, use of 5 ml HiTrap Q Sepharose HP columns are most preferred. The anion exchange chromatography can be conducted, for instance, as described in Example 3. Briefly, about 50 ml of the void volume fraction pool from the size exclusion chromatography step can be loaded onto the AIEX column at a flow rate of 3.0 ml/min. Following a washing step using, for instance, 20 mM Tris, pH 6.5, 5 mM DTT to remove unbound material, protein can be eluted with a single step of 8 column volumes of the following buffer (20 mM Tris, pH 6.5, 5 mM DTT, 1.0 M NaCl) The flow-through from the AIEX run can be loaded back onto the Q Sepharose column and eluted as described above to increase the yield. This two step technique (size exclusion followed by anion-exchange chromatography) effectively separates PCV-2 ORF2 antigen from most of the other protein components of the culture harvest.

The PCV-2 antigenic composition obtained according to the method described above, or the PCV-2 antigen used in step i) of the method described above, can be combined with at least one additional antigen, preferably a viral or bacterial antigen, and even more preferably, a viral or bacterial antigen from at least one other disease-causing organism in swine. The additional antigen can be any one of those disclosed in the international patent application WO2007/094893 (the contents and teachings of which are hereby incorporated by reference). Briefly, the additional antigens can be antigens of any other disease-causing organisms of swine. Preferably the "another disease-causing organisms" of swine are selected from the group consisting of: *Actinobacillus pleuropneumonia* (1); Adenovirus (2); Alphavirus such as Eastern equine encephalomyelitis viruses (3); *Bordetella bronchiseptica* (4); *Brachyspira* spp. (5), preferably *B. hyodyentheriae* (6); *B. piosicoli* (7), *Brucella suis*, preferably biovars 1, 2, and 3 (8); Classical swine fever virus (9); *Clostridium* spp. (10), preferably *Cl. difficile* (11), *Cl. perfringens* types A, B, and C (12), *Cl. novyi* (13), *Cl. septicum* (14), *Cl. tetani* (15); Coronavirus (16), preferably Porcine Respiratory Corona virus (17); *Eperythrozoonosis suis* (18); *Erysipelothrix rhsiopathiae* (19) *Escherichia coli* (20); *Haemophilus parasuis*, preferably subtypes 1, 7 and 14 (21) Hemagglutinating encephalomyelitis virus (22); Japanese Encephalitis Virus (23); *Lawsonia intracellularis* (24) *Leptospira* spp. (25), preferably *Leptospira australis* (26); *Leptospira canicola* (27); *Leptospira grippotyphosa* (28); *Leptospira icterohaemorrhagicae* (29); and *Leptospira interrogans* (30); *Leptospira pomona* (31); *Leptospira tarassovi* (32); *Mycobacterium* spp. (33) preferably *M. avium* (34), *M. intracellulare* (35) and *M. bovis* (36); *Mycoplasma hyopneumoniae* (37); *Pasteurella multocida* (38); Porcine cytomegalovirus (39); Porcine Parvovirus (40); Porcine Reproductive and Respiratory Syndrome Virus (41); Pseudorabies virus (42); Rotavirus (43); *Salmonella* spp. (44), preferably *S. thyhimurium* (45) and *S. choleraesuis* (46); *Staph. hyicus* (47); *Staphylococcus* spp. (48) preferably *Streptococcus* spp. (49), preferably *Strep. suis* (50); Swine herpes virus (51); Swine Influenza Virus (52); Swine pox virus (53); Swine pox virus (54); Vesicular stomatitis virus (55); Virus of vesicular exanthema of swine (56); *Leptospira Hardjo* (57); and/or *Mycoplasma hyosynoviae* (58).

Thus, according to a further aspect of the present invention, the present invention provides a method of producing a PCV-2 antigenic composition comprising the steps of i) obtaining a PCV-2 antigen in a first liquid; ii) removing at least a portion of the first liquid from the PCV-2 antigen; and combining the PCV-2 antigen with at least one additional antigen, preferably a viral or bacterial antigen, and more preferably a viral or bacterial antigen from at least one other disease-causing organism in swine. Preferably, the PCV-2 antigen comprises the ORF-2 protein of PCV-2, more preferably recombinant ORF-2 protein of PCV-2, and still more preferably virus like particles of ORF-2 protein. Preferably, the portion of the first liquid is removed from the PCV-2 antigen by an exchange of a portion of the first liquid against a second liquid. The exchange is preferably done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably, the liquid addition step and concentration step are performed multiple times, preferably two times, and even more preferably three times. In such cases, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- or ultrafiltration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. Further purification to obtain a purified PCV-2 antigen can be done as described above.

In preferred forms, the method of producing a PCV-2 antigenic composition described above further comprises the steps of i) obtaining a PCV-2 antigen in a first liquid wherein the PCV-2 antigen is obtained via a viral vector, preferably a recombinant baculovirus viral vector, containing and expressing the PCV-2 antigen, preferably, PCV-2 ORF-2, and wherein the PCV-2 antigen comprises the ORF-2 protein of PCV-2, more preferably recombinant ORF-2 protein of PCV-2, and still more preferably virus like particles of ORF-2 protein; ii) removing at least a portion of the first liquid from the PCV-2 antigen; iii) inactivating the recombinant baculovirus viral vector with a DNA inactivating agent, preferably in the presence of about 1 to about 20 mM of binary ethylenimine; iv) adding an amount of a neutralizing agent that neutralizes the inactivating agent, the amount of neutralizing agent being equivalent to the amount of the inactivating agent, wherein the neutralizing agent preferably comprises a sodium thiosulfate solution preferably concentrated to a final concentration of about 1 to about 20 mM and wherein the inactivating agent preferably comprises BEI; and v) admixing the PCV-2 antigen obtained in step iv) with a further component selected from the group consisting of pharmaceutically acceptable carriers, adjuvants, diluents, excipients, and combinations thereof.

In a further aspect of the method, the at least one additional antigen is a viral antigen, preferably an antigen from Porcine Reproductive and Respiratory Syndrome Virus. Even more preferably, the Porcine Reproductive and Respiratory Syndrome Virus antigen comprises a live virus, and still more preferably a modified live virus, even more preferably a modified live attenuated virus. Still more preferably, the modified live Porcine Reproductive and Respiratory Syndrome Virus antigen comprises a modified live virus strain of ATCC Accession Number VR 2332, and still more preferably comprises INGELVAC® PRRS MLV. Thus, according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, and combining the PCV-2 antigen with an antigen from Porcine Reproductive and Respiratory Syndrome Virus. Preferably, the Porcine Reproductive and Respiratory Syndrome Virus antigen comprises a live virus, still more preferably a modified live virus, and even more preferably a modified live attenuated virus. Still more preferably, the modified live Porcine Reproductive and Respiratory Syndrome Virus antigen comprises a modified live virus strain of ATCC Accession Number VR 2332, and still more preferably comprises INGELVAC® PRRS MLV. Preferably the PCV-2 antigen comprises the ORF-2 protein of PCV-2, more preferably recombinant ORF-2 protein of PCV-2, and still more preferably virus like particles of ORF-2 protein. Preferably, the portion of the first liquid is removed from the PCV-2 antigen by an exchange of a portion of the first liquid against a second liquid. The exchange is preferably done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably, the liquid addition step and concentration step are performed multiple times, preferably two times, even more preferably three times. In such case, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- and/or ultrafiltration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. Further purification to obtain a purified PCV-2 antigen can be done as described above.

In a further aspect of the present application, the at least one additional antigen is a bacterial antigen, preferably *Mycoplasma hyopneumoniae*. Preferably the *Mycoplasma hyopneumoniae* antigen is a bacterin, and more preferably, the *Mycoplasma hyopneumoniae* bacterin is INGELVAC® MYCOFLEX. Thus, according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, and combining the PCV-2 antigen with a bacterial antigen, preferably *Mycoplasma hyopneumoniae*. Preferably the *Mycoplasma hyopneumoniae* antigen is a bacterin, and more preferably, the *Mycoplasma hyopneumoniae* bacterin is INGELVAC® MYCOFLEX. Preferably the PCV-2 antigen comprises the ORF-2 protein of PCV-2, more preferably recombinant ORF-2 protein of PCV-2, and still more preferably virus like particles of ORF-2 protein. Preferably, the portion of the first liquid is removed from the PCV-2 antigen by an exchange of a portion of the first liquid against a second liquid. The exchange is preferably done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably, the liquid addition step and concentration step are performed multiple times, preferably two times, and even more preferably three times. In such cases, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- or ultrafiltration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. Further purification to obtain a purified PCV-2 antigen can be done as described above.

In a further aspect of the present application, the at least one additional antigen includes a viral antigen, preferably a Porcine Reproductive and Respiratory Syndrome Virus antigen, as described above, and a bacterial antigen, preferably a *Mycoplasma hyopneumoniae* antigen, as described above. Preferably, the Porcine Reproductive and Respiratory Syndrome Virus antigen comprises a live virus, more preferably a modified live virus, and still more preferably, comprises a modified live virus strain of ATCC Accession Number VR 2332, and still more preferably comprises INGELVAC® PRRS MLV. Preferably, the *Mycoplasma hyopneumoniae* antigen is a bacterin, and more preferably, the *Mycoplasma hyopneumoniae* bacterin is INGELVAC® MYCOFLEX Thus, according to a further aspect, the present application provides a method of producing a PCV-2 antigenic composition comprising the steps of i) obtaining a first liquid containing a PCV-2 antigen, ii) removing at least a portion of the first liquid from the PCV-2 antigen, and combining the PCV-2 antigen with a viral antigen, preferably a Porcine Reproductive and Respiratory Syndrome Virus antigen, as described above, and a bacterial antigen, preferably a *Mycoplasma hyopneumoniae* antigen, as described above. Preferably, the Porcine Reproductive and Respiratory Syndrome Virus antigen comprises a live virus, more preferably a modified live virus, and still more preferably, comprises a modified live virus strain of ATCC Accession Number VR 2332, and still more preferably comprises INGELVAC® PRRS MLV. Preferably, the *Mycoplasma hyopneumoniae* antigen is a bacterin, and more preferably, the *Mycoplasma hyopneumoniae* bacterin is INGELVAC® MYCOFLEX. Preferably the PCV-2 antigen comprises the ORF-2 protein of PCV-2, more preferably recombinant ORF-2 protein of PCV-2, and still more preferably virus like particles of ORF-2 protein. Preferably, the portion of the first liquid is removed from the PCV-2 antigen by an exchange of a portion of the first liquid against a second liquid. The exchange is preferably done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably, the liquid addition step and concentration step are performed multiple times, preferably two times, and even more preferably three times. In such cases, not only the first liquid is removed, but also a mixture of the first and second liquid. Preferably the liquid addition step is performed substantially simultaneously or sequentially as described above. When the concentrating step and liquid addition step are performed sequentially, the order of the steps does not matter. Moreover, the concentration step is preferably done by filtration—preferably by dia- and/or ultrafiltration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. Further purification to obtain a purified PCV-2 antigen can be done as described above.

The present application does not only provide methods of producing PCV-2 antigenic compositions, it also relates to a PCV-2 antigenic composition. Thus, according to a further aspect the present patent application further provides a PCV-2 antigenic composition characterized in such that the PCV-2 antigenic composition causes a loss of less than 1 log $TCID_{50}$ of a live virus or less than 1 log CFU per ml of a live bacterium, when the live virus or live bacterium is mixed with the PCV-2 antigenic composition and incubated for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, and most preferably for more than 2 years. More preferably, the PCV-2 antigenic composition produced by the method described herein causes a loss of a live virus or less than 0.9 log CFU per ml of a live bacterium, when the live virus or live bacterium is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, and most preferably for more than 2 years. Even more preferably, the PCV-2 antigenic composition causes a loss of less than 0.7 log TCID$_{50}$ per ml of a live virus or less than 0.7 log CFU per ml of a live bacterium, when the live virus or live bacterium is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, and most preferably for more than 2 years. Still more preferably, the PCV-2 antigenic composition causes a loss of less than 0.5 log TCID$_{50}$ per ml of a live virus or less than 0.5 log CFU per ml of a live bacterium, when the live virus or live bacterium is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, and most preferably for more than 2 years. Even more preferably, the PCV-2 antigenic composition causes a loss of less than 0.3 log TCID$_{50}$ per ml of a live virus or less than 0.3 log CFU per ml of a live bacterium, when the live virus or live bacterium is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, and most preferably for more than 2 years. The live virus can be any live virus, but preferably the live virus is the PRRS virus, preferably the PRRS virus having the ATCC accession number VR 2332. The live bacterium can be any bacterium, but is preferably the *Mycoplasma hyopneumonia* bacterium, preferably the J-strain of *Mycoplasma hyopneumonia*. The TCID$_{50}$ per ml can be estimated by a standard in vitro titration assay which allow the estimation of the amount of a live virus. The CFU per ml can be determined also by a standard in vitro titration assay which allows the estimation of the amount of a live bacterium. The term "per ml" preferably refers to 1 ml of a fluid.

In a further aspect, the PCV-2 antigenic composition described above comprises a further component selected from the group consisting of pharmaceutically acceptable carriers, adjuvants, diluents, excipients, and combinations thereof. Preferably, the further component is an adjuvant, even more preferably wherein the adjuvant is a polymer of acrylic or methacrylic acid, and still more preferably wherein the adjuvant is Carbomer. Preferably, the adjuvant is added in an amount of about 100 µg to about 10 mg per dose. Even more preferably the adjuvant is added in an amount of about 100 µg to about 10 mg per dose. Still more preferably the adjuvant is added in an amount of about 500 µg to about 5 mg per dose. Still more preferably the adjuvant is added in an amount of about 750 µg to about 2.5 mg per dose. Most preferably the adjuvant is added in an amount of about 1 mg per dose.

The present application does not only provide methods of producing PCV-2 antigenic compositions and/or the PCV-2 antigenic compositions as defined above, it also relates to a PCV-2 antigenic composition that is obtainable by any of the methods described herein. Thus, in a further aspect the present application relates to a PCV-2 antigenic composition that is obtained by a method comprising the steps of i) obtaining a first liquid containing a PCV-2 antigen, ii) removing at least a portion of the first liquid from the PCV-2 antigen. Preferably the PCV-2 antigen is used as or in the PCV-2 antigenic composition. The term "a PCV-2 antigenic composition obtained by a method provided herein" also means that the PCV-2 antigenic composition is obtainable by a method provided herein. According to a further aspect, the present application also relates to the PCV-2 antigenic composition that is obtained by removing the portion of the first liquid from the PCV-2 antigen by an exchange of the portion of the first liquid against a second liquid, wherein the second liquid is different from the first liquid. Thus according to a further aspect, the present application relates to a PCV-2 antigenic composition obtained by a method comprising the steps of i) obtaining a first liquid containing a PCV-2 antigen, ii) removing at least a portion of the first liquid from the PCV-2 antigen, wherein the portion of the first liquid is removed from the PCV-2 antigen by an exchange of the portion of the first liquid against a second liquid, wherein the second liquid is different from the first liquid. Preferably the exchange of the portion of the first liquid with the second liquid comprises the steps of a) adding the second liquid to the first liquid which contains the PCV-2 antigen and b) concentrating the PCV-2 antigen by removing a portion of the first and second liquids from the PCV-2 antigen.

According to a further aspect, the PCV-2 antigenic composition is preferably obtained by a method wherein the portion of the first liquid is removed from the PCV-2 antigen by a filtration step utilizing a filter. However, any other methods known to a person skilled in the art can be used to remove the portion of the first and second fluid from the PCV-2 antigen, for instance centrifugation and/or chromatography. However, filtration is most preferred. Preferred filtration methods to remove the portion of the first fluid comprise ultra- and/or dia-filtration. The concentrating step and the liquid addition step of the method as described herein can be performed substantially simultaneously or alternatively, the concentrating step and the liquid addition step are performed sequentially. Thus according to a further aspect, the present application relates to a PCV-2 antigenic composition obtained by a method comprising the steps of i) obtaining a first liquid containing a PCV-2 antigen, ii) removing at least a portion of the first liquid from the PCV-2 antigen, wherein the portion of the first liquid is removed from the PCV-2 antigen by an exchange of the portion of the first liquid against a second liquid, wherein the second liquid is different from the first liquid. Preferably the exchange of the portion of the first liquid with the second liquid comprises the steps of a) adding the second liquid to the first liquid which contains the PCV-2 antigen and b) concentrating the PCV-2 antigen by removing a portion of the first and second liquids from the PCV-2 antigen, wherein the liquid addition step is performed substantially simultaneously or sequentially. When the concentrating step and liquid addition step are performed sequentially, the order of the steps does not matter. For example, in a further aspect, the liquid addition step occurs prior to the concentrating step and in an alternative aspect, the concentrating step occurs prior to the liquid addition step.

In a further aspect, the present application relates to a PCV-2 antigenic composition that can be obtained using a method described herein, wherein the liquid addition step and the concentrating step, regardless of the order in which they are performed, can be performed multiple times. For example, each of these respective steps can be performed at least two, at least three, at least four, at least five, at least 10, up to as many times as desired. In one aspect, the concentrating step and the liquid addition step are each performed at least two times. In another aspect, the concentrating step and the liquid addition step are each performed at least three times.

In a further aspect of the present application, the PCV-2 antigenic composition of the present invention is obtained as described above, wherein filtration is the preferred method to remove a portion of the first liquid, or in case of multiple removing steps as described above, a portion of the mixture of the first and the second fluid from the PCV-2 antigen. The filter can be any conventional filter in the art. Preferably, the filter includes a semi-permeable membrane. In a further preferred form, the semi-permeable membrane has an average pore size that is smaller than the PCV-2 antigen to thereby prevent passage of at least 90% of the PCV-2 antigen through the semi-permeable membrane pores and withhold the PCV-2 antigen by the filter. In a further aspect, the filter has an average pore size which prevents passage of at least 90% of proteins of 50 kDa to 500 kDa in size, more preferably, the filter has an average pore size which prevents passage of at least 90% of proteins of 75 kDa to 400 kDa in size, and most preferably, the filter has an average pore size which prevents passage of at least 90% of proteins of 100 kDa to 300 kDa in size. This pore size is preferred, when the PCV-2 antigen is produced as whole virus or as virus like particles. In a still further aspect, the semi-permeable membrane includes a material selected from the group consisting of polysulfone, polyethersulfone, and regenerated cellulose. However, any other material can be used, which allows removing of a portion of the first fluid, and in case of a multiple process step, removing of a mixture of the first and the second fluid from the PCV-2 antigen. In a further aspect, the filter is selected from the group consisting of a hollow fiber membrane ultra filtration cartridge, flat sheets, or a cassette, with a hollow fiber membrane ultra filtration cartridge being particularly preferred.

Thus, according to a further aspect, the present application relates to a PCV-2 antigenic composition that is obtained using the methods as described above, wherein the filter preferably is or comprises a semi-permeable membrane. Preferably, the semi-permeable membrane has an average pore size that is smaller than the PCV-2 antigen and prevent passage of at least 90% of the PCV-2 antigen through the semi-permeable membrane pores. Preferably the average pore size of the semi-permeable membrane prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. As described above, the removing step in general includes the exchange of the portion of the first fluid against a portion of the second fluid comprises the steps of a) adding the second liquid to the first liquid which contains the PCV-2 antigen and b) concentrating the PCV-2 antigen by removing a portion of the first and second liquids from the PCV-2 antigen, wherein the liquid addition step and concentration step are performed multiple times, for instance, two times, three times, 5 times, 10 times, etc. Preferably, the liquid addition step and concentration step are performed two times, most preferably three times.

The concentration step of the method provided herein to obtain the PCV-2 antigenic composition is performed such that the PCV-2 antigen is concentrated from 3× to 50× in comparison to the volume of the first liquid. More preferably, the concentrating step is done in such that the PCV-2 antigen is concentrated 4× to 20× in comparison to the volume of the first liquid. Most preferably, concentration step is done in such that the PCV-2 antigen is concentrated from 7× to 10× in comparison to the volume of the first liquid. Thus according to a further aspect, the present application relates to a PCV-2 antigenic composition obtained by a method described above, wherein the PCV-2 antigen is concentrated from 3× to 50×, preferably from 4× to 20×, and even more preferably from 7× to 10× in comparison to the volume of the first liquid. Preferably, the portion of the first fluid is removed from the PCV-2 antigen by an exchange of the portion of the first liquid against a second liquid comprising the steps of a) adding the second liquid to the first liquid which contains the PCV-2 antigen and b) concentrating the PCV-2 antigen from 3× to 50×, preferably from 4× to 20×, and even more preferably from 7× to 10× in comparison to the volume of the first liquid by removing a portion of the first and second liquids from the PCV-2 antigen. Preferably the liquid addition step is performed substantially simultaneously or sequentially with the concentrating step. When the concentrating step and liquid addition step are performed sequentially, the order of the steps does not matter. Moreover, the concentration step is preferably done by filtration—preferably dia- and/or ultra-filtration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores. Preferably the average pore size of the semi-permeable membrane prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

Preferably, further purification to obtain PCV-2 antigenic composition comprising a purified PCV-2 antigen as defined herein, can be achieved by performing further purification step comprising iii) purifying the harvest of step ii) comprising the PCV-2 antigen (of any methods described herein), which is obtained after the removal of a portion of the first liquid, by a chromatography a step. In order to obtain a higher purity grade a second chromatography step can be done, which however is different from the first one.

For instance if the first purification step/chromatography step is size exclusion (gel filtration) the second should different from that e.g. an affinity chromatography, ion exchange chromatography, etc. Preferably, if the first step to purify PCV-2 antigen, preferably to purify PCV-2 ORF2 antigen is a size exclusion (gel filtration) chromatography, the second step can be ion-exchange chromatography, preferably anion-exchange chromatography (AIEX) A preferred anion-exchange chromatography matrix for the purification of PCV-2 antigen, preferably the PCV-2 ORF2 antigen is Q Sepharose. In a small scale of about 50 ml, use of 5 ml HiTrap Q Sepharose HP columns are most preferred. The anion exchange chromatography can be conducted, for instance, as described in Example 3. Briefly, about 50 ml of the void volume fraction pool from the size exclusion chromatography step can be loaded onto the AIEX column at a flow rate of 3.0 ml/min. Following a washing step using, for instance, 20 mM Tris, pH 6.5, 5 mM DTT to remove unbound material, protein can be eluted with a single step of 8 column volumes of the following buffer (20 mM Tris, pH 6.5, 5 mM DTT, 1.0 M NaCl) The flow-through from the AIEX run can be loaded back onto the Q Sepharose column and eluted as described above to increase the yield. This two step technique (size exclusion followed by anion-exchange chromatography) effectively separates PCV-2 ORF2 antigen from most of the other protein components of the culture harvest.

In a further aspect, the virucidal activity of the PCV-2 antigenic composition produced by the methods described herein is reduced by at least 10% as compared to the liquid that has not undergone the method. More preferably, the virucidal activity of the PCV-2 antigenic composition is reduced by at least 50% as compared to the first liquid that has not undergone the method. Still more preferably, the virucidal activity of the PCV-2 antigenic composition is reduced by at least 70% as compared to the first liquid that has not undergone the method.

Thus according to a further aspect, the present application relates to PCV-2 antigenic composition obtained by a method comprising the steps of i) obtaining a first liquid containing a PCV-2 antigen, ii) removing at least a portion of the first liquid from the PCV-2 antigen, wherein the virucidal activity—preferably in respect to PRRS virus—of the PCV-2 antigenic composition obtained after step ii) is reduced by at least 10%, preferably at least 50%, more preferably at least 70%, even more preferably at least 90% as compared to that of the first liquid. Preferably, the portion of the first liquid having virucidal activity is removed from the PCV-2 antigen by an exchange of a portion of the first liquid against a second liquid. The exchange is preferably done in such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably the liquid addition step is performed substantially simultaneously or sequentially with the concentrating step as described above. When the concentrating step and liquid addition step are performed sequentially, the order of the steps does not matter. Moreover, the concentration step is preferably done by filtration—preferably by dia- and/or ultra-filtration, utilizing a filter, which preferably contains a semi-permeable membrane. The semi-permeable membrane preferably has an average pore size that is smaller than the PCV-2 antigen and prevent passage of at least 90% of the PCV-2 antigen through the semi-permeable membrane pores. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles. Further purification to obtain a purified PCV-2 antigen can be done as described above.

According to a further aspect, the present application relates to a PCV-2 antigenic composition obtained by a method described herein, wherein the PCV-2 antigenic composition causes a loss of less than 1 log $TCID_{50}$—preferably per ml—, preferably less than 0.9 log $TCID_{50}$,—preferably per ml—, even more preferably less than 0.7 log $TCID_{50}$—preferably per ml—, even more preferably less than 0.5 log $TCID_{50}$—preferably per ml—, most preferably less than 0.3 log $TCID_{50}$—preferably per ml—of a live virus, preferably of a live PRRSV or less than 1 log CFU—preferably per ml—, preferably less than 0.9 log CFU—preferably per ml—, even more preferably less than 0.7 log CFU—preferably per ml—, even more preferably less than 0.5 log CFU—preferably per ml—, most preferably less than 0.3 log CFU—preferably per ml—of a live bacterium, preferably of *Mycoplasma hyopneumoniae*, when the live virus, preferably PRRSV or live bacterium, preferably *Mycoplasma hyopneumoniae* is mixed and incubated with the PCV-2 antigenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, and most preferably for more than 2 years. The live virus can be any live virus, but preferably the live virus is the PRRS virus, preferably the PRRS virus having the ATCC accession number VR 2332. The live bacterium can be any bacterium, but is preferably the *Mycoplasma hyopneumoniae* bacterium, preferably the J-strain of *Mycoplasma hyopneumoniae*. The $TCID_{50}$ per ml can be estimated by a standard in vitro titration assay which allow the estimation of the amount of a live virus. The CFU per ml can be determined also by a standard in vitro titration assay which allows the estimation of the amount of a live bacterium. The term "per ml" preferably refers to 1 ml of a fluid.

In a further aspect, the present patent application relates to a PCV-2 antigenic composition that is obtained by a method described above, further comprising the step of harvesting the PCV-2 antigen remaining after step ii). This harvesting can be done in any conventional manner. In a particularly preferred manner of harvesting, the portion of the first liquid is removed from the PCV-2 antigen via a filtration step and the PCV-2 antigen is recovered or harvested from the filter retard.

In a further aspect, the PCV-2 antigenic composition obtained by any of the methods described herein is admixed with a further component selected from the group consisting of pharmaceutically acceptable carriers, adjuvants, diluents, excipients, and combinations thereof. Preferably, the further component is an adjuvant, even more preferably wherein the adjuvant is a polymer of acrylic or methacrylic acid, and still more preferably wherein the adjuvant is Carbomer.

Thus, according to a further aspect, the present application provides a PCV-2 antigenic composition obtained by a method described above, further comprising the step of admixing the PCV-2 antigen obtained by the method described herein with a further component selected from the group consisting of pharmaceutically acceptable carriers, adjuvants, diluents, excipients, and combinations thereof. Preferably the further component is an adjuvant, even more preferably wherein the adjuvant is a polymer of acrylic or methacrylic acid, and still more preferably wherein the adjuvant is Carbomer. Preferably, the adjuvant is added in an amount of about 100 µg to about 10 mg per dose. Even more preferably the adjuvant is added in an amount of about 100 µg to about 10 mg per dose. Still more preferably the adjuvant is added in an amount of about 500 µg to about 5 mg per dose. Still more preferably the adjuvant is added in an amount of about 750 µg to about 2.5 mg per dose. Most preferably the adjuvant is added in an amount of about 1 mg per dose.

In a further aspect, the PCV-2 antigenic composition described above comprises the ORF-2 protein of PCV-2, more preferably recombinant ORF-2 protein of PCV-2, and still more preferably virus like particles of ORF-2 protein. Thus, according to a further aspect of the present application, the present application provides a PCV-2 antigenic composition obtained by a method described above, wherein the PCV-2 antigen comprises the ORF-2 protein of PCV-2, more preferably recombinant ORF-2 protein of PCV-2, and still more preferably virus like particles of ORF-2 protein.

As mentioned above, the PCV-2 antigen used in the method described herein can be obtained by any method known in the art. Preferably, the PCV-2 antigen is obtained via a viral vector, preferably a recombinant baculovirus viral vector, containing and expressing the PCV-2 antigen, preferably, PCV-2 ORF-2. In preferred forms, the PCV-2 antigen is obtained following the procedures described in WO2006/072065 (the teachings and content of which were previously incorporated by reference). Thus, according to a further aspect of the present application, the present application provides a PCV-2 antigenic composition obtained by a method described above, wherein the PCV-2 antigen is obtained via a viral vector, preferably a recombinant baculovirus viral vector, containing and expressing the PCV-2 antigen, preferably, PCV-2 ORF-2, and wherein the PCV-2 antigen comprises the ORF-2 protein of PCV-2, more preferably recombinant ORF-2 protein of PCV-2, and still more preferably virus like particles of ORF-2 protein.

In a further aspect of the present application, the PCV-2 antigenic composition is obtained by the method described above and further comprises the step of inactivating the recombinant baculovirus viral vector with a DNA inactivating agent, preferably in the presence of about 1 to about 20 mM of binary ethylenimine. In preferred forms, the method further comprises the step of adding an amount of an agent that neutralizes the DNA inactivating agent, the amount being equivalent to the amount of the DNA inactivating agent wherein the agent that neutralizes the DNA inactivating agent comprises a sodium thiosulfate solution concentrated to a final concentration of about 1 to about 20 mM and wherein the DNA inactivating agent is BEI. Preferably, the inactivating step is performed after at least a portion of the first liquid is removed from the PCV-2 antigen.

In a further aspect of the present application, the PCV-2 antigenic composition is obtained by the method described above further comprising the steps of admixing the PCV-2 antigen obtained after the inactivating and neutralizing steps. Thus, according to a further aspect, the present application provides a PCV-2 antigenic composition obtained by a method described above comprising the steps of i) obtaining a PCV-2 antigen in a first liquid; ii) removing at least a portion of the first liquid from the PCV-2 antigen; iii) inactivating the recombinant baculovirus viral vector with a DNA inactivating agent, preferably in the presence of about 1 to about 20 mM of binary ethylenimine; iv) adding an amount of a neutralizing agent that neutralizes the inactivating agent, the amount of neutralizing agent being equivalent to the amount of the inactivating agent, wherein the neutralizing agent preferably comprises a sodium thiosulfate solution preferably concentrated to a final concentration of about 1 to about 20 mM and wherein the inactivating agent preferably comprises BEI; and, preferably step v), comprising admixing the PCV-2 antigen obtained in step iv) with a further component selected from the group consisting of pharmaceutically acceptable carriers, adjuvants, diluents, excipients, and combinations thereof.

In a further aspect of the present application, the PCV-2 antigenic composition described above, preferably obtained by the methods described above, further comprises at least one additional antigen, preferably a viral or bacterial antigen, and more preferably a viral or bacterial antigen from at least one other disease-causing organism in swine. In a further aspect the at least one additional antigen is Porcine Reproductive and Respiratory Syndrome Virus. Even more preferably, the Porcine Reproductive and Respiratory Syndrome Virus antigen comprises a live virus, and still more preferably a modified live virus. Still more preferably, the modified live Porcine Reproductive and Respiratory Syndrome Virus antigen comprises a modified live virus strain of ATCC Accession Number VR 2332, and still more preferably comprises INGELVAC® PRRS MLV. In a further aspect of the present application, the at least one additional antigen is *Mycoplasma hyopneumoniae*. Preferably the *Mycoplasma hyopneumoniae* antigen is a bacterin, and more preferably, the *Mycoplasma hyopneumoniae* bacterin is INGELVAC® MYCOFLEX. In a further aspect of the present application, the PCV-2 antigenic composition described above, preferably obtained by the methods described above further comprises Porcine Reproductive and Respiratory Syndrome Virus antigen, preferably a modified live Porcine Reproductive and Respiratory Syndrome Virus, still more preferably, the Porcine Reproductive and Respiratory Syndrome Virus having the ATCC Accession Number VR 2332, or the Porcine Reproductive and Respiratory Syndrome Virus included in INGELVAC® PRRS MLV or INGELVAC® PRRS ATP. In a further aspect of the present application, the PCV-2 antigenic composition described above, preferably obtained by the methods described above further comprises *Mycoplasma hyopneumoniae*, preferably *Mycoplasma hyopneumoniae* bacterin, and more preferably INGELVAC® MYCOFLEX or the *Mycoplasma hyopneumoniae* bacterin included in INGELVAC® MYCOFLEX. In a further aspect, the PCV-2 antigenic composition described herein, comprises a Porcine Reproductive and Respiratory Syndrome Virus, preferably any one of those described above and a *Mycoplasma hyopneumoniae*, preferably any one of those described above.

When the PCV-2 antigenic composition comprising the at least one additional antigen from at least one other disease-causing organism in swine as described above, preferably Porcine Reproductive and Respiratory Syndrome Virus and/or *Mycoplasma hyopneumoniae* antigen is obtained by a method described herein, the method comprises the steps of i) obtaining a PCV-2 antigen in a first liquid; ii) removing at least a portion of the first liquid from the PCV-2 antigen; and combining the PCV-2 antigen with at least one additional antigen, preferably a viral or bacterial antigen, and more preferably a viral or bacterial antigen from at least one other disease-causing organism in swine. Preferably, the PCV-2 antigen comprises the ORF-2 protein of PCV-2, more preferably recombinant ORF-2 protein of PCV-2, and still more preferably virus like particles of ORF-2 protein. Preferably, the portion of the first liquid is removed from the PCV-2 antigen by an exchange of a portion of the first liquid against a second liquid. The exchange is preferably done such that it comprises the steps of a) adding the second liquid to the first liquid which contains the PCV-2 antigen and b) concentrating the PCV-2 antigen, preferably from 3× to 50×, even more preferably from 4× to 20×, and even more preferably from 7× to 10× in comparison to the volume of the first liquid by removing a portion of the first and second liquids from the PCV-2 antigen. Preferably, the liquid addition step and concentration step are performed multiple times, preferably two times, even more preferably three times. In such cases, not only the first liquid is removed, but also a mixture of the first and second liquid. Preferably each liquid addition step is performed substantially simultaneously or sequentially as described above. When the concentrating step and liquid addition step are performed sequentially, the order of the steps does not matter. Moreover, the concentration step is preferably done by filtration—preferably by dia- or ultrafiltration, utilizing a filter, which preferably contains a semi-permeable membrane. The semi-permeable membrane preferably has an average pore size that is smaller than the PCV-2 antigen and prevents passage of at least 90% of the PCV-2 antigen through the semi-permeable membrane pores and withholds the PCV-2 antigen within the filter for harvesting or recovery. Preferably the average pore size of the semi-permeable membrane or of any other filter that is used herein, prevents passage of at least 90% of proteins of 50 kDa to 500 kDa in size, more preferably, at least 90% of proteins of 75 kDa to 400 kDa in size, and most preferably at least 90% of proteins of 100 kDa to 300 kDa in size. This pore size is preferred, when the PCV-2 antigen is produced as whole virus or as virus like particles.

The present invention as defined above, provides new methods of producing a PCV-2 antigen and immunogenic compositions comprising a PCV-2 antigen, wherein the PCV-2 antigen shows a reduced virucidal activity and/or increased immunogenicity (each as defined herein), wherein the method comprises the steps of i) obtaining a first liquid containing a PCV-2 antigen, ii) removing at least a portion of the first liquid from the PCV-2 antigen. Moreover, the present invention also provides a PCV-2 antigen as well as immunogenic compositions comprising such PCV-2 antigen showing a reduced virucidal activity and/or increased immunogenicity (each as defined herein). According to a further aspect, the PCV-2 antigen as well as the immunogenic compositions comprising a purified PCV-2 antigen showing a reduced virucidal activity and/or increased immunogenicity can alternatively be obtained by the following method (II). The purified PCV-2 antigen according to the invention, preferably the purified PCV-2 ORF2 antigen, can be obtained by the purification of a PCV-2 virus preparation, in particular by the purification of the whole virus. Whole virus preparations are described for instance in WO 99/18214 or WO 03/049703. Moreover, purified PCV-2 antigen can also be obtained by the purification of a recombinant expressed PCV-2 antigen, preferably by the purification of a recombinant PCV-2 ORF2 antigen. Expression systems for the production of recombinant PCV-2 antigen, preferably for the production of recombinant PCV-2 ORF2 antigens are well known in the art and include, but not limited to, bacterial expression systems, yeast expression systems, insect cell or mammalian expression systems. Vectors and methods for making and/or using vectors (or recombinants) for the expression of the PCV-2 antigens are described in the application elsewhere.

Preferred cells are those susceptible for infection with an appropriate recombinant viral vector, containing a PCV-2 ORF2 DNA and expressing the PCV-2 ORF2 protein. Preferably the cells are insect cells, and more preferably, they include the insect cells sold under the trademark SF+ insect cells (Protein Sciences Corporation, Meriden, Conn.). Preferred cell cultures have a cell count between about 0.3-2.0×10$^6$ cells/mL, more preferably from about 0.35-1.9×10$^6$ cells/mL, still more preferably from about 0.4-1.8×10$^6$ cells/mL, even more preferably from about 0.45-1.7×10$^6$ cells/mL, and most preferably from about 0.5-1.5×10$^6$ cells/mL.

Preferred viral vectors include baculovirus such as BaculoGold (BD Biosciences Pharmingen, San Diego, Calif.), in particular provided that the production cells are insect cells. Although the baculovirus expression system is preferred, it is understood by those of skill in the art that other expression systems, including those described above will work for purposes of the present invention, namely the expression of PCV-2 ORF2 antigen.

Appropriate growth media will also be determinable by those of skill in the art with a preferred growth media being serum-free insect cell media such as Excell 420 (JRH Biosciences, Inc., Lenexa, Kans.) and the like.

The recombinant viral vector containing the PCV-2 ORF2 DNA sequences has a preferred multiplicity of infection (MOI) of between about 0.03-1.5, more preferably from about 0.05-1.3, still more preferably from about 0.09-1.1, and most preferably from about 0.1-1.0, when used for the infection of the susceptible cells. Preferably the MOIs mentioned above relates to one mL of cell culture fluid. Preferably, the method described herein comprises the infection of 0.35-1.9×10$^6$ cells/mL, still more preferably of about 0.4-1.8×10$^6$ cells/mL, even more preferably of about 0.45-1.7×10$^6$ cells/mL, and most preferably of about 0.5-1.5×10$^6$ cells/mL with a recombinant viral vector containing a PCV-2 ORF2 DNA and expressing the PCV-2 ORF2 antigen protein having a MOI (multiplicity of infection) of between about 0.03-1.5, more preferably from about 0.05-1.3, still more preferably from about 0.09-1.1, and most preferably from about 0.1-1.0.

The infected cells are then incubated over a period of up to ten days, more preferably from about two days to about ten days, still more preferably from about four days to about nine days, and most preferably from about five days to about eight days. Preferred incubation conditions include a temperature between about 22-32° C., more preferably from about 24-30° C., still more preferably from about 25-29° C., even more preferably from about 26-28° C., and most preferably about 27° C. Preferably, the SF+ cells are observed following inoculation for characteristic baculovirus-induced changes. Such observation may include monitoring cell density trends and the decrease in viability during the post-infection period. It was found that peak viral titer is observed 3-5 days after infection and peak PCV-2 ORF2 antigen production in cells is obtained between days 5 and 8 post infection and/or when cell viability decreases to less than 10%.

The PCV-2 ORF2 antigen can be purified from the harvest by standard methods known to a person skilled in the art, for example by those described in Protein purification methods—a practical approach (E. L. V. Harris and S. Angal, eds., IRL Press at Oxford University Press). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, etc.

The recovery process of the PCV-2 antigen, preferably the PCV-2 ORF2 antigen, preferably begins with the separation of cell debris from the expressed PCV-2 ORF2 antigen via a separation step. Preferred separation steps include filtration, centrifugation at speeds up to about 20,000×g, continuous flow centrifugation, chromatographic separation using ion exchange or gel filtration, and conventional immunoaffinity methods. Those methods are known to persons skilled in the art for example by (E. L. V. Harris and S. Angel (eds.), Protein purification methods—a practical approach, IRL Press Oxford 1995). The most preferred separation methods include centrifugation at speeds up to about 20,000×g and filtration. Preferred filtration methods include dead-end microfiltration and tangential flow (or cross flow) filtration including hollow fiber filtration dead-end micro filtration. Of these, dead-end microfiltration is preferred. Preferred pore sizes for dead-end microfiltration are between about 0.30-1.35 µm, more preferably between about 0.35-1.25 µm, still more preferably between about 0.40-1.1 µm, and most preferably between about 0.45-1.0 µm. It is believed that any conventional filtration membrane will work for purposes of the present invention and polyethersulfone membranes are preferred. Any low weight nucleic acid species are removed during the filtration step.

Further purification of PCV-2 antigen, preferably of the PCV-2 ORF2 antigen can be achieved with chromatography procedures, preferably a two-step chromatography procedure. However it is also possible to start with the chromatography procedure in the event, the loading material does not comprise cell debris.

If the PCV-2 antigen is assembled to virus like particles (VLP), the first step is preferably a size exclusion (gel filtration) chromatography, which can be done, for instance, by using a Sephacryl S300 matrix. In lab scale use of HiPrep 26/60 Sephacryl S300HR columns are most preferred. However, any other size exclusion chromatography matrices known to a person skilled in the art can be used, which allow the separation of the PCV-2 ORF2 VLPs from the culture filtrate or supernatant. Suitable matrices are described, for instance, in E. L. V. Harris and S. Angel (eds.), Protein purification methods—a practical approach, IRL Press Oxford 1995). The gel filtration chromatography can be conducted, for instance, by loading the column with the crude preparation comprising the PCV-2 antigen with a flow-rate of 1.0 ml/min and eluting the column with 1.5 column volume of a buffer comprising 20 mM Tris, pH 6.5, 5 mM DTT. However, the PCV-2 ORF2 antigen can also be purified by using affinity chromatography, for instance, via selective binding to an immobilized PCV-2 ORF2 specific antibody, or any other method known to a person skilled in the art.

Thus according to a preferred embodiment, the immunogenic composition comprising a purified PCV-2 antigen, preferably a purified PCV-2 ORF2 antigen, and the adjuvant, is obtainable by a process comprising the steps
  a) Expressing the PCV-2 antigen, prefer the PCV-2 ORF2 antigen in a host cell;
  b) Harvesting the cell culture obtaining PCV-2 antigen, preferably the PCV-2 ORF2 antigen;
  c) Purifying the harvest comprising the PCV-2 antigen, preferably the PCV-2 ORF2 antigen by size exclusion chromatography (gel filtration);
  d) Admixing the purified PCV-2 antigen, preferably the PCV-2 ORF2 antigen with an adjuvant.

According to a preferred embodiment, the size exclusion chromatography is performed as described herein, preferably as described in Example 3. Preferably, the size exclusion results in an immunogenic composition having purity grade of more than 80% (w/w), preferably more than 90% (w/w) with reference to the total amount of protein included in the immunogenic composition prior to the mixture with the adjuvant. The purity grade can be estimated by Imperial Protein Stain (Pierce) staining after SDS PAGE via NuPAGE 10% Bis-Tris gels (Invitrogen) using the NuPAGE MOPS buffer system (Invitrogen).

In order to obtain a higher purity grade a second chromatography step can be done, which however is different from the first one. For instance if the first purification step/chromatography step is size exclusion (gel filtration) the second should different from that e.g. an affinity chromatography, ion exchange chromatography, etc.

Preferably, if the first step to purify PCV-2 antigen, preferably to purify PCV-2 ORF2 antigen is a size exclusion (gel filtration) chromatography, the second step can be ion-exchange chromatography, preferably anion-exchange chromatography (AIEX). A preferred anion-exchange chromatography matrix for the purification of PCV-2 antigen, preferably the PCV-2 ORF2 antigen is Q Sepharose. In a small scale of about 50 ml, use of 5 ml HiTrap Q Sepharose HP columns are most preferred. The anion exchange chromatography can be conducted, for instance, as described in Example 3. Briefly, about 50 ml of the void volume fraction pool from the size exclusion chromatography step can be loaded onto the AIEX column at a flow rate of 3.0 ml/min. Following a washing step using, for instance, 20 mM Tris, pH 6.5, 5 mM DTT to remove unbound material, protein can be eluted with a single step of 8 column volumes of the following buffer (20 mM Tris, pH 6.5, 5 mM DTT, 1.0 M NaCl) The flow-through from the AIEX run can be loaded back onto the Q Sepharose column and eluted as described above to increase the yield. This two step technique (size exclusion followed by anion-exchange chromatography) effectively separates PCV-2 ORF2 antigen from most of the other protein components of the culture harvest.

Thus according to a preferred embodiment, the immunogenic composition comprising a purified PCV-2 antigen, preferably the PCV-2 ORF2 antigen, and the adjuvant, is obtainable by a process comprising the steps
  a) Expressing the PCV-2 antigen, prefer the PCV-2 ORF2 antigen in a host cell;
  b) Harvesting the cell culture obtaining PCV-2 antigen, preferably the PCV-2 ORF2 antigen;
  c) Purifying the harvest comprising the PCV-2 antigen, preferably the PCV-2 ORF2 antigen by size exclusion chromatography (gel filtration) followed by anion exchange chromatography; and
  d) Admixing the purified PCV-2 antigen, preferably the PCV-2 ORF2 antigen with an adjuvant.

According to a preferred embodiment, the size exclusion chromatography and the anion exchange chromatography are performed as described herein, preferably as described in Example 3. Preferably, the two step purification strategy results in an immunogenic composition having purity grade of more than 90% (w/w), preferably more than 95% (w/w) with reference to the total amount of protein included in the immunogenic composition prior to the mixture with the adjuvant. The purity grade can be estimated by Imperial Protein Stain (Pierce) staining after SDS PAGE via NuPAGE 10% Bis-Tris gels (Invitrogen) using the NuPAGE MOPS buffer system (Invitrogen).

As described above, the recovery process of the PCV-2 antigen, preferably the PCV" ORF2 antigen begins with the separation of cell debris from the expressed PCV-2 ORF2 antigen via a separation step. A preferred separation step includes a micro filtration through a filter having a pore size of about 0.6 µm to about 2 µm, preferably having a pore size of about 0.8 mm to about 1.2 µm.

Thus the immunogenic composition comprising a purified PCV-2 antigen, preferably the PCV-2 ORF2 antigen, and the adjuvant, is obtainable by a process comprising the steps
  a) Expressing the PCV-2 antigen, prefer the PCV-2 ORF2 antigen in a host cell;
  b) Harvesting the cell culture obtaining PCV-2 antigen, preferably the PCV-2 ORF2 antigen;
  c) Filtering the harvest obtained under step b) through a filter having a pore size of 0.6 to 2.0 µm.
  d) Purifying the filtrate comprising the PCV-2 antigen, preferably the PCV-2 ORF2 antigen and obtained under step c) by size exclusion chromatography (gel filtration) optionally followed by anion exchange chromatography; and
  e) Admixing the purified PCV-2 antigen, prefer the PCV-2 ORF2 antigen with an adjuvant.

According to a preferred embodiment, the micro-filtration, size exclusion chromatography and the anion exchange chromatography are performed as described herein, preferably as described in Example 3. Preferably, the two step purification strategy including the pre-filtration step results in an immunogenic composition having purity grade of more than 90% (w/w), preferably more than 95% (w/w) with reference to the total amount of protein included in the immunogenic composition prior to the mixture with the adjuvant. The purity grade can be estimated by Imperial Protein Stain (Pierce) staining after SDS PAGE via NuPAGE 10% Bis-Tris gels (Invitrogen) using the NuPAGE MOPS buffer system (Invitrogen).

The immunogenic compositions comprising the purified PCV-2 antigen, preferably the purified PCV-2 ORF2 antigen described herein, preferably those obtainable by the methods described herein are characterized by an increased immunogenicity as compared to an immunogenic composition not comprising such a purified PCV-2 antigen or purified PCV-2 ORF2 antigen.

In the event, viral vectors such as a recombinant poxvirus, adenovirus or baculovirus is used to produce the PCV-2 antigen, preferably the PCV-2 ORF2 antigen, it is recommended to inactivate the viral nucleic acid by an appropriate inactivation treatment. Such inactivation may occur anytime during the purification of the PCV-2 antigen, preferably the PCV-2 ORF2 antigen. Thus, inactivation may occur immediately after the harvest of the cell culture fluid comprising the PCV-2 antigen, preferably the PCV-2 ORF2 antigen, or after the micro-filtration of the of PCV-2 antigen, preferably of the PCV-2 ORF2 antigen, if micro-filtration is done, prior or after the purification step, for instance, prior to or after the gel filtration, and prior to or after the anion exchange chromatography, if this is done.

Any conventional inactivation method can be used for purposes of the present invention. Thus, inactivation can be performed by chemical and/or physical treatments. In preferred forms, the volume of harvest fluids is determined and the temperature is brought to between about 32° C.-42° C., more preferably between about 34° C.-40° C., and most preferably between about 35° C.-39° C. Preferred inactivation methods include the addition cyclized binary ethylenimine (BEI), preferably in a concentration of about 1 to about 20 mM, preferably of about 2 to about 10 mM, still more preferably of about 2 to about 8 mM, still more preferably of about 3 to about 7 mM, most preferably of about 5 mM. For example the inactivation includes the addition of a solution of 2-bromoethyleneamine hydrobromide (BEA), preferably of about 0.4M, which has been cyclized to 0.2M binary ethylenimine (BEI) in 0.3N NaOH, to the fluids to give a final concentration of about 5 mM BEI. Preferably, the fluids are then stirred continuously for 2-96 hours and the inactivated harvest fluids can be stored frozen at −40° C. or below or between about 1° C.-7° C. After inactivation is completed a sodium thiosulfate solution, preferably at 1.0M is added to neutralize any residual BEI. Preferably, the sodium thiosulfate is added in equivalent amount as compared to the BEI added prior to for inactivation. For example, in the event BEI is added to a final concentration of 5 mM, a 1.0M sodium thiosulfate solution is added to give a final minimum concentration of 5 mM to neutralize any residual BEI.

Prior to the mixing of the purified PCV-2 antigen, preferably of the PCV-2 ORF2 antigen with an adjuvant, it is also recommended to dialyze the purified PCV-2 antigen, preferably the PCV-2 ORF2 antigen against phosphate buffered saline, pH 7.4 or any other physiological buffer.

The methods described above result in an PCV-2 antigen with reduced virucidal activity as defined herein as well as in an improved immunogenicity, if the PCV-2 antigen has a purity grade of more than 50% (w/w), preferably of more than 70% (w/w), even more preferred of more than 80% (w/w), even more preferred of more than 85% (w/w), even more preferred of more than 90% (w/w), most preferred of more than 95% (w/w) with reference to the total amount of protein included in the immunogenic composition prior to the mixture with any adjuvant. However, the purified PCV-2 antigen obtainable according to this method II can also be mixed and used together with an adjuvant, preferably with any of the adjuvants described herein. The preferred adjuvant is a Carbopol, preferably in a concentration of about 0.1 to 10 mg/ml, more preferred in a concentration of 0.5 to 5 mg/ml, most preferably of about 1 mg/ml of the final immunogenic composition.

Again, the present invention does not only provides any of the methods described herein, including the alternative method II, it also provides a PCV-2 antigen, preferably a purified PCV-2 antigen, most preferably a purified PCV-2 ORF-2 protein obtainable by any of the methods described herein, including the alternative method II. Moreover, the present invention also provides PCV-2 antigenic compositions comprising a PCV-2 antigen, preferably a purified PCV-2 antigen, most preferably a purified PCV-2 ORF-2 protein obtainable by any of the methods described herein, including the alternative method II. The amount of the PCV-2 antigen, in particular of the purified PCV-2 ORF2 antigen in the final immunogenic composition should be in a range from about 0.25 to about 400 µg per dose with reference to the final immunogenic composition. Preferably the finally immunogenic composition should include an amount of PCV-2 antigen, preferably of PCV-2 ORF2 antigen in a range from about 2 to about 200 µg/dose, even more preferably from about 3 to about 150 µg/dose, still more preferably from about 4 to about 100 µg/dose, still more preferably from about 5 to about 80 µg/dose, still more preferably from about 6 to about 60 µg/dose, even more preferably from about 7 to about 50 µg/dose, even more preferably from about 8 to about 40 µg/dose, still more preferably from about 8 to about 32 µg/dose, even more preferably from about 8 to about 24 µg/dose, and most preferred from about 8 to about 16 µg/dose.

The immunogenic compositions provided herewith, including those obtainable by the method II comprises one or more additional antigens of another disease-causing organism. Those "another disease-causing organisms" are defined above. Preferably the additional antigen is Porcine Reproductive and Respiratory Syndrome Virus. Even more preferably, the Porcine Reproductive and Respiratory Syndrome Virus antigen comprises a live virus, and still more preferably a modified live virus. Still more preferably, the modified live Porcine Reproductive and Respiratory Syndrome Virus antigen comprises a modified live virus strain of ATCC Accession Number VR 2332, and still more preferably comprises INGELVAC® PRRS MLV. In a further aspect of the present application, the additional antigen is *Mycoplasma hyopneumoniae*. Preferably the *Mycoplasma hyopneumoniae* antigen is a bacterin, and more preferably, the *Mycoplasma hyopneumoniae* bacterin is INGELVAC® MYCOFLEX. Most preferred are combinations with, both antigen of Porcine Reproductive and Respiratory Syndrome Virus and *Mycoplasma hyopneumoniae*.

Due to the increased immunogenicity of the immunogenic composition including the purified PCV-2 antigen, preferably the purified PCV-2 ORF2 antigen provided herewith, the immunogenic compositions can be used for reducing the incidence or reducing the severity of clinical signs caused by or being associated with PCV-2 infections as compared to an animal not receiving that immunogenic composition.

The term "reduction in the incidence of or severity of clinical signs" shall mean that any of such signs are reduced in incidence or severity in animals receiving an administration of the vaccine in comparison with a "control group" of animals when both have been infected with or challenged by the pathogen from which the immunological active component(s) in the vaccine are derived and wherein the control group has not received an administration of the vaccine or immunogenic composition. In this context, the term "decrease" or "reduction" means a reduction of at least 10%, preferably 25%, even more preferably 50%, most preferably of more than 100% in the vaccinated group as compared to the control group not vaccinated.

As used herein, "clinical symptoms" or "clinical signs" shall refer to signs of infection from a pathogen that are directly observable from a live animal such as symptoms. Representative examples will depend on the pathogen selected but can include things such as nasal discharge, lethargy, coughing, elevated fever, weight gain or loss, dehydration, diarrhea, swelling, lameness, and the like. PCV-2 clinical signs can include wasting, paleness of the skin, unthriftiness, respiratory distress, diarrhea, icterus, and jaundice.

Reducing in the incidence of or the severity of clinical signs caused by or being associated with PCV-2 infections in an animal can be reached by the administration of only a single dose of such immunogenic composition to an animal in need of such treatment. However, the immunogenic composition provided herewith can also be administered in two doses or more doses, with an interval of 2 to 4 weeks between the administration of the first dose and the any subsequent dose. Thus, according to a further embodiment the immunogenic composition provided herewith including the purified PCV-2 antigen, preferably the purified PCV-2 ORF2 antigen can be administered in one, two or more doses to an animal in need thereof.

In particular, in a further aspect of the present application, an immunogenic composition comprising a PCV-2 antigenic composition as described above is provided wherein the immunogenic composition, when administered to an animal, reduces lymphoid depletion and inflammation by at least 80% in an animal as compared to an animal not receiving the immunogenic composition. Thus, in a further aspect of the present application, an immunogenic composition is provided comprising a PCV-2 antigenic composition as described above and the immunogenic composition reduces lymphoid depletion and inflammation by at least 80% in an animal that has received an administration of the immunogenic composition as compared to an animal not receiving the immunogenic composition.

In a further aspect of the present application, an immunogenic composition comprising a PCV-2 antigenic composition as described above is provided, wherein the immunogenic composition, when administered to an animal, reduces lung lesions by at least 80% in an animal as compared to an animal not receiving the immunogenic composition. Thus, in a further aspect of the present application, an immunogenic composition comprising a PCV-2 antigenic composition is provided as described above and the immunogenic composition reduces lung lesions by at least 80% in an animal that has received an administration of the immunogenic composition as compared to an animal not receiving the immunogenic composition.

In a further aspect of the present invention, an immunogenic composition comprising a PCV-2 antigenic composition, as described above, is provided wherein the immunogenic composition induces a protective immune response against PCV-2 after the administration of one dose of the immunogenic composition. The immunogenic composition comprising a PCV-2 antigenic composition can be of any volume including 1 ml, 2 ml, 3 ml, 4 ml, 5 ml and higher. In preferred forms, 2 ml of the immunogenic composition comprises one dose of the PCV-2 antigen. Thus, in a further aspect of the present invention, an immunogenic composition as described above is provided wherein the immunogenic composition comprising a PCV-2 antigenic composition induces a protective immune response against PCV-2 after the administration of one dose of the immunogenic composition. In a further aspect, 2 ml of the immunogenic composition comprises one dose of the PCV-2 antigen.

As used herein, a "protective immune response" refers to a reduced incidence of or reduced severity of clinical, pathological, or histopathological signs or symptoms of infection from a pathogen of interest up to and including the complete prevention of such signs or symptoms.

The term "Pathological" signs shall refer to signs of infection that are observable at the microscopic or molecular level, through biochemical testing, or with the naked eye upon necropsy. For PCV-2, pathological signs will include microscopic and macroscopic lesions on multiple tissues and organs, with lymphoid organs being the most common site for lesions.

The term "Histopathological" signs shall refer to signs of tissue changes resulting from infection.

The terms, "clinical symptoms" or "clinical signs" are defined above.

In a further aspect of the present invention, an immunogenic composition comprising a PCV-2 antigenic composition and a PRRRS antigen, preferably any one of the PRRS antigens described herein, as described above, is provided wherein the immunogenic composition induces a protective immune response against PRRS virus after the administration of one dose of the immunogenic composition. Again, any dosage volume can be produced, but in preferred forms, 2 ml of the immunogenic composition comprises one dose of the PRRS antigen and one dose of the PCV-2 antigen. Thus, in a further aspect of the present invention, an immunogenic composition as described above comprising a PRRSV and a PCV-2 antigenic composition as described herein, is provided wherein the immunogenic composition induces a protective immune response against PRRS after the administration of one dose of the immunogenic composition. In a further aspect, 2 ml of the immunogenic composition comprises one dose of the PRRS antigen and one dose of the PCV-2 antigen.

In a further aspect of the present invention, an immunogenic composition comprising a PCV-2 antigenic composition as described herein and *Mycoplasma hyopneumoniae* antigen as described above, is provided wherein the immunogenic composition induces a protective immune response against *Mycoplasma hyopneumoniae* after the administration of one dose of the immunogenic composition. Again, any dosage volume can be produced, but in preferred forms, 2 ml of the immunogenic composition comprises one dose of the *Mycoplasma hyopneumoniae* antigen and one dose of a PCV-2 antigen. Thus, in a further aspect of the present invention, an immunogenic composition as described above is provided wherein the immunogenic composition induces a protective immune response against *Mycoplasma hyopneumoniae* after the administration of one dose of the immunogenic composition comprising a PCV-2 antigenic composition as described herein and *Mycoplasma hyopneumoniae* antigen. In a further aspect, 2 ml of the immunogenic composition comprises one dose of the *Mycoplasma hyopneumoniae* antigen.

In a further aspect of the present application, an immunogenic composition, as described above, is prepared for the administration of 2 ml per dose.

In a further aspect of the present application, a method of reducing one or more clinical symptoms of a PCV-2 infection in an animal as compared to an animal not receiving the immunogenic composition is provided. In general, the method comprises the step of administering to an animal any of the immunogenic compositions comprising a PCV-2 antigenic or composition as described above. Preferably, one or more clinical symptoms of a PCV-2 infection are reduced after the administration of a single dose of the or immunogenic composition. Thus, according to a further aspect of the present application, a method of reducing one or more clinical symptoms of a PCV-2 infection in an animal as compared to an animal not receiving the immunogenic composition comprising a PCV-2 antigenic composition as described herein is provided. In general, the method comprises the step of administering to an animal any of the immunogenic compositions comprising a PCV-2 antigenic composition described above, wherein one or more clinical symptoms of a PCV-2 infection are reduced, preferably after the administration of a single dose of the immunogenic composition comprising a PCV-2 antigenic composition as described herein.

In a further aspect of the present application, a method of reducing one or more clinical symptoms of a PRRS infection in an animal as compared to an animal not receiving the immunogenic composition is provided. In general, the method comprises the step of administering to an animal any of the immunogenic compositions described above comprising a PCV-2 antigenic composition as described herein and a PRRS Virus as described herein. Preferably, one or more clinical symptoms of a PRRS infection are reduced after the administration of a single dose of the immunogenic composition comprising a PCV-2 antigenic composition as described herein and a PRRS Virus as described herein. Thus, according to a further aspect of the present application, a method of reducing one or more clinical symptoms of a PRRS infection in an animal as compared to an animal not receiving the immunogenic composition comprising a PCV-2 antigenic composition as described herein and a PRRS Virus as described herein, is provided. Clinical signs of Porcine Reproductive and Respiratory Syndrome Virus (PRRSV) include, but are not limited to inappetance, fever, abortion, transient discoloration, prolonged anoestrus, coughing, respiratory signs, mastitis, agalactia, lethargy, mummified piglets, stillbirths, weak piglets at birth, reduction in farrowing rate, early farrowing, diarrhea, wasting, sneezing, eye discharge, pale skin, mortality, and combinations thereof.

In a further aspect of the present application, a method of reducing one or more clinical symptoms of a *Mycoplasma hyopneumoniae* infection in an animal as compared to an animal not receiving the immunogenic composition comprises a PCV-2 antigenic composition as described herein and a *Mycoplasma hyopneumoniae* antigen as described herein, is provided. In general, the method comprises the step of administering to an animal any of the immunogenic compositions described above. Preferably, one or more clinical symptoms of a *Mycoplasma hyopneumoniae* infection are reduced after the administration of a single dose of the immunogenic composition comprising a PCV-2 antigenic composition as described herein and a *Mycoplasma hyopneumoniae* antigen as described herein. Thus, according to a further aspect of the present application, a method of reducing one or more clinical symptoms of a *Mycoplasma hyopneumoniae* infection in an animal as compared to an animal not receiving the immunogenic composition comprising a PCV-2 antigenic composition as described herein and a *Mycoplasma hyopneumoniae* antigen as described herein is provided. Clinical signs of *Mycoplasma hyopneumoniae* (*M. hyo*) infection include, but are not limited to a dry cough, impaired performance, and lung lesions.

The immunogenic composition comprising the purified PCV-2 antigen, preferably the PCV-2 ORF2 antigen as provided herein, has improved immunogenicity. Therefore, the immunogenic composition provided herewith is suitable to improve the immune response in an animal receiving such immunogenic composition. Thus, according to a further embodiment, the present invention provides a method for improving the immune response in an animal against PCV-2 comprising the step: adminstistering a the immunogenic composition as described herein and having a purified PCV-2 antigen, preferably a purified PCV-2 ORF-2 protein as provided herewith, to an animal in need thereof. According to a preferred aspect, the PCV-2 antigen, preferably the PCV-2 ORF2 antigen used in such method is purified to an extent of more than 60% (w/w), preferably more than 60% (w/w), even more preferred to more than 70% (w/w), even more preferred to more than 80% (w/w), even more preferred to more than 90% (w/w), most preferred to more than 95% (w/w) with reference to the total amount of protein included in the immunogenic composition. The purity grade can be estimated by Imperial Protein Stain (Pierce) staining after SDS PAGE via NuPAGE 10% Bis-Tris gels (Invitrogen) using the NuPAGE MOPS buffer system (Invitrogen). The PCV-2, and preferably the PCV-2 ORF2 can be purified using conventional methods well known to a person skilled in the art.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the results of ultrafiltration configuration pilot scale using a 10% Bis-Tris/MOPS gel that demonstrates the presence of the ORF 2 after the filtration process. Lanes were loaded as follows: (1) marker; (2) n/a; (3) n/a; (4) 24—180/181 Pre conc—20 µl; (5) 25—180/181 1× antigens—20 µl; (6) 26—180/181 filter wash—20 µl; (7) 27—PCV 504 Preconc—8 µl; (8) 28—PCV 504 Perm—20 µl; (9) 29—PCV 504 1×—20 µl; (10) 092704PD—20 µl; (11) marker.

DETAILED DESCRIPTION

The following examples set forth preferred materials and procedures in accordance with the present invention. It is to be understood, however, that these examples are provided by way of illustration only, and nothing therein should be deemed a limitation upon the overall scope of the invention.

EXAMPLE 1

This example describes a laboratory scale and pilot scale process for manufacturing concentrated PCV-2 ORF2 antigen that will have a reduced virucidal activity in comparison to manufacturing processes that do not include the steps of the present invention. Specifically, the effects that the present invention has on the virucidal activity of the PCV-2 ORF2 antigen on PRRS virus will be determined.
Materials and Methods
Production Antigen:
Laboratory Scale:
 PCV SUB037H1-F, 18.94 kg
 PCV 1025, 20.6 kg
 PCV 180/181, 20.0 kg
 PCV SUB 504PD, 40 kg
Pilot Scale:
 PCV SUB 506PD, 362 kg
 PCV SUB 507PD, 384 kg
 PCV SUB512PD, 430 kg
 PCV SUB 513PD, 405 kg
Ultra Filtration Cartridges: GE Healthcare, Steam-In-Place (SIP), hollow fiber membrane cartridges
UFP-100-E-55-STM: 100,000 NMWC, 1 mm diameter tubule; used in UF-002 in X109, laboratory scale.
UFP-300-E-55-STM: 300,000 NMWC, 1 mm diameter tubule; used in UF-002 in X109, laboratory scale.
UFP-100-E-65-MSM: 100,000 NMWC, 1 mm diameter tubule; used in UF-B2614, in APU-1, pilot scale.
UFP-300-E55-SMO: 300,000 NMWC, 1 mm diameter tubule; used in UF-2713 in VP-1, pilot scale.
The following Ultrafiltration equipment was used in the feasibility evaluation and initial process development:

TABLE 1

| Equipment | | | |
|---|---|---|---|
| Process Step | Procedure | Equipment | Identification |
| Ultrafiltration | Antigen Concentration | Flex-Stand Concentrator | UF-002 in X109, laboratory scale |
| | | UF Skid | UF-B2614 in APU-1, pilot scale |
| | | UF Skid | UF-2713 in VP-1, pilot scale |

Manufacturing Process:
Ultrafiltration (UF) Configuration: Laboratory Scale 50 liter carboys containing filtered, inactivated, neutralized, PCV-2 ORF2 material generated in building P were used in the concentration process with the GE Healthcare (Amersham) Flex Stand 30 L size UF skid #002.

The initial concentration processes used a "batch" diafiltration scheme, whereby approximately 20 kg of antigen material was transferred to the UF skid and concentrated through a 100,000 NMWC hollow fiber cartridge (UFP-100-E-55-STM). The 100,000 NMWC concentration processes used PCV-2 ORF2 lots SUB037PD and PCV1025 material from PD and Manufacturing, respectively.

These two initial runs were concentrated to approximately 4× of the original volume and were Q.S.'d (quantity substantiated) in the feed tank back to the original transfer volume. The concentrated material was treated in this manner for a total of 2 concentrations per lot number, with the third and final concentration harvested as a concentrate and a portion Q.S.'d to 1× of the original volume. Samples were drawn pre-concentration, at each concentration step and at each Q.S. step. Permeate samples were drawn during each concentration step.

The next two consecutive runs concentrated the PCV-2 ORF2 antigen without a saline wash. The concentrated material was sampled at approximately 4× and then at final concentration. Approximately 20 kg of antigen material was transferred to the UF skid holding tank and concentrated through a 300,000 NMWC hollow fiber cartridge (UFP-300-E-55-STM). A second 20 L volume was added to the holding tank with the concentrate from the first 20 L. This was concentrated to final volume. The 300,000 NMWC concentration processes used PCV-2 ORF2 lots PCV 180/181 pool and SUB504PD generated by Manufacturing and PD, respectively. Samples were drawn pre-concentration and at each concentration step. Permeate samples were drawn during each concentration step.

Ultrafiltration Configuration: Pilot Scale

Pilot scale processes utilized SUB lots 506PD, 512PD and 513PD. Antigen pre-concentration volumes ranged from approximately 350 L to 430 L. Lots SUB506PD and SUB513PD were transferred to DSP (down-stream processing) 2602 and concentrated with UF-B2614 in APU-1 using a 100,000 NMWC filter (UFP-100-65-E-MSM), with 4.2 m$^2$ surface area. SUB512PD was transferred to DSP 2701 and concentrated with UF-2713 using a 300,000 NMWC filter (UFP-300-E-SMO) with 2.1 m$^2$ surface area. Final concentrated material was harvested for each lot and stored at 4° C. for analysis.
Results and Conclusions
Ultrafiltration (UF) Configuration: Laboratory Scale Filtration with 100,000 NMWC (100 kDa) versus 300,000 NMWC (300 kDa) filters was comparable in concentration times and was feasible when considering a full scale process. Filtration times for the 100 kDa filter, concentrating 4×, with approximately 18 L to 26 L, ranged from 14 minutes to 32 minutes, with the shorter times resulting from the saline wash steps (Table 2). Filtration times for the 300 kDa filter, concentrating 3.2×, 7× for PCV180/181 and 21.5× for SUB504PD with approximately 40 L of material concentrated in two consecutive 20 L volumes yielded 3.2× at 25 minutes, 7× at 23 minutes and 21.5× at 32 minutes. Some time variation is expected due to the time taken to get a concentration process to a target trans-membrane pressure (TMP) of 10.25 psi.

Process flux values ranged from 27.43 lmh to 32.00 lmh for the PCV180/181 lot, with the 32.00 lmh value resulting from a spike toward the end of the concentration process. Flux values for SUB 504PD material were 28.57 lmh during the first-20 L concentration and 35.71 lmh during the $2^{nd}$-20 L concentration. (Tables 3 and 4)

TABLE 2

Process Data

| Lot # | Starting Concentration Volume | X Conc. | Time to Concentrate (min) |
|---|---|---|---|
| PCV 037 QS-0 (100 kDa) | 18.94 | 4.17 | 24 |
| PCV 037 QS-1 (100 kDa) | 18.76 | 4.75 | 16 |
| PCV 037 QS-2 (100 kDa) | 19.05 | 4.70 | 14 |
| PCV 1025 QS-0 (100 kDa) | 20.59 | 4.39 | 28 |
| PCV 1025 QS-1 (100 kDa) | 20.24 | 4.65 | 29 |
| PCV 1025 QS-2 (100 kDa) | 18.71 | 3.6 | 17 |
| PCV 180/181 conc-1 (300 kDa) | 20 | 3.50 | 25 |
| PCV 180/181 conc-2 (300 kDa) | 26.01 | 7.00 | 23 |
| SUB 504PD conc-2 (300 kDa) | 24.72 | 21.50 | 32 |

TABLE 3

Process Data

PCV 180/181: 300,000 NMWC Filter

| | TIME | TMP | PERM FLOW (ml/min) | FLUX (lmh) |
|---|---|---|---|---|
| Conc-1 | 9:55 | 9 | N/A | N/A |
| Conc-2 | 10:23 | 12.5 | N/A | N/A |
| Conc-2 | 10:30 | 12.5 | 960 | 27.43 |
| Conc-2 | 10:33 | 14.5 | 960 | 27.43 |
| Conc-2 | 10:36 | 10.5 | 1120 | 32.00 |
| Conc-2 | 10:39 | 11 | 810 | 23.14 |

TABLE 4

Process Data

SUB504PD: 300,000 NMWC Filter

| | TIME | TMP | PERM FLOW (ml/min) | FLUX (lmh) |
|---|---|---|---|---|
| Conc-1 | 15:29 | 9.5 | 1000 | 28.57 |
| Conc-2 | 16:00 | 10.25 | 1250 | 35.71 |

Change in potency post filtration was found unchanged when the concentrated material was Q.S.'d back to 1× volume, as with SUB 037 reconstituted material and PCV 1025 reconstituted material. Concentrate antigen content values pushed the limits of the assay beyond the validated approximate 64 µg limit, as is seen in the values in tables 5 through 8 where antigen content amounts are compared to the expected calculated amounts. Permeate values from the concentrations performed using SUB 037, PCV 180/181 and SUB 504PD antigens showed no significant loss of material due to filtration. All permeate antigen content amounts fell into the undetectable range of the assay. PCV 1025 antigen permeate antigen content amounts were not collected.

TABLE 5

SUB 037 Change in PCV-2 Antigen Content (in µg)

| Lot Number/vol | PreConc. Antigen Content | PostConc. Antigen Content | Concentration Factor | Calc Antigen Content | Change from Calculated Antigen Content | Gain/Loss from Calc RP |
|---|---|---|---|---|---|---|
| SUB 037 (18.94 kg)--4.7×-100 kDa--PDX | 56 | 137.6 | 4.7 | 263.2 | −125.6 | loss |
| Concentrated and Reconstituted with Saline: QS-1 | 56 | 61.6 | 1 | 56 | 5.6 | gain |
| Concentrated and Reconstituted with Saline: QS-2 | 56 | 62.7 | 1 | 56 | 6.7 | gain |
| Concentrated and Reconstituted with Saline: QS-3 | 56 | 55.8 | 1 | 56 | −0.2 | loss |
| SUB 037 permeates 1, 2, 3 | — | 0 | | | | No loss |

TABLE 6

PCV 1025 Change in PCV-2 Antigen Content (in µg)

| Lot Number/vol | PreConc. Antigen Content | PostConc. Antigen Content | Concentration Factor | Calc Antigen Content | Change from Calculated Antigen Content | Gain/Loss from Calc RP |
|---|---|---|---|---|---|---|
| 1025 (20.46 kg)-- 4.5X--100 kDa--PDX | 70.88 | 288.64 | 4.5 | 318.96 | −30.32 | loss |
| Concentrated and Reconstituted with Saline-1 | N/A(NO SAMPLE) | N/A | 1 | N/A | N/A | no sample |
| Concentrated and Reconstituted with Saline-2 | 70.88 | 66.24 | 1 | 70.88 | −4.64 | loss |
| Concentrated and Reconstituted with Saline-3 | 70.88 | 76.00 | 1 | 70.88 | 5.12 | gain |
| 1025 permeate | — | N/A | | | N/A | |

TABLE 7

Change in PCV-2 Antigen Content (in µg)

| Lot Number/vol | PreConc. Antigen Content | PostConc. Antigen Content | Concentration Factor | Calc Antigen Content | Change from Calculated Antigen Content | Gain/Loss from Calc RP |
|---|---|---|---|---|---|---|
| 180/181 (40.3 kg)-- 3.5X--300 kDa--PDX | 43.36 | 90.8 | 3.5 | 151.76 | −60.96 | loss |
| 180/181 7.2X | 43.36 | 247.04 | 7.2 | 312.19 | −65.15 | loss |
| 180/181 permeate | — | 0 | | | No loss | N/A |

TABLE 8

Change in PCV-2 Antigen Content (in µg)

| Lot Number/vol | PreConc. Antigen Content | PostConc. Antigen Content | Concentration Factor | Calc Antigen Content | Change from Calculated Antigen Content | Gain/Loss from Calc RP |
|---|---|---|---|---|---|---|
| SUB504 (40.43 kg) 4.3X-300 kDa--PDX | 22.24 | 68.16 | 4.3 | 95.63 | −27.47 | loss |
| SUB504 20X | 22.24 | 448.48 | 20 | 444.8 | 3.68 | gain |
| SUB504 permeate | — | 0 | | | No loss | |

SDS-PAGE gels were run with material from PCV 180/181 and SUB 504PD in R&D. The ORF2 band residing at approximately 27 kDa in FIG. 1 was consistent with the banding pattern of the reference in lane 10. This band size has previously been determined to be ORF2. The permeate material from SUB 504PD, 300 kDa filtration concentration, exhibited an absence of banding at the 27 kDa site. No ORF2 protein was apparently lost with this pore size filter. The gel was run under reducing conditions.

Virucidal activity of the pre-concentrate antigen, concentrated antigen, reconstituted antigen and filtration permeate was tested against the PRRS virus vaccine. Initial results from Quality Control (QC) for SUB 037 were unsatisfactory for the pre-concentrated and concentrated (100 kDa filter) material, which had been reconstituted back to 1× with saline. However, when the concentrated material was formulated into vaccines, concentrations up to 80% inclusion in the vaccine reduced this virucidal activity to a satisfactory level well below the acceptance limit of 0.7 log/ml loss of PRRS virus titer. Permeate material from SUB 037 showed borderline passing to unsatisfactory levels of virucidal activity. See Table 9.

PCV 1025 pre-concentrated material was found unsatisfactory for virucidal activity to PRRS with loss in PRRS titer at 1.5 log/ml loss. The three saline reconstituted concentrate (100 kDa filter) materials were passing at 0.5 log/ml loss and 0.6 log/ml loss with one of the reconstituted concentrates satisfactory with "no change" in PRRS titer. Permeate samples were not tested for this lot. See Table 10.

PCV 180/181 pre-concentrated vaccine material was unsatisfactory for virucidal activity to PRRS for 2 of the 3 vaccines prepared. Percent antigen inclusion levels ranged from 37.0% to 55.5%. The highest % inclusion pre-concentrate vaccine was found satisfactory.

Vaccines prepared from 1× (concentrate reconstituted to 1× with saline) material were found satisfactory for virucidal activity to PRRS virus. Percent antigen inclusion levels ranged from 44% to 66%. See Table 11.

SUB 504PD vaccines prepared from pre-concentrated antigen with 79.5% vaccine inclusion were satisfactory for virucidal activity to PRRS virus. Vaccines prepared from 4.3× concentrated antigen with 23.5-35% vaccine inclusion and from 21.5× concentrated antigen with 3.5-5.5% vaccine inclusion were also satisfactory. Last, the filter wash antigen prepared with 72% inclusion level was found satisfactory for virucidal activity to PRRS virus.

TABLE 9

SUB 037 Virucidal Activity

| Sample ID | Change in Potency log/ml | Sat/ Unsat |
| --- | --- | --- |
| SUB 037 PreConc (18.94 kg)--4.7x--100 kDa--PDX Anitgen Content 56 pre/137.6 post | 1.4 | unsat |
| Concentrated and Reconstituted with Saline-1 | 0.8 | unsat |
| Concentrated and Reconstituted with Saline-2 | 1.3 | unsat |
| Concentrated and Reconstituted with Saline-3 | 1.3 | unsat |
| SUB 037 permeate-1 | 0.6 | sat |
| SUB 037 permeate-2 | 1.0 | unsat |
| SUB 037 permeate-3 | 0.5 | sat |
| Vaccine: 20% inclusion Ames** | −0.2 | sat |
| Vaccine: 40% inclusion Ames** | −0.2 | sat |
| Vaccine: 60% inclusion Ames** | 0.2 | sat |
| Vaccine: 80% inclusion Ames** | 0.1 | sat |

TABLE 10

PCV 1025 Virucidal Activity

| Sample ID | Change in Potency log/ml | Sat/ Unsat |
| --- | --- | --- |
| PCV1025 PreConc (20.46 kg)--4.5x--100 kDa--PDX Anitgen Content 70.8 pre/288.64 post | 1.5 | unsat |
| Concentrated and Reconstituted with Saline-1 | 0.6 | sat |
| Concentrated and Reconstituted with Saline-2 | no change | sat |
| Concentrated and Reconstituted with Saline-3 | 0.5 | sat |
| 1025 permeate | No submission | n/a |

TABLE 11

PCV 180/181 Virucidal Activity

| Sample ID | % Vaccine Inclusion | Change in Potency log/ml | Sat/ Unsat |
| --- | --- | --- | --- |
| PCV180/181 (49.3 kg)--3.5X--300 kDa--PDX Antigen Content = 43.36 µg pre/ Antigen Content (1) 90.88 µg/ Antigen Content (2) 247.04 µg | n/a | n/a | n/a |
| Preconcentrate vaccine Antigen Content = 16 µg/8.8 µg Actual | 37.0 | 1.2 log/ml loss | unsat |
| Preconcentrate vaccine Antigen Content = 19.2 µg/8.8 µg Actual | 44.5 | 1.2 log/ml loss | unsat |
| Preconcentrate vaccine Antigen Content = 24 µg/15.36 µg Actual | 55.5 | 0.8 log/ml gain | sat |
| 7X reconstituted to 1x vaccine Antigen Content = 16 µg/8.48 µg Actual | 44.0 | 0.6 log/ml gain | sat |
| 7X reconstituted to 1x vaccine Antigen Content = 19.24 µg/12.32 µg Actual | 53.0 | no change | sat |
| 7X reconstituted to 1x vaccine Antigen Content = 24 µg/14.08 µg Actual | 66.0 | 0.3 log/ml gain | sat |

TABLE 12

SUB 504PD Virucidal Activity

| Sample ID | % Vaccine Inclusion | Change in Potency log/ml | Sat/ Unsat |
| --- | --- | --- | --- |
| SUB504PD (~40 kg) 4.3X--300 kDa--PDX Antigen Content = 22.24 µg pre/ Antigen Content (1) = 68.16 µg Antigen Content (2) = 448.48 µg | n/a | n/a | n/a |
| Preconcentrate vaccine Antigen Content = 16 µg/10.24 µg Actual | 79.5 | 0.3 log/ml loss | sat |
| 4.3X vaccine Antigen Content = 16 µg/18.56 µg Actual | 23.5 | 0.1 log/ml gain | sat |
| 4.3X vaccine Antigen Content = 19.2 µg/3.04 µg Actual | 28.0 | 0.7 log/ml gain | sat |
| 4.3X vaccine Antigen Content = 24 µg/5.28 µg Actual | 35.0 | 0.1 log/ml gain | sat |
| 21.5X vaccine Antigen Content = 16 µg/10.08 µg Actual | 3.5 | 0.1 log/ml loss | sat |
| 21.5X vaccine Antigen Content = 19.2 µg/15.2 µg Actual | 4.5 | 0.1 log/ml gain | sat |
| 21.5X vaccine Antigen Content = 24 µg/3.36 µg Actual | 5.5 | 0.3 log/ml gain | sat |
| Filter Wash Antigen Content = 16 µg/12.96 µg Actual | 72.0 | 0.7 gain | sat |

TABLE 13

Process Data

SUB 506: 100,000 NMWC FILTER

| TIME | TMP (psi) | PERM FLOW (ml/min) | FLUX (lmh) |
| --- | --- | --- | --- |
| 13:25 | 12 | 800 | 11.43 |
| 13:59 | 11.5 | 3300 | 47.14 |
| 15:09 | 12.5 | 3800 | 54.29 |
| 15:29 | 12 | 2100 | 30.00 |

TABLE 14

Process Data

SUB 513: 100,000 NMWC FILTER

| TIME | TMP (psi) | PERM FLOW (ml/min) | FLUX (lmh) |
| --- | --- | --- | --- |
| 6:49 | 11.5 | 2600 | 37.14 |
| 8:06 | 11.5 | 2700 | 38.57 |

TABLE 15

Process Data

SUB 512: 300,000 NMWC FILTER

| TIME | TMP (psi) | PERM FLOW (ml/min) | FLUX (lmh) |
| --- | --- | --- | --- |
| 15:25 | 16 | 5000 | 142.86 |
| 18:00 | 13 | 800 | 22.86 |
| 20:03 | 17.5 | 3500 | 100.00 |
| 21:05 | 17.5 | 3000 | 85.71 |
| 21:47 | 18 | 2500 | 71.43 |
| 21:59 | 12.5 | 4000 | 114.29 |

Discussion

Porcine Circovirus Vaccine, Type 2, Killed Baculovirus Vector is a global product manufactured by Boehringer Ingelheim Vetmedica, Inc., in St. Joseph, Mo. and used in the INGELVAC CIRCOFLEX® product. At harvest, virus fluids are aseptically filtered through one or more 2-15 μm pre-filters, and then a 0.8-1.0 μm filter for final filtration. BEI (binary ethylenimine) stock solution is added to the harvest fluids to a final concentration of 5 mM BEI. The fluids are stirred continuously for a minimum of 72 hours and a maximum of 96 hours and may be stored frozen at ≤40° C. or at 4° C.±3° C. A 1.0M sodium thiosulfate solution is added to a final concentration of 5 mM to neutralize any residual BEI.

The neutralized antigen is blended with 0.5% Carbopol solution to 20% v/v with the PCV-2 ORF2 protein content in the final product adjusted by the addition of saline to meet the minimum release requirements of a relative potency greater than, or equal to, 1.0. After bulking, the serial may be stored at 4° C. or filled.

PCV-2 ORF2 material was concentrated post-neutralization by hollow fiber cartridge ultrafiltration. The concentrated material was further processed with two diafiltration volumes of saline solution. Preferred ultrafiltration nominal molecular weight cut-off (NMWC) pore size were determined to include 100,000 NMWC and 300,000 NMWC, each with a 1.0 mm tubule lumen diameter. Both pore sizes were included to provide flexibility in manufacturing in the event of interrupted supply of filter cartridges by the manufacturer. Sodium dodecyl sulfate-polyacrylamide gel electrophoresis (SDS PAGE) gels and potency data indicated no difference in the antigen protein or the potency between the two filter pore sizes.

EXAMPLE 2

This example compares the relative yields of ORF2 using methods of the present invention with methods that are known in the prior art. It is understood that this example represents one of many possible methods for obtaining PCV-2 ORF2 for use with the present methods and compositions.

Materials and Methods

Four 1000 mL spinner flasks were each seeded with approximately $1.0 \times 10^6$ Sf+ cells/ml in 300 mL of insect serum free media, Excell 420 (JRH Biosciences, Inc., Lenexa, Kans.). The master cell culture is identified as SF+ (*Spodoptera frugiperda*) Master Cell Stock, passage 19, Lot#N112-095W. The cells used to generate the SF+ Master Cell Stock were obtained from Protein Sciences Corporation, Inc., Meriden, Conn. The SF+ cell line for this example was confined between passages 19 and 59. Other passages will work for purposes of the present invention, but in order to scale the process up for large scale production, at least 19 passages will probably be necessary and passages beyond 59 may have an effect on expression, although this was not investigated. In more detail, the initial SF+ cell cultures from liquid nitrogen storage were grown in Excell 420 media in suspension in sterile spinner flasks with constant agitation. The cultures were grown in 100 mL to 250 mL spinner flasks with 25 to 150 mL of Excell 420 serum-free media. When the cells had multiplied to a cell density of $1.0$-$8.0 \times 10^6$ cells/mL, they were split to new vessels with a planting density of $0.5$-$1.5 \times 10^6$ cells/mL. Subsequent expansion cultures were grown in spinner flasks up to 36 liters in size or in stainless steel bioreactors of up to 300 liters for a period of 2-7 days at 25-29° C.

After seeding, the flasks were incubated at 27° C. for four hours. Subsequently, each flask was seeded with a recombinant baculovirus containing the PCV-2 ORF2 gene (SEQ ID NO: 4). The recombinant baculovirus containing the PCV-2 ORF2 gene was generated as follows: the PCV-2 ORF2 gene from a North American strain of PCV-2 was PCR amplified to contain a 5' Kozak's sequence (SEQ ID NO: 1) and a 3' EcoR1 site (SEQ ID NO: 2), cloned into the pGEM-T-Easy vector (Promega, Madison, Wis.). Then, it was subsequently excised and subcloned into the transfer vector pVL1392 (BD Biosciences Pharmingen, San Diego, Calif.). The subcloned portion is represented herein as SEQ ID NO: 7. The pVL1392 plasmid containing the PCV-2 ORF2 gene was designated N47-064Y and then co-transfected with BaculoGold® (BD Biosciences Pharmingen) baculovirus DNA into Sf+ insect cells (Protein Sciences, Meriden, Conn.) to generate the recombinant baculovirus containing the PCV-2 ORF2 gene. The new construct is provided herein as SEQ ID NO: 8. The recombinant baculovirus containing the PCV-2 ORF2 gene was plaque-purified and Master Seed Virus (MSV) was propagated on the SF+ cell line, aliquotted, and stored at −70° C. The MSV was positively identified as PCV-2 ORF2 baculovirus by PCR-RFLP using baculovirus specific primers. Insect cells infected with PCV-2 ORF2 baculovirus to generate MSV or Working Seed Virus express PCV-2 ORF2 antigen as detected by polyclonal serum or monoclonal antibodies in an indirect fluorescent antibody assay. Additionally, the identity of the PCV-2 ORF2 baculovirus was confirmed by N-terminal amino acid sequencing. The PCV-2 ORF2 baculovirus MSV was also tested for purity in accordance with 9 C.F.R. 113.27 (c), 113.28, and 113.55. Each recombinant baculovirus seeded into the spinner flasks had varying multiplicities of infection (MOIs). Flask 1 was seeded with 7.52 mL of 0.088 MOI seed; flask 2 was seeded with 3.01 mL of 0.36 MOI seed; flask 3 was seeded with 1.5 mL of 0.18 MOI seed; and flask 4 was seeded with 0.75 mL of 0.09 MOI seed.

After being seeded with the baculovirus, the flasks were then incubated at 27±2° C. for 7 days and were also agitated at 100 rpm during that time. The flasks used ventilated caps to allow for air flow. Samples from each flask were taken every 24 hours for the next 7 days. After extraction, each sample was centrifuged, and both the pellet and the supernatant were separated and then microfiltered through a 0.45-1.0 μm pore size membrane.

Results and Conclusions

The resulting samples then had the amount of ORF2 present within them quantified via an ELISA assay. The ELISA assay was conducted with capture antibody Swine anti-PCV-2 Pab IgG Prot. G purified (diluted 1:250 in PBS) diluted to 1:6000 in 0.05M Carbonate buffer (pH 9.6). 100 μL of the antibody was then placed in the wells of the mictrotiter plate, sealed, and incubated overnight at 37° C. The plate was then washed three times with a wash solution which comprised 0.5 mL of Tween 20 (Sigma, St. Louis, Mo.), 100 mL of 10×D-PBS (Gibco Invitrogen, Carlsbad, Calif.) and 899.5 mL of distilled water. Subsequently, 250 μL of a blocking solution (5 g Carnation Non-fat dry milk (Nestle, Glendale, Calif.) in 10 mL of D-PBS QS to 100 mL with distilled water) was added to each of the wells. The next step was to wash the test plate and then add pre-diluted antigen. The pre-diluted antigen was produced by adding 200 μL of diluent solution (0.5 mL Tween 20 in 999.5 mL D-PBS) to each of the wells on a dilution plate. The sample was then diluted at a 1:240 ratio and a 1:480 ratio, and 100 μL of each of these diluted samples was then added to one of the top wells on the dilution plate (i.e. one top well received 100 μL of the 1:240 dilution and the other received 100 μL of the 1:480 dilution). Serial dilutions were then done for the remainder of the plate by removing 100 μL form each successive well and transferring it to the next well on the plate. Each well was mixed prior to doing the next transfer. The test plate washing included washing the plate three times with the wash buffer. The plate was then sealed and incubated for an hour at 37° C. before being washed three more times with the wash buffer. The detection antibody used was monoclonal antibody to PCV ORF2. It was diluted to 1:300 in diluent solution, and 100 μL of the diluted detection antibody was then added to the wells. The plate was then sealed and incubated for an hour at 37° C. before being washed three times with the wash buffer. Conjugate diluent was then prepared by adding normal rabbit serum (Jackson Immunoresearch, West Grove, Pa.) to the diluent solution to 1% concentration. Conjugate antibody Goat anti-mouse (H+1)-HRP (Jackson Immunoresearch) was diluted in the conjugate diluent to 1:10,000. 100 μL of the diluted conjugate antibody was then added to each of the wells. The plate was then sealed and incubated for 45 minutes at 37° C. before being washed three times with the wash buffer. 100 μL of substrate (TMB Peroxidase Substrate, Kirkgaard and Perry Laboratories (KPL), Gaithersberg, Md.), mixed with an equal volume of Peroxidase Substrate B (KPL) was added to each of the wells. The plate was incubated at room temperature for 15 minutes. 100 μL of 1N HCL solution was then added to all of the wells to stop the reaction. The plate was then run through an ELISA reader.

The results of this assay are provided in Table 17 below:

TABLE 17

| Day | Flask | ORF2 in pellet (μg) | ORF2 in supernatant (μg) |
|---|---|---|---|
| 3 | 1 | 47.53 | 12 |
| 3 | 2 | 57.46 | 22 |
| 3 | 3 | 53.44 | 14 |
| 3 | 4 | 58.64 | 12 |
| 4 | 1 | 43.01 | 44 |
| 4 | 2 | 65.61 | 62 |
| 4 | 3 | 70.56 | 32 |
| 4 | 4 | 64.97 | 24 |
| 5 | 1 | 31.74 | 100 |
| 5 | 2 | 34.93 | 142 |
| 5 | 3 | 47.84 | 90 |
| 5 | 4 | 55.14 | 86 |
| 6 | 1 | 14.7 | 158 |
| 6 | 2 | 18.13 | 182 |
| 6 | 3 | 34.78 | 140 |
| 6 | 4 | 36.88 | 146 |
| 7 | 1 | 6.54 | 176 |
| 7 | 2 | 12.09 | 190 |
| 7 | 3 | 15.84 | 158 |
| 7 | 4 | 15.19 | 152 |

These results indicate that when the incubation time is extended, expression of ORF2 into the supernatant of the centrifuged cells and media is greater than expression in the pellet of the centrifuged cells and media. Accordingly, allowing the ORF2 expression to proceed for at least 5 days and recovering it in the supernate rather than allowing expression to proceed for less than 5 days and recovering ORF2 from the cells, provides a great increase in ORF2 yields, and a significant improvement over prior methods.

EXAMPLE 3

Purification of ORF2 was achieved by microfiltration process followed by a two-step chromatography scheme. The harvest obtained in Example 1 was filtered trough a micro filter membrane having a pore size of 1.2 μm. The micorfiltrate was then purified by size exclusion (gel filtration) using a HiPrep 26/60 Sephacryl S300HR column. A starting sample of 20 ml of the filtrate comprising the PCV-2 ORF2 was loaded on the HiPrep 26/60 Sephacryl S300HR column at a flow rate of 1.0 ml/min and was eluted with 1.5 column volumes of Buffer A (20 mM Tris, pH 6.5, 5 mM DTT). Eight milliliter fractions were collected during the elution step. Fractions No. 10-16 (milititers 10 to 16 of the eluate) from the size exclusion chromatography were pooled and utilized as the starting sample for anion exchange (AIEX) chromatography. These fractions represent the void volume of the sizing column, which is where the PCV-2 ORF2 elutes due to the large molecular weight of PCV-2 ORF2 protein. This technique effectively separates ORF2 from most of the other protein components of an antigen sample.

AIEX was performed using a 5 ml HiTrap Q Sepharose HP column Approximately 48 ml of the void volume fraction pool from the size exclusion experiment was loaded onto the AIEX HiTrap Q Sepharose HP column at a flow rate of 3.0 ml/min. Following a washing step with loading Buffer A (20 mM Tris, pH 6.5, 5 mM DTT) to remove unbound material, protein was eluted with a single step of 8 column volumes of Buffer B (20 mM Tris, pH 6.5, 5 mM DTT, 1.0 M NaCl) and 5 ml fractions were collected. Peak fractions No. 8 and 9 were collected and pooled. The flow-through from the AIEX run was loaded back onto the Q Sepharose column and eluted as described above. From the second run, fractions No 7, 8, and 9 were pooled with the fractions from the first run. A third run of the flow-through material did not result in a significant peak fraction in the eluate, so no fractions were saved from that run.

The fraction pool of approximately 25 ml was dialyzed overnight at 4° C. against 2 liter of phosphate buffered saline, pH 7.4 (Gibco). After dialysis, ORF2 was >95% pure based on SDS-PAGE analysis.

EXAMPLE 4

Solutions of 2-bromoethylamine hydrobromide (BEA), sodium hydroxide (NaOH), and sodium thiosulfate ($Na_2S_2O_3$) were prepared. BEA solution was made by weighing out 1.63 g of BEA (Sigma, B65705, lot 05316EE) and dissolving in 20 ml of purified water ($dH_2O$, aqua dest., here: 'water'). The final concentration of this solution was 0.4 M BEA. The NaOH solution was made by weighing 0.33 g of NaOH (JTBaker, 3722-01, lot E01470) and dissolving in 20 ml of water. The final concentration of this solution was 0.41 M NaOH. Sodium thiosulfate ($Na_2S_2O_3$) solution was prepared by weighing 25 g of $Na_2S_2O_3$ (Sigma S7026, lot 106K0178) and dissolving in 100 ml of water. Once dissolved, the solution was filtered through a 0.2 μm bottle-top filter to sterilize. The final concentration of this solution was 1.0 M $Na_2S_2O_3$.

To prepare binary ethylenimine (BEI), 20 ml of 0.4 M BEA solution was mixed with 20 ml of 0.41 M NaOH and the initial pH was determined to be ~12.5-14.0. The mixture was incubated at 37° C. for one hour and the pH was checked again. The pH after incubation was ~7.0-7.5, and this indicated a successful cyclization reaction of BEA into BEI. The final concentration of BEI was calculated to be ~0.2 M (20 ml of 0.4 M BEA cyclized with an excess of base (0.41 M) in a volume of 40 ml.

The inactivation reactions were as follows (per 100 ml material to be inactivated): The materials to be inactivated were mixed with 2.5 ml freshly prepared BEI. The inactivation reactions were incubated for 72 hr at 37° C. with stirring to continually mix the solutions. After 72 hr, the reactions were neutralized by addition 0.5 ml of 1.0 M sodium thiosulfate. After allowing the thiosulfate to completely mix into the solutions (~15 min of mixing), the inactivated and neutralized materials were stored at 4° C. prior to formulation with adjuvant.

EXAMPLE 5

Preparation of the Test Samples

In order to estimate the immunogenicity of highly purified ORF2 antigen (purity grade of higher than 90%) as compared to non- or less purified ORF2 antigen, 5 ml batches of several test samples were prepared:

TABLE 18

Test samples

| Test sample No | Description |
|---|---|
| #1 | Highly purified ORF2 antigen, inactivated with BEI and mixed with 1 mg/ml Carbopol |
| #2 | Highly purified ORF2 antigen mixed with insect cell debris inactivated with BEI and mixed with 1 mg/ml Carbopol |
| #3 | Insect cell debris (mock control) |
| #4 | PCV-2 ORF2 antigen, non filtered, non purified mixed with 1 mg/ml Carbopol |
| #5 | PCV-2 ORF2 antigen, non filtered, non purified, inactivated with BEI and mixed with 1 mg/ml Carbopol |
| #6 | PCV-2 ORF2 antigen, non purified, inactivated with BEI and mixed with 1 mg/ml Carbopol |

Test sample #1 was produced as follows: PCV-2 ORF2 antigen was produced as described in Example 1 and highly purified as described in Example 3. The highly purified PCV-2 ORF 2 antigen was inactivated with BEI as described in Example 4. After BEI inactivation, the PCV-2 ORF2 antigen was content was adjusted to an amount of about 32 to 32.5 μg per ml test sample and mixed with 1 mg Carbopol 971P (BF Goodrich, Ohio, USA) per ml test sample.

Test sample #2 was produced as follows: PCV-2 ORF2 antigen was produced as described in Example 1 and highly purified as described in Example 3. The highly purified PCV-2 ORF 2 antigen was inactivated with BEI as described in Example 4. After BEI inactivation, PCV-2 ORF2 antigen was mixed with insect cell debris and Carbopol. The final test sample included about $2.06\times10^6$ insect cells, about 32 to 32.5 μg and 1 mg Carbopol 971P per ml test sample.

Test sample #3 was prepared by mixing about $2.06\times10^6$ insect cells with 1 mg Carbopol 971P per ml test sample. Before mixing, insect cells were inactivated by BEI as described in Example 3.

Test sample #4 was produced as follows: the PCV-2 ORF2 antigen was produced as described in Example 1. The PCV-2 ORF2 antigen content in the supernatant was adjusted to an amount of about 32 to 32.5 μg per ml test sample and mixed with 1 mg Carbopol 971P per ml test sample.

Test sample #5 was produced as follows: the PCV-2 ORF2 antigen was produced as described in Example 1. The supernatant was then used for BEI inactivation as described in Example 3. After BEI inactivation, PCV-2 ORF2 antigen was mixed with insect cell debris and Carbopol. The final test sample included about $2.06\times10^6$ insect cells, about 32 to 32.5 μg and 1 mg Carbopol 971P per ml test.

Test sample #6 was produced as follows: PCV-2 ORF2 antigen was produced as described in Example 1. The supernatant of Example 1 then was filtered through a 1.2 μm laboratory scale filter. This filter size was determined previously to be sufficient to filter intact and broken insect cells while allowing the PCV-2 ORF2 antigen to pass through the filter. Afterwards, the filtrate was BEI inactivated as described in Example 3. After BEI inactivation, the PCV-2 ORF2 antigen was content was adjusted to an amount of about 32 to 32.5 μg per ml test sample and mixed with 1 mg Carbopol 971P.

Testing of the Immunogenicity of Each of the Test Sample Clinical Phase:

One-hundred and fifty female Balb/C mice were sourced from Jackson Laboratories (United States) and acclimated for seven days. One mouse from each cage was randomly selected for blood collection on Day 0 for a total of twenty-six samples. A total of ten mice were each inoculated by the subcutaneous route with 0.1-0.2 mL of Dulbecco's Phosphate Buffer.

A total of twenty mice were each inoculated by the subcutaneous route with 0.1-0.2 mL of each test sample (test samples #1 to #6). Each cage contained five mice and all mice in each cage were in the same treatment group. On day twenty-one, all mice were terminally bled. Each blood sample was allowed to clot and the serum was collected by centrifugation. All samples were kept in separate tubes and stored at −80 C±10° C. until testing. Mice were disposed of by incineration.

Sample Testing:

The immunogenicity of each test sample was estimated by measuring the PCV-2 specific antibody response of each test sample by using an in-house PCV-2 specific ELISA. The value of immunogenicity of each test sample is given as a Relative Immunogenicity (RI) value in table 2. This Relative Immunogenicity value is a measure for the ORF2 specific antibody titer obtained in an immunized animal per standardized amount of ORF2 antigen used for immunization.

Instead of using the in-house ELISA, the amount of PCV-2 specific antibodies can also be measured by using the ELISA assay described by Nawagitgul, P., et al. in *Modified indirect porcine circovirus (PCV) type 2-based and recombinant capsid protein (ORF2)-based ELISA for the detection of antibodies to PCV* Clin. Diagn. Lab. Immunol. 9:33-40 (2002), which teaching and content hereby is incorporated by reference. The value measured in such assay can also be used to calculate the Relative Immunogenicity value (see below).

An aliquot of serum from each mouse was pooled with cage mates for a total of twenty-six samples for day 21. An aliquot of all day 0 serum samples were pooled into one sample. The reference was diluted two-fold starting at 1:2 and added in triplicate to each corresponding well. The positive and negative controls were added in triplicate. Each sample was serially diluted two-fold and added to the plate starting at 1:200 in triplicate. The final absorbance at 450 nm was read using a monthly calibrated SoftMax™ Plate reader and all raw OD values were captured electronically and analyzed with Statlia (Brendan Scientific) to calculate the Relative Immunogenicity (RI) values.

Results:

The calculated RI value for the amount of produced antibodies after immunization showed that the purified PCV-2 ORF2 formulation evoked the highest serological (antibody) response to highly purified PCV-2 ORF2 antigen.

The formulation of purified PCV-2 ORF2 together with insect cell debris resulted in a decrease in Relative Immunogenicity (i.e. Immunogenicity) of ORF2 compared to highly purified PCV-2 ORF2 alone. Insect cells alone did not generate an antibody response against PCV-2 ORF2 antigen at all. Test samples 4 to 6, which also do not contain highly purified PCV-2 ORF2 antigen showed also a decreased Relative Immunogenicity compared to highly purified PCV-2 ORF2 alone.

What is claimed is:

1. A method of producing an antigenic composition comprising as at least one first component a porcine circovirus type 2 open reading frame 2 (PCV-2 ORF2)-antigen and having reduced virucidal activity, said method comprising the steps:
   a) obtaining a first liquid containing recombinantly expressed ORF2 antigen of PCV-2, inactivated baculovirus vector, a neutralizing agent, and cell culture media used for the production of recombinant proteins in cultivated host cells;
   b) removing at least a portion of the first liquid containing the PCV-2 ORF2 antigen by an at least one exchange of the portion of the first liquid against a second liquid, wherein the second liquid is different from the first liquid and is a non-virucidal pharmaceutically acceptable buffer selected from the group consisting of a saline buffer, phosphate buffer, or combinations thereof and wherein the at least one exchange of the portion of the first liquid against a second liquid comprises the steps of:
      i) adding the second liquid to the first liquid; and
      ii) concentrating the PCV-2 ORF2 antigen 3-fold to 50-fold by filtration through a semi-permeable membrane with an average pore size of 50 kDa to 500 kDa and removing a portion of the first and second liquids whereby the PCV-2 ORF2 antigenic composition produced has reduced virucidal activity as compared to the first liquid;
   wherein the reduced virucidal activity of the PCV-2 ORF2 antigenic composition can be determined by adding an additional live antigen from at least one other disease-causing organism in swine to the PCV-2 ORF2 antigenic composition and comparing the virucidal activity of the PCV-2 ORF2 antigenic composition on the additional live antigen of the PCV-2 ORF2 antigenic composition with the virucidal activity of a PCV-2 ORF2 antigenic composition having the same additional live antigen as the PCV-2 ORF2 antigenic composition but that has not undergone steps a) and b) and wherein reduced virucidal activity is defined as causing a loss of less than 0.7 log $TCID_{50}$ per ml of a live virus or less than 1 log CFU per ml of a live bacterium of the additional live antigen when the live virus or live bacterium of the additional live antigen is mixed with the PCV-2 ORF2 antigenic composition for 2 or more hours.

2. The method of claim 1, wherein the portion of the first liquid is removed from the isolated PCV-2 ORF2 antigen by a filtration step utilizing a filter.

3. The method of claim 1, wherein concentration step ii) and addition step i) are performed substantially simultaneously.

4. The method of claim 1, wherein concentration step ii) and addition step i) are performed at least two times.

5. The method of claim 2, wherein the filter includes a semi-permeable membrane.

6. The method of claim 5, wherein the semi-permeable membrane has an average pore size that is smaller than the isolated PCV-2 ORF2 antigen and prevents passage of at least 90% of the isolated PCV-2 ORF2 antigen through the semi-permeable membrane pores and holds the isolated PCV-2 ORF2 antigen within the filter.

7. The method of claim 2, wherein the filter has an average pore size that prevents passage of at least 90% of proteins of 50 kDa to 500 kDa in size.

8. The method of claim 1, wherein concentration step ii) concentrates the PCV-2 ORF2 antigen from 3× to 50× as compared to the first liquid.

9. The method of claim 1, wherein the virucidal activity of the PCV-2 ORF2 antigenic composition is reduced by at least 10% as compared to the isolated PCV-2 ORF2 antigen of the first liquid.

10. The method of claim 1, wherein the method further comprises harvesting the isolated PCV-2 ORF2 antigen remaining after step ii).

11. The method of claim 10, wherein the method further comprises purifying the harvested isolated PCV-2 ORF2 antigen by a chromatographic procedure.

12. The method of claim 11, wherein the isolated PCV-2 ORF2 antigen is purified to a purity grade of more than 50% (w/w) with reference to the total amount of protein.

13. The method of claim 1, wherein the method further comprises admixing the isolated PCV-2 ORF2 antigen remaining after step ii) with a further component selected from the group consisting of pharmaceutically acceptable carriers, adjuvants, diluents, excipients, and combinations thereof.

14. The method of claim 13, wherein the further component is an adjuvant.

15. The method of claim 14, wherein the adjuvant is a carbomer.

16. The method of claim 1, wherein the isolated PCV-2 ORF2 antigen comprises virus-like particles of the ORF2 protein.

17. The method of claim 1, wherein the method further comprises combining the PCV-2 ORF2 antigenic composition with at least one additional antigen.

18. The method of claim 17, wherein the at least one additional antigen includes a Porcine Reproductive and Respiratory Syndrome (PRRS) Virus antigen and/or a *Mycoplasma hyopneumoniae* antigen.

19. A PCV-2 ORF2 antigenic composition obtained by the method of claim 1.

20. An immunogenic composition comprising a PCV-2 ORF2 antigenic composition obtained by the method of claim 1.

21. A method of producing an antigenic composition comprising as a first component PCV-2 ORF2 having reduced virucidal activity comprising the steps:
  a) obtaining a first liquid containing an isolated PCV-2 ORF2 antigen and inactivated baculovirus vector, a neutralizing agent, and cell culture media used for the production of recombinant proteins in cultivated host cells wherein the PCV-2 ORF2 antigen is selected from the group consisting of:
    i) a polypeptide comprising the sequence of SEQ ID NO: 5, SEQ ID NO: 6, SEQ ID NO: 9, SEQ ID NO: 10 or SEQ ID NO: 11;
    ii) any polypeptide that is at least 80% homologous and/or identical to the polypeptide of i);
    iii) any immunogenic portion of the polypeptides of i) and/or ii)
    iv) the immunogenic portion of iii), comprising at least 5, 8, or 10 contiguous amino acids of any of the sequences of SEQ ID NO: 5, SEQ ID NO: 6, SEQ ID NO: 9, SEQ ID NO: 10 or SEQ ID NO: 11;
    v) a polypeptide that is encoded by a DNA comprising the sequence of SEQ ID NO: 3 or SEQ ID NO: 4;
    vi) any polypeptide that is encoded by a polynucleotide that is at least 80% homologous and/or identical to the polynucleotide of v);
    vii) any immunogenic portion of the polypeptides encoded by the polynucleotide of v) and/or vi); and
    viii) the immunogenic portion of vii), wherein the polynucleotide coding for the immunogenic portion comprises at least 30 contiguous nucleotides included in the sequences of SEQ ID NO: 3 or SEQ ID NO: 4;
  b) removing at least a portion of the first liquid containing the PCV-2 ORF2 antigen by an at least one exchange of the portion of the first liquid against a second liquid, wherein the second liquid is different from the first liquid and is a non-virucidal pharmaceutically acceptable buffer selected from the group consisting of a saline buffer, phosphate buffer, or combinations thereof and wherein the at least one exchange of the portion of the first liquid against a second liquid comprises the steps of:
    i) adding the second liquid to the first liquid; and
    ii) concentrating the PCV-2 ORF2 antigen 3-fold to 50-fold by filtration through a semi-permeable membrane with an average pore size of 50 kDa to 500 kDa and removing a portion of the first and second liquids whereby the PCV-2 ORF2 antigenic composition produced has reduced virucidal activity as compared to the first liquid; and
  c) adding a component to said PCV-2 ORF2 antigenic composition having reduced virucidal activity, wherein said component is a non-virucidal pharmaceutically acceptable buffer selected from the group consisting of a saline buffer, a phosphate buffer, and combinations thereof;
wherein the reduced virucidal activity of the PCV-2 ORF2 antigenic composition can be determined by adding an additional live antigen from at least one other disease-causing organism in swine to the PCV-2 ORF2 antigenic composition and comparing the virucidal activity of the PCV-2 ORF2 antigenic composition on the additional live antigen added to the PCV-2 ORF2 antigenic composition with the virucidal activity of a PCV-2 ORF2 antigenic composition having the same additional live antigen as the PCV-2 ORF2 antigenic composition but that has not undergone steps a) and b) and wherein reduced virucidal activity is defined as causing a loss of less than 0.7 log $TCID_{50}$ per ml of a live virus or less than 1 log CFU per ml of a live bacterium of the additional live antigen when the live virus or live bacterium of the additional live antigen is mixed with the PCV-2 ORF2 antigenic composition for 2 or more hours.

\* \* \* \* \*

SEQUENCE LISTING

<160> NUMBER OF SEQ ID NOS: 11

<210> SEQ ID NO 1
<211> LENGTH: 8
<212> TYPE: DNA
<213> ORGANISM: Artificial Sequence
<220> FEATURE:
<223> OTHER INFORMATION: This is a modified Kozak's sequence.

<400> SEQUENCE: 1 ccgccatg                                                                    8

<210> SEQ ID NO 2
<211> LENGTH: 6
<212> TYPE: DNA
<213> ORGANISM: Artificial Sequence
<220> FEATURE:
<223> OTHER INFORMATION: This is a recombinant Eco R1 sequence.

<400> SEQUENCE: 2 gaattc                                                                      6

<210> SEQ ID NO 3
<211> LENGTH: 713
<212> TYPE: DNA
<213> ORGANISM: Porcine circovirus

<400> SEQUENCE: 3
cagctatgac gtatccaagg aggcgttacc gcagaagaag acaccgcccc cgcagccatc     60
ttggccagat cctccgccgc cgcccctggc tcgtccaccc ccgccaccgc taccgttgga    120
gaaggaaaaa tggcatcttc aacacccgcc tctcccgcac cttcggatat actgtggaga    180
aggaaaaatg gcatcttcaa cacccgcctc tcccgcacct tcggatatac tgtgacgact    240
ttgttccccc gggaggggg accaacaaaa tctctatacc ctttgaatac tacagaataa    300
gaaaggttaa ggttgaattc tggccctgct cccccatcac ccagggtgat aggggagtgg    360
gctccactgc tgttattcta gatgataact tgtaacaaa ggccacagcc ctaacctatg    420
acccatatgt aaactactcc tcccgccata caatccccca acccttctcc taccactccc    480
gttacttcac acccaaacct gttcttgact ccactattga ttacttccaa ccaaataaca    540
aaaggaatca gcttttggctg aggctacaaa cctctagaaa tgtggaccac gtaggcctcg    600
gcactgcgtt cgaaaacagt aaatacgacc aggactacaa tatccgtgta accatgtatg    660
tacaattcag agaatttaat cttaaagacc ccccacttaa accctaaatg aat           713

<210> SEQ ID NO 4
<211> LENGTH: 713
<212> TYPE: DNA
<213> ORGANISM: Porcine circovirus

<400> SEQUENCE: 4
ccgccatgac gtatccaagg aggcgttacc gcagaagaag acaccgcccc cgcagccatc     60
ttggccagat cctccgccgc cgcccctggc tcgtccaccc ccgccaccgc taccgttgga    120
gaaggaaaaa tggcatcttc aacacccgcc tctcccgcac cttcggatat actgtcaagg    180

```
ctaccacagt cacaacgccc tcctgggcgg tggacatgat gagatttaat attgacgact    240
ttgttccccc gggagggggg accaacaaaa tctctatacc ctttgaatac tacagaataa    300
gaaaggttaa ggttgaattc tggccctgct cccccatcac ccagggtgat aggggagtgg    360
gctccactgc tgttattcta gatgataact ttgtaacaaa ggccacagcc ctaacctatg    420
acccatatgt aaactactcc tcccgccata caatccccca accttctcc taccactccc    480 gttacttcac acccaaacct gttcttgact ccactattga ttacttccaa ccaaataaca    540
aaaggaatca gctttggctg aggctacaaa cctctagaaa tgtggaccac gtaggcctcg    600
gcactgcgtt cgaaaacagt aaatacgacc aggactacaa tatccgtgta accatgtatg    660
tacaattcag agaatttaat cttaaagacc ccccacttga accctaagaa ttc            713

<210> SEQ ID NO 5
<211> LENGTH: 233
<212> TYPE: PRT
<213> ORGANISM: Porcine circovirus

<400> SEQUENCE: 5

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Thr Thr
        50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230

<210> SEQ ID NO 6
<211> LENGTH: 233
<212> TYPE: PRT
<213> ORGANISM: Porcine circovirus

<400> SEQUENCE: 6
```

```
Met Thr Tyr Pro Arg Arg Tyr Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Thr Thr
50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
            165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
            195                 200                 205

Gln Asp Tyr Asn Ile Arg Val Thr Met Tyr Val Gln Phe Arg Glu Phe
210                 215                 220

Asn Leu Lys Asp Pro Pro Leu Glu Pro
225                 230
```

<210> SEQ ID NO 7
<211> LENGTH: 756
<212> TYPE: DNA
<213> ORGANISM: Artificial Sequence
<220> FEATURE:
<223> OTHER INFORMATION: This sequence is from porcine circovirus type
      2, open reading frame 2, together with a portion from the pGEM
      T-easy vector.

<400> SEQUENCE: 7

```
gcggccgcgg gaattcgatc cgccatgacg tatccaagga ggcgttaccg cagaagaaga    60
caccgccccc gcagccatct tggccagatc ctccgccgcc gccctggct cgtccacccc    120 cgccaccgct accgttggag aaggaaaaat ggcatcttca acaccgcct ctcccgcacc    180 ttcggatata ctgtcaaggc taccacagtc acaacgccct cctgggcggt ggacatgatg    240
agatttaata ttgacgactt tgttccccg ggagggggga ccaacaaaat ctctataccc    300
tttgaatact acagaataag aaaggttaag gttgaattct ggccctgctc ccccatcacc    360
cagggtgata ggggagtggg ctccactgct gttattctag atgataactt tgtaacaaag    420
gccacagccc taacctatga cccatatgta aactactcct cccgccatac aatccccaa    480 cccttctcct accactcccg ttacttcaca cccaaacctg ttcttgactc cactattgat    540
tacttccaac caaataacaa aaggaatcag ctttggctga gactacaaac ctctagaaat    600
gtggaccacg taggcctcgg cactgcgttc gaaaacagta atacgacca ggactacaat    660
```
atccgtgtaa ccatgtatgt acaattcaga gaatttaatc ttaaagaccc cccacttgaa 720
ccctaagaat tctatcacta gtgaattcgc ggccgc 756

<210> SEQ ID NO 8
<211> LENGTH: 10387
<212> TYPE: DNA
<213> ORGANISM: Artificial Sequence
<220> FEATURE:
<223> OTHER INFORMATION: This is the porcine circovirus type 2, ORF-2 construct, which includes baculovirus and pGEM T-easy coding sequences.

<400> SEQUENCE: 8
aagctttact cgtaaagcga gttgaaggat catatttagt tgcgtttatg agataagatt 60
gaaagcacgt gtaaaatgtt tcccgcgcgt tggcacaact atttacaatg cggccaagtt 120
ataaaagatt ctaatctgat atgttttaaa acacctttgc ggcccgagtt gtttgcgtac 180
gtgactagcg aagaagatgt gtggaccgca gaacagatag taaaacaaaa ccctagtatt 240
ggagcaataa tcgatttaac caacacgtct aaatattatg atggtgtgca tttttttgcgg 300 gcgggcctgt tatacaaaaa aattcaagta cctggccaga ctttgccgcc tgaaagcata 360
gttcaagaat ttattgacac ggtaaaagaa tttacagaaa agtgtcccgg catgttggtg 420
ggcgtgcact gcacacacgg tattaatcgc accggttaca tggtgtgcag atatttaatg 480
cacaccctgg gtattgcgcc gcaggaagcc atagatagat tcgaaaaagc cagaggtcac 540
aaaattgaaa gacaaaatta cgttcaagat ttattaattt aattaatatt atttgcattc 600
tttaacaaat actttatcct attttcaaat tgttgcgctt cttccagcga accaaaacta 660
tgcttcgctt gctccgttta gcttgtagcc gatcagtggc gttgttccaa tcgacggtag 720
gattaggccg gatattctcc accacaatgt tggcaacgtt gatgttacgt ttatgctttt 780
ggttttccac gtacgtcttt tggccggtaa tagccgtaaa cgtagtgccg tcgcgcgtca 840
cgcacaacac cggatgtttg cgcttgtccg cggggtattg aaccgcgcga tccgacaaat 900
ccaccacttt ggcaactaaa tcggtgacct gcgcgtcttt tttctgcatt atttcgtctt 960
tcttttgcat ggtttcctgg aagccggtgt acatgcggtt tagatcagtc atgacgcgcg 1020
tgacctgcaa atctttggcc tcgatctgct tgtccttgat ggcaacgatg cgttcaataa 1080
actcttgttt tttaacaagt tcctcggttt tttgcgccac caccgcttgc agcgcgtttg 1140
tgtgctcggt gaatgtcgca atcagcttag tcaccaactg tttgctctcc tcctcccgtt 1200
gtttgatcgc gggatcgtac ttgccggtgc agagcacttg aggaattact tcttctaaaa 1260
gccattcttg taattctatg gcgtaaggca atttggactt cataatcagc tgaatcacgc 1320
cggatttagt aatgagcact gtatgcggct gcaaatacag cgggtcgccc cttttcacga 1380
cgctgttaga ggtagggccc ccattttgga tggtctgctc aaataacgat ttgtatttat 1440
tgtctacatg aacacgtata gctttatcac aaactgtata ttttaaactg ttagcgacgt 1500
ccttggccac gaaccggacc tgttggtcgc gctctagcac gtaccgcagg ttgaacgtat 1560
cttctccaaa tttaaattct ccaattttaa cgcgagccat tttgatacac gtgtgtcgat 1620
tttgcaacaa ctattgtttt ttaacgcaaa ctaaacttat tgtggtaagc aataattaaa 1680
tatgggggaa catgcgccgc tacaacactc gtcgttatga acgcagacgg cgccggtctc 1740
ggcgcaagcg gctaaaacgt gttgcgcgtt caacgcggca aacatcgcaa aagccaatag 1800
tacagttttg atttgcatat taacggcgat ttttttaaatt atcttattta ataaatagtt 1860
atgacgccta caactccccg cccgcgttga ctcgctgcac ctcgagcagt tcgttgacgc 1920

```
cttcctccgt gtggccgaac acgtcgagcg ggtggtcgat gaccagcggc gtgccgcacg    1980
cgacgcacaa gtatctgtac accgaatgat cgtcgggcga aggcacgtcg gcctccaagt    2040
ggcaatattg gcaaattcga aaatatatac agttgggttg tttgcgcata tctatcgtgg    2100
cgttgggcat gtacgtccga acgttgattt gcatgcaagc cgaaattaaa tcattgcgat    2160
tagtgcgatt aaaacgttgt acatcctcgc ttttaatcat gccgtcgatt aaatcgcgca    2220
atcgagtcaa gtgatcaaag tgtggaataa tgttttcttt gtattcccga gtcaagcgca    2280
gcgcgtattt taacaaacta gccatcttgt aagttagttt catttaatgc aactttatcc    2340
aataatatat tatgtatcgc acgtcaagaa ttaacaatgc gcccgttgtc gcatctcaac    2400
acgactatga tagagatcaa ataaagcgcg aattaaatag cttgcgacgc aacgtgcacg    2460
atctgtgcac gcgttccggc acgagctttg attgtaataa gttttttacga agcgatgaca    2520 tgacccccgt agtgacaacg atcacgccca aaagaactgc cgactacaaa attaccgagt    2580
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880 aatttttaaaa aacgcagcaa gagaaacatt tgtatgaaag aatgcgtaga aggaaagaaa    2940
aatgtcgtcg acatgctgaa caacaagatt aaatatgcctc cgtgtataaa aaaaatattg    3000
aacgatttga agaaaacaa tgtaccgcgc ggcggtatgt acaggaagag gtttatacta    3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatcttttta    3180 atcaaatccc aagatgtgta taaaccacca aactgccaaa aaatgaaaac tgtcgacaag    3240
ctctgtccgt ttgctggcaa ctgcaagggt ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatatttaa    3420 aatcatttc aaatgattca cagttaattt gcgacaatat aatttatttt tcacataaac    3480
tagacgcctt gtcgtcttct tcttcgtatt ccttctcttt ttcattttc tcctcataaa    3540 aattaacata gttattatcg tatccatata tgtatctatc gtatagagta aattttttgt    3600
tgtcataaat atatatgtct tttttaatgg ggtgtatagt accgctgcgc atagttttc    3660 tgtaatttac aacagtgcta ttttctggta gttcttcgga gtgtgttgct ttaattatta    3720
aatttatata atcaatgaat ttgggatcgt cggttttgta caatatgttg ccggcatagt    3780
acgcagcttc ttctagttca attacaccat ttttagcag caccggatta acataacttt    3840
ccaaaatgtt gtacgaaccg ttaaacaaaa acagttcacc tcccttttct atactattgt    3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atcagatctg    4140
cagcggccgc gggaattcga tccgccatga cgtatccaag gaggcgttac cgcagaagaa    4200
gacaccgccc ccgcagccat cttggccaga tcctccgccg ccgcccctgg ctcgtccacc    4260
```

```
cccgccaccg ctaccgttgg agaaggaaaa atggcatctt caacacccgc ctctcccgca    4320
ccttcggata tactgtcaag gctaccacag tcacaacgcc ctcctgggcg gtggacatga    4380
tgagatttaa tattgacgac tttgttcccc cgggaggggg gaccaacaaa atctctatac    4440
cctttgaata ctacagaata agaaaggtta aggttgaatt ctggccctgc tcccccatca    4500
cccagggtga taggggagtg ggctccactg ctgttattct agatgataac tttgtaacaa    4560
aggccacagc cctaacctat gacccatatg taaactactc ctcccgccat acaatccccc    4620 aaccctctc ctaccactcc cgttacttca cacccaaacc tgttcttgac tccactattg    4680
attacttcca accaaataac aaaaggaatc agctttggct gaggctacaa acctctagaa    4740
atgtggacca cgtaggcctc ggcactgcgt tcgaaaacag taaatacgac caggactaca    4800
atatccgtgt aaccatgtat gtacaattca gagaatttaa tcttaaagac cccccacttg    4860
aaccctaaga attctatcac tagtgaattc gcggccgccg gccgctccag aattctagaa    4920
ggtacccggg atccttttcct gggacccggc aagaaccaaa aactcactct cttcaaggaa    4980
atccgtaatg ttaaacccga cacgatgaag cttgtcgttg gatggaaagg aaaagagttc    5040
tacagggaaa cttggacccg cttcatggaa gacagcttcc ccattgttaa cgaccaagaa    5100
gtgatggatg ttttccttgt tgtcaacatg cgtcccacta gacccaaccg ttgttacaaa    5160
ttcctggccc aacacgctct gcgttgcgac cccgactatg tacctcatga cgtgattagg    5220
atcgtcgagc cttcatgggt gggcagcaac aacgagtacc gcatcagcct ggctaagaag    5280
ggcggcggct gcccaataat gaaccttcac tctgagtaca ccaactcgtt cgaacagttc    5340
atcgatcgtg tcatctggga gaacttctac aagcccatcg tttacatcgg taccgactct    5400
gctgaagagg aggaaattct ccttgaagtt tccctggtgt tcaaagtaaa ggagtttgca    5460
ccagacgcac ctctgttcac tggtccggcg tattaaaaca cgatacattg ttattagtac    5520
atttattaag cgctagattc tgtgcgttgt tgatttacag acaattgttg tacgtatttt    5580 ataattcat taaatttata atctttaggg tggtatgtta gagcgaaaat caaatgattt    5640
tcagcgtctt tatatctgaa tttaaatatt aaatcctcaa tagatttgta aaataggttt    5700
cgattagttt caaacaaggg ttgttttttcc gaaccgatgg ctggactatc taatggattt    5760
tcgctcaacg ccacaaaact tgccaaatct tgtagcagca atctagcttt gtcgatattc    5820
gtttgtgttt tgttttgtaa taaaggttcg acgtcgttca aaatattatg cgcttttgta    5880
tttctttcat cactgtcgtt agtgtacaat tgactcgacg taaacacgtt aaataaagct    5940
tggacatatt taacatcggg cgtgttagct ttattaggcc gattatcgtc gtcgtcccaa    6000
ccctcgtcgt tagaagttgc ttccgaagac gattttgcca tagccacacg acgcctatta    6060
attgtgtcgg ctaacacgtc cgcgatcaaa tttgtagttg agcttttggg aattatttct    6120
gattgcgggc gttttttgggc gggtttcaat ctaactgtgc ccgattttaa ttcagacaac    6180
acgttagaaa gcgatggtgc aggcggtggt aacatttcag acggcaaatc tactaatggc    6240
ggcggtggtg gagctgatga taaatctacc atcggtggag gcgcaggcgg ggctggcggc    6300
ggaggcggag gcggaggtgg tggcggtgat gcagacggcg gtttaggctc aaatgtctct    6360
ttaggcaaca cagtcggcac ctcaactatt gtactggttt cggcgccgt ttttggtttg    6420 accggtctga gacgagtgcg attttttttcg tttctaatag cttccaacaa ttgttgtctg    6480
tcgtctaaag gtgcagcggg ttgaggttcc gtcggcattg gtggagcggg cggcaattca    6540
gacatcgatg gtggtggtgg tggtggaggc gctggaatgt taggcacggg agaaggtggt    6600
ggcggcggtg ccgccggtat aatttgttct ggtttagttt gttcgcgcac gattgtgggc    6660
```

```
accggcgcag gcgccgctgg ctgcacaacg gaaggtcgtc tgcttcgagg cagcgcttgg   6720
ggtggtggca attcaatatt ataattggaa tacaaatcgt aaaaatctgc tataagcatt   6780
gtaatttcgc tatcgtttac cgtgccgata tttaacaacc gctcaatgta agcaattgta   6840
ttgtaaagag attgtctcaa gctcgccgca cgccgataac aagccttttc attttttacta  6900 cagcattgta gtggcgagac acttcgctgt cgtcgacgta catgtatgct tgttgtcaa    6960 aaacgtcgtt ggcaagcttt aaaatattta aagaacatc  tctgttcagc accactgtgt   7020
tgtcgtaaat gttgttttg  ataatttgcg cttccgcagt atcgacacgt tcaaaaaatt   7080
gatgcgcatc aattttgttg ttcctattat tgaataaata agattgtaca gattcatatc   7140
tacgattcgt catggccacc acaaatgcta cgctgcaaac gctggtacaa ttttacgaaa   7200
actgcaaaaa cgtcaaaact cggtataaaa taatcaacgg gcgctttggc aaaatatcta   7260
ttttatcgca caagcccact agcaaattgt atttgcagaa acaatttcg  gcgcacaatt   7320 ttaacgctga cgaaataaaa gttcaccagt taatgagcga ccacccaaat tttataaaaa   7380
tctattttaa tcacggttcc atcaacaacc aagtgatcgt gatggactac attgactgtc   7440 ccgattatt  tgaaacacta caaattaaag gcgagctttc gtaccaactt gttagcaata   7500
ttattagaca gctgtgtgaa gcgctcaacg atttgcacaa gcacaatttc atacacaacg   7560
acataaaact cgaaaatgtc ttatatttcg aagcacttga tcgcgtgtat gtttgcgatt   7620
acggattgtg caaacacgaa aactcactta gcgtgcacga cggcacgttg gagtatttta   7680
gtccggaaaa aattcgacac acaactatgc acgtttcgtt tgactggtac gcggcgtgtt   7740
aacatacaag ttgctaacgt aatcatggtc atagctgttt cctgtgtgaa attgttatcc   7800
gctcacaatt ccacacaaca tacgagccgg aagcataaag tgtaaagcct ggggtgccta   7860
atgagtgagc taactcacat taattgcgtt gcgctcactg cccgctttcc agtcgggaaa   7920
cctgtcgtgc cagctgcatt aatgaatcgg ccaacgcgcg gggagaggcg gtttgcgtat   7980
tgggcgctct tccgcttcct cgctcactga ctcgctgcgc tcggtcgttc ggctgcggcg   8040
agcggtatca gctcactcaa aggcggtaat acggttatcc acagaatcag gggataacgc   8100
aggaaagaac atgtgagcaa aaggccagca aaaggccagg aaccgtaaaa aggccgcgtt   8160
gctggcgttt ttccataggc tccgcccccc tgacgagcat cacaaaaatc gacgctcaag   8220
tcagaggtgg cgaaacccga caggactata aagataccag gcgtttcccc ctggaagctc   8280
cctcgtgcgc tctcctgttc cgaccctgcc gcttaccgga tacctgtccg cctttctccc   8340
ttcgggaagc gtggcgcttt ctcatagctc acgctgtagg tatctcagtt cggtgtaggt   8400
cgttcgctcc aagctgggct gtgtgcacga accccccgtt cagcccgacc gctgcgcctt   8460
atccggtaac tatcgtcttg agtccaaccc ggtaagacac gacttatcgc cactggcagc   8520
agccactggt aacaggatta gcagagcgag gtatgtaggc ggtgctacag agttcttgaa   8580
gtggtggcct aactacggct acactagaag gacagtattt ggtatctgcg ctctgctgaa   8640
gccagttacc ttcggaaaaa gagttggtag ctcttgatcc ggcaaacaaa ccaccgctgg   8700
tagcggtggt ttttttgttt gcaagcagca gattacgcgc agaaaaaaag gatctcaaga   8760
agatcctttg atcttttcta cggggtctga cgctcagtgg aacgaaaact cacgttaagg   8820
gattttggtc atgagattat caaaaaggat cttcacctag atccttttaa attaaaaatg   8880
aagttttaaa tcaatctaaa gtatatatga gtaaacttgg tctgacagtt accaatgctt   8940
aatcagtgag gcacctatct cagcgatctg tctatttcgt tcatccatag ttgcctgact   9000
```

```
cccgtcgtg tagataacta cgatacggga gggcttacca tctggcccca gtgctgcaat    9060
gataccgcga gacccacgct caccggctcc agatttatca gcaataaacc agccagccgg    9120
aagggccgag cgcagaagtg gtcctgcaac tttatccgcc tccatccagt ctattaattg    9180
ttgccgggaa gctagagtaa gtagttcgcc agtaatagt ttgcgcaacg ttgttgccat     9240
tgctacaggc atcgtggtgt cacgctcgtc gtttggtatg gcttcattca gctccggttc    9300
ccaacgatca aggcgagtta catgatcccc catgttgtgc aaaaaagcgg ttagctcctt    9360
cggtcctccg atcgttgtca gaagtaagtt ggccgcagtg ttatcactca tggttatggc    9420
agcactgcat aattctctta ctgtcatgcc atccgtaaga tgcttttctg tgactggtga    9480
gtactcaacc aagtcattct gagaatagtg tatgcggcga ccgagttgct cttgcccggc    9540
gtcaatacgg gataataccg cgccacatag cagaacttta aaagtgctca tcattggaaa    9600
acgttcttcg gggcgaaaac tctcaaggat cttaccgctg ttgagatcca gttcgatgta    9660
acccactcgt gcacccaact gatcttcagc atcttttact ttcaccagcg tttctgggtg    9720
agcaaaaaca ggaaggcaaa atgccgcaaa aaagggaata agggcgacac ggaaatgttg    9780
aatactcata ctcttccttt ttcaatatta ttgaagcatt tatcagggtt attgtctcat    9840
gagcggatac atatttgaat gtatttagaa aaataaacaa ataggggttc cgcgcacatt    9900
tccccgaaaa gtgccacctg acgtctaaga accattatt atcatgacat aacctataa     9960 aaataggcgt atcacgaggc cctttcgtct cgcgcgtttc ggtgatgacg gtgaaaacct   10020
ctgacacatg cagctcccgg agacggtcac agcttgtctg taagcggatg ccgggagcag   10080
acaagcccgt cagggcgcgt cagcgggtgt tggcgggtgt cggggctggc ttaactatgc   10140
ggcatcagag cagattgtac tgagagtgca ccatatgcgg tgtgaaatac cgcacagatg   10200
cgtaaggaga aaataccgca tcaggcgcca ttcgccattc aggctgcgca actgttggga   10260
agggcgatcg gtgcgggcct cttcgctatt acgccagctg gcgaaagggg gatgtgctgc   10320
aaggcgatta agttgggtaa cgccagggtt ttcccagtca cgacgttgta aaacgacggc   10380
cagtgcc                                                             10387
```

<210> SEQ ID NO 9
<211> LENGTH: 20
<212> TYPE: PRT
<213> ORGANISM: Porcine circovirus

<400> SEQUENCE: 9

Ser Tyr Pro Arg Arg Arg Tyr Arg Arg Arg His His Pro Pro Ser
1               5                   10                  15

His Leu Gly Gln
            20

<210> SEQ ID NO 10
<211> LENGTH: 19
<212> TYPE: PRT
<213> ORGANISM: Porcine circovirus

<400> SEQUENCE: 10

Pro Arg His His Tyr Arg Pro Arg Arg Lys Asn Gly Ile Phe Asn Thr
1               5                   10                  15

Thr Leu Ser

<210> SEQ ID NO 11
<211> LENGTH: 233
<212> TYPE: PRT

```
<213> ORGANISM: Artificial Sequence
<220> FEATURE:
<223> OTHER INFORMATION: This is an amino acid sequence for porcine
      circovirus type 2, open reading frame 2.

<400> SEQUENCE: 11

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Arg Thr
        50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Lys Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
                115                 120                 125

Phe Val Thr Lys Ala Thr Ala Leu Thr Tyr Asp Pro Tyr Val Asn Tyr
            130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
                180                 185                 190

Val Asp His Val Gly Leu Gly Thr Ala Phe Glu Asn Ser Ile Tyr Asp
            195                 200                 205

Gln Asp Tyr Asn Ile Arg Val Thr Met Tyr Val Gln Phe Arg Glu Phe
        210                 215                 220

Asn Leu Lys Asp Pro Pro Leu Lys Pro
225                 230
```